US009056102B2

(12) United States Patent
Quinn

(10) Patent No.: US 9,056,102 B2
(45) Date of Patent: Jun. 16, 2015

(54) VEGF-ACTIVATED TRAIL LIGANDS

(71) Applicant: The Regents of the University of California, Oakland, CA (US)

(72) Inventor: Timothy P. Quinn, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/655,142

(22) Filed: Oct. 18, 2012

(65) Prior Publication Data

US 2013/0251821 A1 Sep. 26, 2013

Related U.S. Application Data

(63) Continuation of application No. 12/063,897, filed as application No. PCT/US2006/031991 on Aug. 15, 2006, now Pat. No. 8,324,169.

(60) Provisional application No. 60/708,723, filed on Aug. 15, 2005.

(51) Int. Cl.
*A61K 38/16* (2006.01)
*C07K 19/00* (2006.01)
*A61K 38/45* (2006.01)
*C07K 14/705* (2006.01)
*C07K 14/71* (2006.01)
*A61K 38/19* (2006.01)
*A61K 45/06* (2006.01)
*C07K 14/525* (2006.01)
*C12N 9/12* (2006.01)

(52) U.S. Cl.
CPC .............. *A61K 38/45* (2013.01); *C07K 2319/75* (2013.01); *C07K 14/705* (2013.01); *C07K 14/70578* (2013.01); *C07K 14/71* (2013.01); *C07K 2319/00* (2013.01); *A61K 38/191* (2013.01); *A61K 45/06* (2013.01); *C07K 14/525* (2013.01); *C12N 9/12* (2013.01)

(58) Field of Classification Search
None
See application file for complete search history.

(56) References Cited

U.S. PATENT DOCUMENTS 7,462,713 B2 12/2008 Benedict et al.
2003/0064053 A1 4/2003 Liu et al.
2004/0053249 A1 3/2004 Tohma
2004/0197876 A1 10/2004 Scchopp et al.
2005/0232931 A1* 10/2005 Ma et al.

FOREIGN PATENT DOCUMENTS

WO 2004/085478 A2 10/2004

OTHER PUBLICATIONS

Bremer et al., Simultaneous inhibition of epidermal growth factor receptor (EGFR) signaling and enhanced activation of tumor necrosis factor-related apoptosis-inducing ligand (TRAIL) receptor-mediated apoptosis induction by an scFv:sTRAIL fusion protein with specificity for human EGFR, J. Biol. Chem. 280:10025-10033, Jan. 2005.*
Wu et al., Regression of human mammary adenocarcinoma by systemic administration of a recombinant gene encoding the hFlex-TRAIL fusion protein, Mol. Ther. 3(3):368-374, Mar. 2001.*
Kim et al., The secretable form of trimeric TRAIL, a potent inducer of apoptosis, Biochem. Biophys. Res. Comm. 321(4):930-935, Sep. 3, 2004.*
Seol et al., Cysteine 230 modulates tumor necrosis factor-related apoptosis-inducing ligand activity, Cancer Res. 60:3152-3154, 2000.*
Kavurma et al., Signaling and transcriptional control of Fas ligand gene expression, Cell Death and Diff. 10:36-44, 2003.*
Bodmer et al., The molecular architecture of the TNF superfamily, Trends in Biochem. Sci. 27(1):19-26, Jan. 2002.*
Pitti et al., Induction of apoptosis by Apo-2 ligand, a new member of the tumor necrosis factor cytokine family, J. Biol. Chem., 271(22):12687-90,1996.*
Quinn, Timothy P. et al.; "A Receptor for Vascular Endothelial Growth Factor That Stimulates Endothelial Apoptosis"; 2001, Cancer Research, vol. 61, pp. 8629-8637.

* cited by examiner

*Primary Examiner* — Claire Kaufman
(74) *Attorney, Agent, or Firm* — Kilpatrick Townsend & Stockton LLP

(57) ABSTRACT

The present invention provides fusion proteins comprising an extracellular domain of a VEGF receptor and a death ligand. The fusion proteins bind to VEGF and to death receptors on tumor cells thereby inhibiting VEGF activation of VEGF receptors and inducing apoptosis in the tumor cells. Fusion proteins of the present invention are useful for inducing apoptosis and cytotoxic effects in cells, treating cancer and diseases or disorders related to unregulated angiogenesis and/or vasculogenesis. Thus, this invention further provides methods for treating angiogenesis related diseases using the fusion proteins, polynucleotides encoding the fusion proteins, vectors containing the polynucleotides, pharmaceutical compositions and kits containing the fusion proteins or the polynucleotides encoding the fusion proteins.

15 Claims, 19 Drawing Sheets

[INTRACELLULAR DOMAIN••••••••••••••••••••••••••••••••
H   1 MQQPFNYPYPQIYWVDSSASSPWAPPGTVLPCPTSVPRRPGQRRPPPPPPPPPLPPPPPP
M   1 **M*C*F****T*S*****S*F*SCGG*D*********VSPL*SQ
R   1 **V*C********T*****S*FS**S*GG*********SPL*SQ

••••••INTRACELLULAR] [•••TRANSMEMBRANE••••]
 61 PPLPPLPLPPLKKRGNHSTGLCLLVMFFMVLVALVGLGLGMFQLFHLQKELAELRESTSQ
 61 *-LPT****K-D*N*N*W*P*V********M*Y************F*N*
 61 **-*LPS**K-D-NIE*W*P*I********M*Y************F*NH

CLEAVAGE  ><          [•••••••••••TRIMERIZATION DOMAIN••••••••••
121 MHTASSLEKQIGHPSPPPEKKELRKVAHLTGKSNSRSMPLEWEDTYGIVLLSGVKYKKGG
119 SLKVFANT*S****P*S****NPH*I***********TA*I*********
118 SLRVFANT*S*T*KP*S****NPR*I***********TA*I*********

••]
181 LVINETGLYFVYSKVYFRGQSCNNLPLSHKVYMRNSKYPQDLVMMEGKMMSYCTTGQMWA
179 *******************QN*********E*L**E*RLN****I
178 ***A**********SQ******F*G*LE*KLN****I

••••••••••••RECEPTOR BINDING]
241 RSSYLGAVFNLTSADHLYVNVSELSLVNFEESQTFFGLYKL
239 H******************I*Q*I*K******
238 H*********V****I*Q*I*K******

FIG. 2

```
              [ SIGNAL SEQUENCE ]                          [••••••••••••
Human   1   MQSKVLLAVALWLCVETRAASVGLPSVSLDLPRLSIQKDILTIKANTTLQITCRGQRDLD
Mouse   1   *EA***F**********GDF*HP*KT***L*************
Rat     1   *E*RA*****F********GDHP*KT***L*************
hR1     1   MVSYWDTGV*LC**LS*LLLTGS*S*S---K*KD*E**LKGTQHIMQ*GQHLQ*EAAHK

••••••••••IgG-like domain 1•••••••••••••••••••••••••••••]
       61   WLWPNNQSGSEQRVEVTECSDG----LFCKTLTIPKVIGNDTGAYKCFY------RETDLASVIYVYV
       61   *****A*RDEL****GG*--DSI********R*V*********S*------*DV*ITV**
       61   ***TPRDEL**G*S----I******V*R*V*************------*D**VS*IV****
       61   *SL*EMV*KESE*LSI*KSAC*RNGKQS*LNTAQA*H**F*S*K*LAVPTSKKKETE*A**IFI

[••••IgG-like domain 2 binds VEGF••••
      119   QDYRSPFIASVSDQHGVVYITENKNKTVVIPCLGSISNLNVSLCARYPEKRFVPDGNRIS
      121   R**************I*****************R**************************
      119   H******EI**************R************************
      129   S*TGR**VEMY*EIPEIIHM**GRE--L****RVTSP*IT*T*-KKF*LDTLI***K**I

••••••••••••••••••••••••••]      [•••••••••••••••
      179   WDSKKGFTIPSYMISYAGMVFCEAKINDESYQSIMYIVVVVGYRIYDVVLSPSHGIELSV
      181   *EI*L*******************T*************I*P*E****A
      179   *E**********************T****L*********P*E****A
      186   *R*I*SNATYKEI*LLT***TV*GHL*KTNYLTHRQTNTI*DVQIST*-RPVK*LR

••••••••••••••••IgG-like domain 3 binds VEGF•••••••••••••••
      239   GEKLVLNCTARTELNVGIDFNWEYPSSKHQHKKLVNRDLKTQSGSEMKKFLSTLTIDGVT
      241   ****************LT*HS*PSH*I****V*PFP*TVA*M*****ES
      239   ******************L**S*QF*********I****V*SLP*TVA*M*******S**
      245   *HT*******T*P**TRVQMT*S**DE*NKRASVRR*I--D**N*HANI*Y*V****KMQ

•••••••••••••••••••]      [••••••••••••••••••••••••
      299   RSDQGLYTCAASSGLMTKKNSTFVRVHEKPFVAFGSGMESLVEATVGER-VRIPAKYLGYP
      301   K****E***V****R*I*R*R******T***I******K********SQ-****V***S**
      299   K**E*T*Y******K*TI****K****SQ-V*S**
      303   NK*K*****RVR**PSF*SVN*S*HIYD*A*ITVKHRKQQVL*TVA*K*SY*LSM*VKAF*

•••IgG-like domain 4 not required for VEGF binding••••••••]
      359   PPEIKWYKNGIPL--ESNHTIKAGHVLTIMEVSERDTGNYTVILTNPISKEKQSHVVSLVVY
      361   A*D****R**R*I--***Y*MIV*DE********T***A************M****M****N
      359   A*D****R**R*I--***Y*MIV*DE************A************M****M****N
      364   S**VV*L*D*L*ATEK*ARYLTR*YS*I*KD*T*E*****IL*SIKQ*NVFKNLTAT*I*N

[•••IgG-like domain 5 not required for VEGF binding••••••
      419   VPPQIGEKSLISPVDS--YQYGTTQTLTCTVYAIPPPHHIHWYWQLEEECANEPSQAVSVTN
      421   ******AM--***M******NL*Q******A*SYR*G*----*S
      419   ******AM--***M******NL*Q******A*SYR*----
      426   *K***Y**AVS*FP*PAL*PL*SR*I****A*G**Q*T-*K*F*H---P*NHNH*E*RCDFC
```

FIG. 3

```
       ••••••••••••••••••••••••••••••••••••••••••••••••••
479    PYPCEEWRSVEDFQGGNKIEVNKNQFALIEGKNKTVSTLVIQAANVSALYKCEAVNKVGR
477    **A*K*H**********T*Y********************IA**
475    **T*K***H*K**********T*Y*************Y*IA**
484    SNNE*SFILDA*SNMRSITQRM*I****MA**VADSRI*GI*I*S****T

•••••••••]  [•IgG-like domain 6 not required for VEGF binding•
539    GERVISFHVTRGPE-ITLQPDMQPTEQESVSLWCTADRSTFENLTWYKLGPQPLPIHVGEL
537    *******I-VAA*******LN********S*ATSV*M**S
535    *******I-VATRMLN********S*ATSV*M**S
544    VG*N***YI*DV*NGFHVNLEKM***G*DLK*SVNKFLYRDVIL*RT----VNNRTM

••••••••••••••••••••••••••••••••••••••••••••••••••••
599    PTPVCKNLDTLWKLNATMFSNSTNDILIMELKNASLQDQGDYVCLAQDRKTKKRHCVVRQ
597    L*******A*****G*************VAFQ***********S***K*******L*K*
595    L*******A*****G*V***********VAFQ******N***S***K*******L*K*
601    HYSIS*Q-----*MAI*KEHSI*LNLT**---*V****S*T*A*R*RNVY*GEEILQKKE

•]      [•••IgG-like domain 7 not required for VEGF binding•••
659    LTVLERVAPTITGNLENQTTSIGESIEVSCTASGNPPPQIMWFKDNETLVEDSGIVLKDGNR
657    *II*MM********T*T**T*P****T*H*T**************R**
655    *VI*MM********T*T**V*PT****T*L*T********************
653    I*IRDQEYLLRSDH*VA*SS*TTLD*H*N*V*E*T*N*HKIQQEP**I*GP*SS

•••••••••••••••••••••••••••••]         [•TRANSMEMBRANE•
721    NLTIRRVRKEDEGLYTCQACSVLGCAKVEAFFIIEGAQEKTNLEIIILVGTAVIAMFFWL
719    **********G*******N*****RA*TL**********V**************
717    **********G*******N*****RA*TL****V******V*************
715    T*F*ETE**V*H*K*TNQK*SVESS*YLTVQ*TSD*S***L*T*TC*C*A*TL***

••••••••][•••••INTRACELLULAR DOMAIN•••••••>
781    LLVIILRTVKRANGGELKTGYLSIVMDPDELPLDEHCER•••
779    ****LV******E********************R***
777    ****LV******E********************R***
775    **TLLI*KM**SSS-*IDI*V*Q***
```

FIG. 3 (CONT.)

```
     [Signal sequence]    [****************************
  1  MERGLPLLCAVLALVLAPAGAFRNDKCGDTIKIESPGYLTSPGYPHSYHPSEKCEWLIQA

**********A Domain-Not required for VEGF Binding*************
 61  PDPYQRIMINFNPHFDLEDRDCKYDYVEVFDGENENGHFRGKFCGKIAPPPVVSSGPFLF

************************************************************
121  IKFVSDYETHGAGFSIRYEIFKRGPECSQNYTTPSGVIKSPGFPEKYPNSLECTYIVFAP

************************************************************
181  KMSEIILEFESFDLEPDSNPPGGMFCRYDRLEIWDGFPDVGPHIGRYCGQKTPGRIRSSS

************************]       [*************************
241  GILSMVFYTDSAIAKEGFSANYSVLQSSVSEDFKCMEALGMESGEIHSDQITASSQYSTN

******************B DOMAIN BINDS VEGF************************
301  WSAERSRLNYPENGWTPGEDSYREWIQVDLGLLRFVTAVGTQGAISKETKKKYYVKTYKI

************************************************************
361  DVSSNGEDWITIKEGNKPVLFQGNTNPTDVVVAVFPKPLITRFVRIKPATWETGISMRFE

************************************************************
421  VYGCKITDYPCSGMLGMVSGLISDSQITSSNQGDRNWMPENIRLVTSRSGWALPPAPHSY

************************************************************
481  INEWLQIDLGEEKIVRGIIIQGGKHRENKVFMRKFKIGYSNNGSDWKMIMDDSKRKAKSF

************************]
541  EGNNNYDTPELRTFPALSTRFIRIYPERATHGGLGLRMELLGCEVEAPTAGPTTPNGNLV

[****************
601  DECDDDQANCHSGTGDDFQLTGGTTVLATEKPTVIDSTIQSEFPTYGFNCEFGWGSHKTF

******C/MAM DOMAIN NOT REQUIRED FOR VEGF BINDING*************
661  CHWEHDNHVQLKWSVLTSKTGPIQDHTGDGNFIYSQADENQKGKVARLVSPVVYSQNSAH

************************************************************
721  CMTFWYHMSGSHVGTLRVKLRYQKPEEYHQLVWMAIGHQGDHWKEGRVLLHKSLKLYQVI

**********************************]
781  FEGEIGKGNLGGIAVDDISINNHISQEDCAKPADLDKKNPEIKIDETGSTPGYEGEGEGD

[*TRANSMEMBRANE***]
841  KNISRKPGNVLKTLDPILITIIAMSALGVLLGAVCGVVLYCACWHNGMSERNLSALENYN
```

FIG. 4

1     ATGGAGAGCAAGGCGCTGCTAGCTGTCGCTCTGTGGTTCTGCGTGGAGACCCGAGCCGCC
61    TCTGTGGGTTTGCCTGGCGATTTTCTCCATCCCCCCAAGCTCAGCACACAGAAAGACATA
121   CTGACAATTTTGGCAAATACAACCCTTCAGATTACTTGCAGGGGACAGCGGGACCTGGAC
181   TGGCTTTGGCCCAATGCTCAGCGTGATTCTGAGGAAAGGGTATTGGTGACTGAATGCGGC
241   GGTGGTGACAGTATCTTCTGCAAAACACTCACCATTCCCAGGGTGGTTGGAAATGATACT
301   GGAGCCTACAAGTGCTCGTACCGGGACGTCGACATAGCCTCCACTGTTTATGTCTATGTT
361   CGAGATTACAGATCACCATTCATCGCCTCTGTCAGTGACCAGCATGGCATCGTGTACATC
421   ACCGAGAACAAGAACAAACTGTGGTGATCCCCTGCCGAGGGTCGATTTCAAACCTCAAT
481   GTGTCTCTTTGCGCTAGGTATCCAGAAAAGAGATTTGTTCCGGATGGAAACAGAATTTCC
541   TGGGACAGCGAGATAGGCTTTACTCTCCCCAGTTACATGATCAGCTATGCCGGCATGGTC
601   TTCTGTGAGGCAAAGATCAATGATGAAACCTATCAGTCTATCATGTACATAGTTGTGGTT
661   GTAGGATATAGGATTTATGATGTGATTCTGAGCCCCCCGCATGAAATTGAGCTATCTGCC
721   GGAGAAAAACTTGTCTTAAATTGTACAGCGAGAACAGAGCTCAATGTGGGGCTTGATTTC
781   ACCTGGCACTCTCCACCTTCAAAGTCTCATCATAAGAAGATTGTAAACCGGGATGTGAAA
841   CCCTTTCCTGGGACTGTGGCGAAGATGTTTTTGAGCACCTTGACAATAGAAAGTGTGACC
901   AAGAGTGACCAAGGGGAATACACCTGTGTAGCGTCCAGTGGACGGATGATCAAGAGAAAT
961   AGAACATTTGTCCGAGTTCACACAAAGCCTTTTATTGCTTTCGGTAGTGCTCGAGGGACT
1021  AGTGAAAAAAAGGAGCTGAGGAAAGTGGCCCATTTAACAGGCAAGTCCAACTCAAGGTCC
1081  ATGCCTCTGGAATGGGAAGACACCTATGGAATTGTCCTGCTTTCTGGAGTGAAGTATAAG
1141  AAGGGTGGCCTTGTGATCAATGAAACTGGGCTGTACTTTGTATATTCCAAAGTATACTTC
1201  CGGGGTCAATCTTGCAACAACCTGCCCCTGAGCCACAAGGTCTACATGAGGAACTCTAAG
1261  TATCCCCAGGATCTGGTGATGATGGAGGGGAAGATGATGAGCTACTGCACTACTGGGCAG
1321  ATGTGGGCCCGCAGCAGCTACCTGGGGGCAGTGTTCAATCTTACCAGTGCTGATCATTTA
1381  TATGTCAACGTATCTGAGCTCTCTCTGGTCAATTTTGAGGAATCTCAGACGTTTTTCGGC
1441  TTATATAAGCTCTAA
</pre>

FIG. 7

1     MESKALLAVALWFCVETRAASVGLPGDFLHPPKLSTQKDILTILANTTLQITCRGQRDLD
61    WLWPNAQRDSEERVLVTECGGGDSIFCKTLTIPRVVGNDTGAYKCSYRDVDIASTVYVYV
121   RDYRSPFIASVSDQHGIVYITENKNKTVVIPCRGSISNLNVSLCARYPEKRFVPDGNRIS
181   WDSEIGFTLPSYMISYAGMVFCEAKINDETYQSIMYIVVVGYRIYDVILSPPHEIELSA
241   GEKLVLNCTARTELNVGLDFTWHSPPSKSHHKKIVNRDVKPFPGTVAKMFLSTLTIESVT
301   KSDQGEYTCVASSGRMIKRNRTFVRVHTKPFIAFGSARGTSEKKELRKVAHLTGKSNSRS
361   MPLEWEDTYGIVLLSGVKYKKGGLVINETGLYFVYSKVYFRGQSCNNLPLSHKVYMRNSK
421   YPQDLVMMEGKMMSYCTTGQMWARSSYLGAVFNLTSADHLYVNVSELSLVNFEESQTFFG
481   LYKL

FIG. 8

```
1    ATGTCTGCACTTCTGATCCTAGCTCTTGTTGGAGCTGCAGTTGCTGACTACAAAGACGAT
61   GACGACAAGCTTGCGGCCGCCAGTGATACAGGTAGACCTTTCGTAGAGATGTACAGTGAA
121  ATCCCCGAAATTATACACATGACTGAAGGAAGGGAGCTCGTCATTCCCTGCCGGGTTACG
181  TCACCTAACATCACTGTTACTTTAAAAAAGTTTCCACTTGACACTTTGATCCCTGATGGA
241  AAACGCATAATCTGGGACAGTAGAAAGGGCTTCATCATATCAAATGCAACGTACAAAGAA
301  ATAGGGCTTCTGACCTGTGAAGCAACAGTCAATGGGCATTTGTATAAGACAAACTATCTC
361  ACACATCGACAAACCAATACAATCATAGCTCGAGGGACTAGTGAAAAAAAGGAGCTGAGG
421  AAAGTGGCCCATTTAACAGGCAAGTCCAACTCAAGGTCCATGCCTCTGGAATGGGAAGAC
481  ACCTATGGAATTGTCCTGCTTTCTGGAGTGAAGTATAAGAAGGGTGGCCTTGTGATCAAT
541  GAAACTGGGCTGTACTTTGTATATTCCAAAGTATACTTCCGGGGTCAATCTTGCAACAAC
601  CTGCCCCTGAGCCACAAGGTCTACATGAGGAACTCTAAGTATCCCCAGGATCTGGTGATG
661  ATGGAGGGGAAGATGATGAGCTACTGCACTACTGGGCAGATGTGGGCCCGCAGCAGCTAC
721  CTGGGGGCAGTGTTCAATCTTACCAGTGCTGATCATTTATATGTCAACGTATCTGAGCTC
781  TCTCTGGTCAATTTTGAGGAATCTCAGACGTTTTTCGGCTTATATAAGCTCTAA
```

FIG. 9

```
1    SDTGRPFVEMYSEIPEIIHMTEGRELVIPCRVTSPNITVTLKKFPLDTLIPDGKRIIWDS
61   RKGFIISNATYKEIGLLTCEATVNGHLYKTNYLTHRQTNTII
```

FIG. 10

VEGF-ACTIVATED TRAIL LIGANDS

CROSS-REFERENCES TO RELATED APPLICATIONS

This application is a continuation of U.S. application Ser. No. 12/063,897, filed Feb. 15, 2008, which is the U.S. National Stage entry of International Application No. PCT/US2006/031991, filed Aug. 15, 2006, which claims the benefit of U.S. provisional application Ser. No. 60/708,723, filed Aug. 15, 2005, the disclosures of which are incorporated herein by reference in their entirety.

STATEMENT AS TO RIGHTS TO INVENTIONS MADE UNDER FEDERALLY SPONSORED RESEARCH AND DEVELOPMENT

This invention was made with government support under DAMD17-02-1-0029 awarded by the Prostate Cancer Research Program of the Department of Defense and under W81XWH-04-1-0745 BC032859 awarded by the Breast Cancer Research Program of the Department of Defense. The government has certain rights in this invention.

REFERENCE TO SEQUENCE LISTING

This application includes a Sequence Listing as a text file named "81906-164120US-855258_SEQLIST.txt" created Oct. 18, 2012, and containing 135,168 bytes. The material contained in this text file is incorporated by reference in its entirety for all purposes.

FIELD OF THE INVENTION

The present invention relates compositions and methods useful for treating diseases and disorders, including cancers, related to unregulated angiogenesis and/or vasculogenesis. More specifically, the present invention provides fusion proteins comprising an extracellular domain of a VEGF receptor and a death ligand useful for treatment of cancers and disorders such as rheumatoid arthritis, macular degeneration and psoriasis.

BACKGROUND OF THE INVENTION

Angiogenesis is the process of developing new blood vessels that involves the proliferation, migration and tissue infiltration of capillary endothelial cells from pre-existing blood vessels. Angiogenesis is important in normal physiological processes including embryonic development, follicular growth, and wound healing as well as in pathological conditions involving tumor growth and non-neoplastic diseases involving abnormal neovascularization, including neovascular glaucoma (Folkman and Klagsbrun, Science (1987), 235: 442-447).

The link between angiogenesis and cancer is well established. Neovascularization is an important step in the transition from hyperplasia to neoplasia and it must occur for tumors to grow beyond 2-3 mm in diameter and for tumor metastasis (Folkman, Nat Med (1995), 1:27-30; reviewed in Bouck et al., Adv in Cancer Res (1996), 69:135-174). A correlation between microvessel density and severity of disease has been observed in a number of different tumor types including malignant glioma (Plate & Risau, GLIA (1995), 15:339-347), and breast (Horak et al., Lancet (1992), 340: 1120-124), bladder (Dickinson et al., Br J Urol (1994), 74:762-766), colon (Takahashi et al., Cancer Res (1995), 55:3964-3968), and endometrial cancer (Kirschner et al., Am J Obstet Gynecol (1996), 174:1879-1882).

Other than cancer, a number of serious diseases are associated with persistent, unregulated angiogenesis. These diseases are dominated by abnormal neovascularization. Included in the diseases in which unregulated angiogenesis is present are endometriosis, ocular disease (e.g., macular degeneration), psoiaris, and rheumatoid arthritis. Arthritis is a serious health care problem. Progressive arthritic conditions in humans cause severe pain, loss of joint mobility and disfigurement, and an overall reduction in the quality of life. In rheumatoid arthritis, the synovium hyperproliferates (aided by new blood vessels) and invades the cartilage which is destroyed.

Suppression of angiogenesis would inhibit the formation of new vessels and therefore affect tumor growth and generation of metastases. Indeed, it has been estimated that the elimination of a single endothelial cell could inhibit the growth of 100 tumor cells (Thorpe et al., Breast Cancer Research and Treatment (1995), 36:237-251). Inhibition of new capillary formation could lessen the joint destruction that occurs in rheumatoid arthritis and halt disease progression.

So far, several angiogenic factors have been identified (reviewed in Folkman, Nat Med (1995), 1:27-30; Hanahan et al., Cell (1996), 86:353-364), including the particularly potent vascular endothelial growth factor (VEGF), also known as VPF or vasculotropin (reviewed in Ferrara, Trends Cardiovasc Med (1993), 3:244-250; Ferrara and Davis-Smyth, Endocrine Rev (1997), 18:4-25). Unlike other angiogenic factors, VEGF acts as an endothelial cell-specific mitogen during angiogenesis (Terman et al., Biochem Biophys Res Commun (1992), 187:1579-1586 and Ferrara, Trends Cardiovasc Med (1993), 3:244-250). Antibodies raised against VEGF have been shown to suppress tumor growth in vivo (Kim et al., Nature (1993), 362:841-844), indicating that VEGF antagonists could have therapeutic applications as inhibitors of tumor-induced angiogenesis.

VEGF is secreted and by a number of human tumor cell lines in culture, including glioma (Tsai et al., J Neurosurg (1995), 82:864-867), melanoma (Claffey et al., Cancer Res (1996), 56:172-181), gastric cancer cells (Zhang et al., World J Gastroenterol (2002), 8 (6):994-8), Kaposi sarcoma, and epidermoid carcinoma cells (Myoken et al., Proc Natl Acad Sci USA (1991), 88:5819-5823). More importantly, VEGF transcripts or protein has been identified by in situ hybridization or immunohistochemistry in primary gliomas (Plate, et al., Lab Invest (1992), 67:529-534; Plate et al., Int J Cancer (1994), 59:520-529), hemangioblastomas (Hatva et al., Amer J Pathol (1996), 148:763-775) and breast (Toi et al., Jpn. J. Cancer Res (1994), 85:1045-1049; Anan et al., Surgery (1996), 119:333-339; Yoshiji et al., Cancer Res (1996), 56:2013-2016), colon (Brown et al., Cancer Res (1993), 53:4727-4735; Takahashi et al., Cancer Res (1995), 55:3964-3968) and renal cell tumors (Takahashi et al., Cancer Res (1994), 54:4233-4237). In glioblastoma, the message for VEGF is found in cells adjacent to necrotic regions which is consistent with upregulation by hypoxia (Shweiki et al., Nature (1992), 359, 843-845; Plate et al., Lab Invest (1992), 67:529-534). A marked increase of VEGF mRNA and protein was reported in pituitary tumors (McCabe et al., J Clin Endocrinol Metab (2002), 87 (9):4238-44) and in melanoma xenografts (Graells et al., J Invest Dermatol (2004), 123 (6):1151-61). Furthermore, patients with cancer have significantly higher serum VEGF levels than normal volunteers. The highest VEGF concentrations were observed in patients with untreated metastatic cancers.

VEGF was purified initially from the conditioned media of folliculostellate cells and from a variety of tumor cell lines (Ferrara et al., *Biochem Biophys Res Commun* (1989), 161: 851-858; Plouet et al., *EMBO J* (1989), 8:3801-3806). VEGF is a homodimeric glycoprotein consisting of two 23 kD subunits and typically binds as a dimeric polypeptide to its receptors. The human gene encoding VEGF is organized into eight exons, separated by seven introns. Alternative splicing of mRNAs for the VEGF gene results in the generation of five different molecular species, having 121, 145, 165, 189, or 206 amino acid residues in the mature monomer (Tisher et al., *J Biol Chem* (1991), 266:11947-11954; Houck et al., *Mol Endocrinol* (1991), 5:1806-1814. Only $VEGF_{165}$, which lacks the residues encoded by exon 6, is the mature and active form of VEGF. It binds to heparin and cell surface heparin sulfate proteoglycans, and can be expressed as a free or as a cell membrane bound form (Houck et al., 1992). $VEGF_{206}$ and $VEGF_{189}$ are membrane bound forms. Also, recently, a number of VEGF structural homologs have been identified: VEGF-B, VEGF-C, VEGF-D and placenta growth factor (PlGF) (Klagsbrun and D'Amore, *Cytokine Growth Factor Rev* (1996), 7:259-270; reviewed in Ferrara, *J Mol Med* (1999), 77:527-543).

Two tyrosine kinase receptors have been identified for which VEGF acts as a high affinity ligand: a fms-like tyrosine kinase-1 (Flt-1 or VEGFR-1) and a kinase domain receptor (KDR/Flk-1 or VEGFR-2) (Matthews et al., *Proc Natl Acad Sci USA* (1991), 88:9026-9030; Terman et al., *Biochem Biophys Res Commun* (1992), 187:1579-1586; De Vries et al., *Science* (1992), 255:989-991; Millauer et al., *Cell* (1993), 72:835-846). Although Flt-1 binds VEGF with 50-fold higher affinity than KDR (De Vries et al., *Science* (1992), 255:989-991), most of the VEGF angiogenic properties (mitogenicity, chemotaxis, and induction on morphological changes) are mediated by interaction with KDR (Waltenberger et al., *J Biol Chem* (1994), 269:26988-26995). Therefore, the interaction between VEGF and KDR is the most appropriate to interrupt in order to inhibit angiogenesis.

VEGF receptors typically are class III receptor-type tyrosine kinases characterized by having several, typically 5 or 7, immunoglobulin-like loops in their amino-terminal extracellular receptor ligand-binding domains (Kaipainen et al., *J Exp Med* (1993), 178:2077-2088). The other two regions include a transmembrane region and a carboxy-terminal intracellular catalytic domain interrupted by insertion of hydrophilic interkinase sequences of variable lengths, called the kinase insert domain (Terman et al., *Oncogene* (1991), 6:1677-1683).

In addition, VEGF binds to a third receptor, neuropilin-1. Neuropilin-1 (NRP-1) was first described as a co-receptor implicated in neuronal guidance that bound members of the semaphorin/collapsin family. NRP-1 is also expressed in endothelial cells and is believed to promote angiogenesis by acting as a co-receptor with VEGFR-2 (Gray et al., *Cancer Res*, (2005), 65 (9):3664-70). NRP-1 and VEGFR-2 do not interact directly, but are bridged by one VEGF isoform, $VEGF_{165}$ (Mac Gabhann and Popel, *Am J Physiol Heart Circ Physiol*, (2005), 288 (6):H2851-60).

Thus, VEGF may play a broad role in a range of cancers, including cancers of the colon, rectum, renal cell (kidney), breast, non-small cell lung and ovary. Currently, Avastatin™ (bevacizumab), a therapeutic antibody developed by Genentech designed to inhibit VEGF function and thereby interfering with the blood supply to tumors has been approved as treatment for patients with metastatic cancer of the colon or rectum. Other approaches to block angiogenesis employ monoclonal antibodies specific to VEGF receptors (e.g., U.S. Pat. No. 5,955,331), compounds such as indolinone (U.S. Pat. No. 6,846,839) or peptides interacting with VEGF and thus blocking its interaction with its cognate receptor (e.g., U.S. Pat. No. 6,559,126).

However, none of the treatment options currently in clinical trials or known in the prior that block tumor-associated neovascularization by preventing VEGF binding to its cognate receptor on tumor cells, do also attempt to kill the tumor cells. This may not an easy task because, in addition to its major role in angiogenesis, VEGF affects cell survival by interfering with apoptosis (Bairey et al., *Leuk Res* (2004), 28 (3):243-8).

Apoptosis, or programmed cell death, is an important physiological process in multicellular organisms, both during development and for homeostasis. Apoptosis is mediated, at least in part, by a cell surface receptor protein, Fas, which plays an important role in the development and function of the immune system. Malfunction of the Fas system has been shown to cause lymphoproliferative disorders and accelerate autoimmune disorders. (Takahashi et al., *Cell* (1994), 76:969-976).

Fas is a type I membrane protein with a molecular weight of about 45 kD that belongs to the tumor necrosis factor (TNF) receptor family (Nagata et al., *Science*, 1995), 267: 1449). Fas transduces apoptotic signal to the cell as a cell surface antigen. Apoptotic cell death is characterized by nuclear and cytoplasmic shrinkage, membrane blebbing, and degradation of chromosomal DNA in a characteristic pattern, and can be distinguished from necrotic cell death due to acute cellular injury.

Many tissues and cell lines weakly express Fas, but abundant expression is found in the heart, lung, liver, ovary and thymus (Watanabe-Fukunaga et al., *J Immunol* (1992), 148: 1274). Fas transmits a signal for apoptosis or programmed cell death (Thompson, *Science* (1995), 267:1456) when it is triggered by binding of certain antibodies such as APO-1 (Trauth et al., *Science* (1989), 245:301) and anti-Fas (Yonehara et al., *J Exp Med* (1989), 169:1747) or the natural ligand for Fas, Fas Ligand (FasL). Fas is also expressed on the surface of tumor cells. For example, the efficiency of the induction of Fas-mediated apoptosis by anti-Fas antibodies, FasL expressing cells or recombinant FasL in tumors has been demonstrated in vivo in solid tumors implanted in mice (Timmer et al., *J Pathol* (2002), 196 (2):125-34).

Human, rat, and mouse FasL have been cloned (Takahashi et al., *Internat Immunol* (1994), 6:1567; Suda et al., *Cell* (1993), 75:1169; Lynch et al., *Immunity* (1994), 1:131; Takahashi et al., *Cell* (1994), 76:969). Human FasL is highly homologous to rat FasL and mouse FasL in its extracellular domain, and human FasL is capable of recognizing not only the human Fas but also the mouse Fas, and induces apoptosis. Similarly, rat and mouse FasL are capable of recognizing the human Fas and inducing apoptosis. FasL is a type II membrane protein, i.e, having an extracellular carboxyl-terminal domain and an intracellular amino-terminal domain, belongs to the TNF family of proteins and has a molecular weight of about 40 kD. (Suda et al., *Cell* (1993), 75:1169). The Fas ligand is strongly expressed on activated lymphocytes, in the testis (Suda et al., *Cell* (1993), 75:1169) and the eye (Griffith, et al., *Science* (1995), 270:1189), as well as on some cytotoxic T-lymphocyte (CTL) cell lines (Rouvier et al., *J Exp Med* (1993), 177:195).

Cells expressing FasL, as well as purified FasL protein (Suda and Nagata, J Exp Med (1994), 179:873), are cytotoxic for cells expressing Fas. Thus, FasL transmits a signal for apoptosis by binding to Fas. Also by analogy with TNF, FasL is believed to function as a trimer and presumably binds one to three Fas molecules at the interface of respective FasL units. Binding of two or more Fas molecules to a FasL trimer presumably causes oligomerization of Fas, which transmits an apoptotic signal to the Pas-expressing cell.

It would generally be desirable to be able to produce a soluble compound that combines (i) the function of a VEGFR polypeptide, i.e., binding a VEGF polypeptide, (ii) neutralizing VEGF-mediated activation of a VEGFR and thus, preventing tumor-associated neovascularization and (iii) the function of a Fas ligand in its interactions with the Fas receptor, i.e., receptor binding and/or activation of receptor mediated pathways. Such a compound would be useful for killing cancer cells that secrete VEGF and express Fas. However, a significant challenge in the recombinant protein technology has often been the expression of biologically active proteins of a transmembrane protein in the form of a soluble protein. The present invention overcomes these obstacles and meets those and other needs.

BRIEF SUMMARY OF THE INVENTION

The present invention provides novel fusion proteins that bind to a death receptor. A fusion protein of the present invention comprises (i) a vascular endothelial growth factor receptor (VEGFR) polypeptide that binds a vascular endothelial factor (VEGF) polypeptide and (ii) a death ligand comprising an oligomerization domain and a death receptor recognition moiety, wherein the C-terminus of the VEGFR polypeptide is linked to the N-terminus of the death ligand.

The VEGFR-death ligand fusion proteins are useful for methods of neutralizing VEGF activation of VEGF receptors. These methods are particularly useful for inducing apoptosis, inducing cytotoxic effects in cells, treating cancer and diseases or disorders related to unregulated angiogenesis and/or vasculogenesis.

In a preferred embodiment of the invention, the death receptor is Fas and the death ligand is a Fas ligand. Preferably the Fas ligand is a human Fas ligand.

In another preferred embodiments of the invention, the VEGFR polypeptide of the fusion protein comprises a VEGF binding domain of VEGF receptor-1 (VEGFR-1) or a VEGF binding domain of VEGF receptor-2 (VEGFR-2). VEGFR-1 and VEGFR-2 preferably are human VEGFR-1 and human VEGFR-2. VEGFR-1 and VEGFR-2 can also be from mouse or rat.

A preferred fusion protein of the invention comprises a murine VEGFR-2 polypeptide and a human Fas ligand. Preferably this fusion protein comprises an amino acid sequence which has at least 80% homology to the amino acid sequence shown in SEQ ID NO:22 or SEQ ID NO:23. In one embodiment of the present invention, the fusion protein comprises the amino acid sequence shown in SEQ ID NO:22 or SEQ ID NO:23.

In some embodiments, a fusion protein of the invention further comprises an epitope tag. Preferred epitope tags are a FLAG-like tag or an HA tag. Preferably, the epitope tag can be cleaved off.

Several Fas ligand polypeptides can be linked to a VEGFR polypeptide. In a preferred embodiment, the Fas ligand is selected from the group consisting of (i) a polypeptide comprising the amino acid sequence of SEQ ID NO: 11; (ii) a polypeptide comprising the amino acid sequence of SEQ ID NO: 12; (iii) a polypeptide comprising the amino acid sequence of SEQ ID NO:13; and (iv) a polypeptide having Fas-binding activity comprising an amino acid sequence wherein one to several amino acid residues have been deleted, substituted, or added in the amino acid sequence of any one of (i) to (iii).

Several VEGFR-1 polypeptides can be linked to a Fas ligand. In a preferred embodiment, the VEGFR-1 polypeptide is selected from the group consisting of (i) a polypeptide comprising the amino acid sequence of SEQ ID NO:20; (ii) a polypeptide comprising amino acid residues 1 to 747 of SEQ ID NO:19; (iii) a polypeptide comprising amino acid residues 32 to 747 of SEQ ID NO:19; (iv) a polypeptide comprising amino acid residues 151 to 214 of SEQ ID NO:19; (v) a polypeptide comprising amino acid residues 230 to 327 of SEQ ID NO:19; (vi) a polypeptide comprising amino acids 129 to 230 of VEGFR1 SDTGRPFVEMYSEIPEIIHMTE-GRELVIPCRVTSPNITVTLKKFPLDTLIPDGKRIIWDSR KGFIISNATYKEIGLLTCEATVNGHLYK-TNYLTHRQTNTII (SEQ ID NO:55) as shown in FIG. 10; domain 2 (D2)), and (vii) a polypeptide having VEGF binding activity comprising an amino acid sequence wherein one to several amino acid residues have been deleted, substituted, or added in the amino acid sequence of any one of (i) to (vi).

Several VEGFR-2 polypeptides can be linked to a Fas ligand. In a preferred embodiment, the VEGFR-2 polypeptide is selected from the group consisting of (i) a polypeptide comprising the amino acid sequence of SEQ ID NO:1; (ii) a polypeptide comprising the amino acid sequence of SEQ ID NO:2; (iii) a polypeptide comprising the amino acid sequence of SEQ ID NO:3; (iv) a polypeptide comprising the amino acid sequence of SEQ ID NO:4; (v) a polypeptide comprising the amino acid sequence of SEQ ID NO:5; (vi) a polypeptide comprising the amino acid sequence of SEQ ID NO:6; (iiv) a polypeptide comprising amino acids 141 to 207 of the amino acid sequence of SEQ ID NO:1; (iix) a polypeptide comprising amino acids 224 to 320 of the amino acid sequence of SEQ ID NO:1; and (ix) a polypeptide having VEGF binding activity comprising an amino acid sequence wherein one to several amino acid residues have been deleted, substituted, or added in the amino acid sequence of any one of (i) to (iix).

In another aspect of the invention, nucleic acids encoding the fusion proteins of the invention are provided. A preferred nucleic acid is shown in SEQ ID NO:14. Further, the invention provides vectors comprising the nucleic acid encoding a fusion protein of the invention. A preferred vector comprises a nucleic acid comprising the nucleotide sequence of SEQ ID NO:14.

The invention also provides a method of modulating a death receptor-mediated pathway. This method comprises the step of contacting a death receptor expressing cell with a fusion protein comprising (i) a VEGFR polypeptide that binds a VEGF protein; and (ii) a death ligand comprising an oligomerization domain and a death receptor recognition moiety; wherein the VEGFR polypeptide has bound a VEGF protein and wherein the amount of the fusion protein is effective to modulate the death receptor-mediated pathway.

In a preferred embodiment of the present invention, the Fas-mediated pathway is apoptosis. In this method, the amount of the fusion protein is effective to induce apoptosis.

Methods of the present invention can be practiced in vitro and in vivo.

In a preferred embodiment of the present invention, the death receptor expressing cell is a cancer cell, preferably a cancer cell that overexpresses VEGF. The cancer cell is selected from the group consisting of breast cancer, prostate cancer, colon cancer, lung cancer, glioblastoma, and ovarian cancer.

In another preferred embodiment of the present invention, the Fas-mediated pathway is modulated in a disease other than cancer. A preferred disease is selected from the group consisting of rheumatoid arthritis, psoriasis, and macular degeneration.

In a preferred embodiment of the present invention, the method of modulating a death receptor-mediated pathway comprises the step of contacting the death receptor expressing cell with a chemotherapeutic agent. Preferred chemotherapeutic agent are selected from the group consisting of camptothecin, etoposide, bisindolylmaleimide VIII, cisplatin, taxol, doxorubicin, temozolomide, bortezomid, LY294002, and valproic acid.

This invention also provides pharmaceutical compositions comprising a fusion protein of the present invention and a pharmaceutically acceptable excipient, carrier and/or diluent.

In another aspect this invention provides a composition comprising a vector comprising a nucleic acid having a nucleotide sequence as shown in SEQ ID NO: 14 and a pharmaceutically acceptable excipient, carrier and/or diluent.

BRIEF DESCRIPTION OF THE DRAWINGS

FIG. 2 shows an alignment of FasL protein sequences from human (H; SEQ ID NO:8) (GenBank Accession No. P48023), mouse (M; SEQ ID NO:9) (GenBank Accession No. A53062) and rat (R; SEQ ID NO:10) (GenBank Accession No. A49266). Identical amino acid residues of mouse and rat FasL to human FasL are indicated by asterisks. Intracellular domain, transmembrane domain, cleavage position, trimerization domain and Receptor binding domains are indicated. The N-terminal border of the FasL-Fas binding domain has not yet been elucidated.

FIG. 3 shows an alignment of extracellular and transmembrane regions of VEGFR-2 protein sequences from human (SEQ ID NO:26) (GenBank Accession No. NP-002244), mouse (SEQ ID NO:27) (GenBank Accession No. P35918) and rat (SEQ ID NO:28) (GenBank Accession No. NP_037194) with human VEGFR-1 (SEQ ID NO:29) (GenBank Accession No. NM_002019). Identical amino acid residues of mouse and rat VEGFR-2 to human VEGFR-2 are indicated by asterisks. Signal sequence, IgG-like domains 1 to 7, and transmembrane domain are indicated for the VEGFR-2 sequences.

FIG. 4 shows an annotated sequence of the extracellular domain of human neuropilin-1 (SEQ ID NO:30) (part of Genbank AAC12921). Domains identified are indicated. The B domain is involved in binding VEGF.

FIG. 7 shows a cDNA sequence of FlkFasL (SEQ ID NO:14). The nucleotide sequence for Flk-1 signal sequence and extracellular domain sequence is underlined; the nucleotide sequence of a linker is shown in normal font; and the nucleotide sequence of FasL is shown in bold.

FIG. 8 shows an amino acid sequence of FlkFasL (SEQ ID NO:22). The amino acid sequence for the Flk-1 signal peptide is shown in italics; the amino acid sequence for the Flk-1 extracellular domain is underlined; the amino acid sequence of a linker is shown in normal font; and the amino acid sequence of FasL is shown in bold.

FIG. 9 shows the nucleic acid sequence of FLAG-tagged R1[D2]FasL (SEQ ID NO:54). Italics, preprotrypsin leader sequence; underlined, FLAG epitope tag sequence; underlined and bold, VEGFR1 domain 2; standard font, ARGTS (SEQ ID NO:7) encoding linker sequence; bold, FasL trimerization and Fas receptor binding domains. Details are described in Example 3.

FIG. 10 shows the amino acid sequence of R1[D2] (SEQ ID NO:55) using the single letter code for amino acid residues. Details are described in Example 3.

DETAILED DESCRIPTION OF THE INVENTION

I. Definitions

Figure 1:
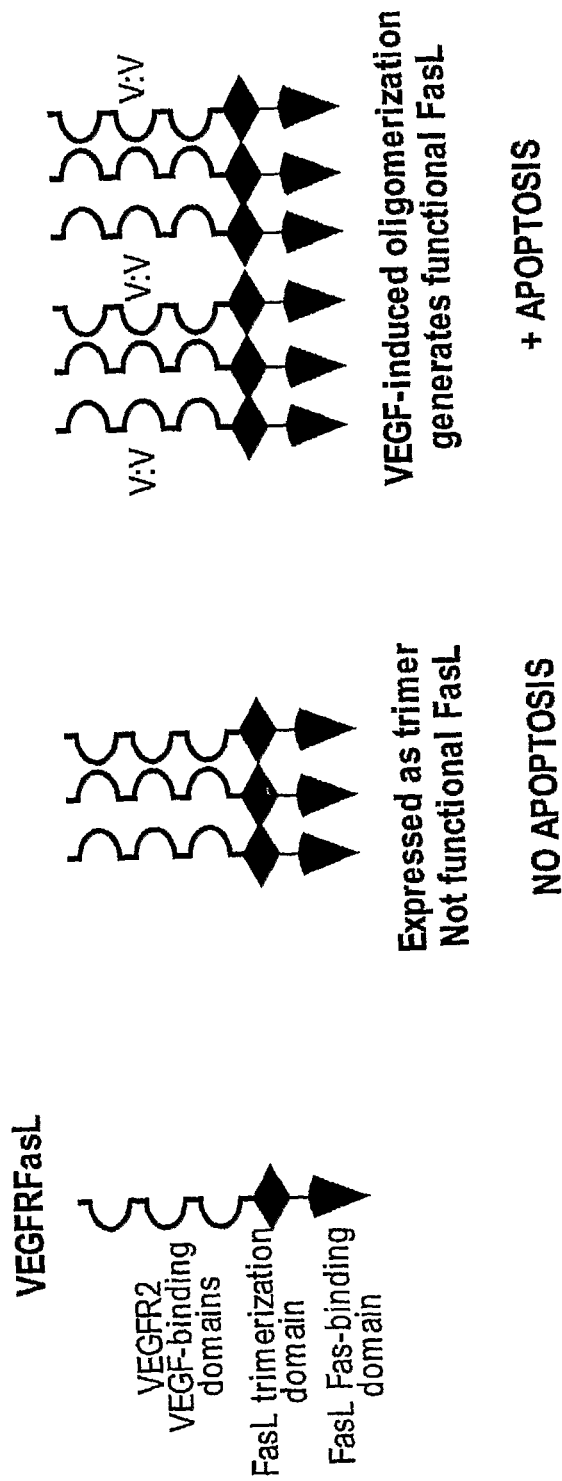
FIG. 1 shows schematic drawings of fusion proteins of the invention as exemplified by a VEGFR-FasL. The figure shows (i) a monomeric fusion protein, (ii) a trimeric fusion protein in the absence of VEGF generating a nonfunctional FasL not capable of inducing significant apoptosis and (iii) a VEGF-induced oligomerization of fusion proteins generating functional FasL capable of inducing apoptosis. V:V indicates binding of two VEGF molecules.
Figure 5:
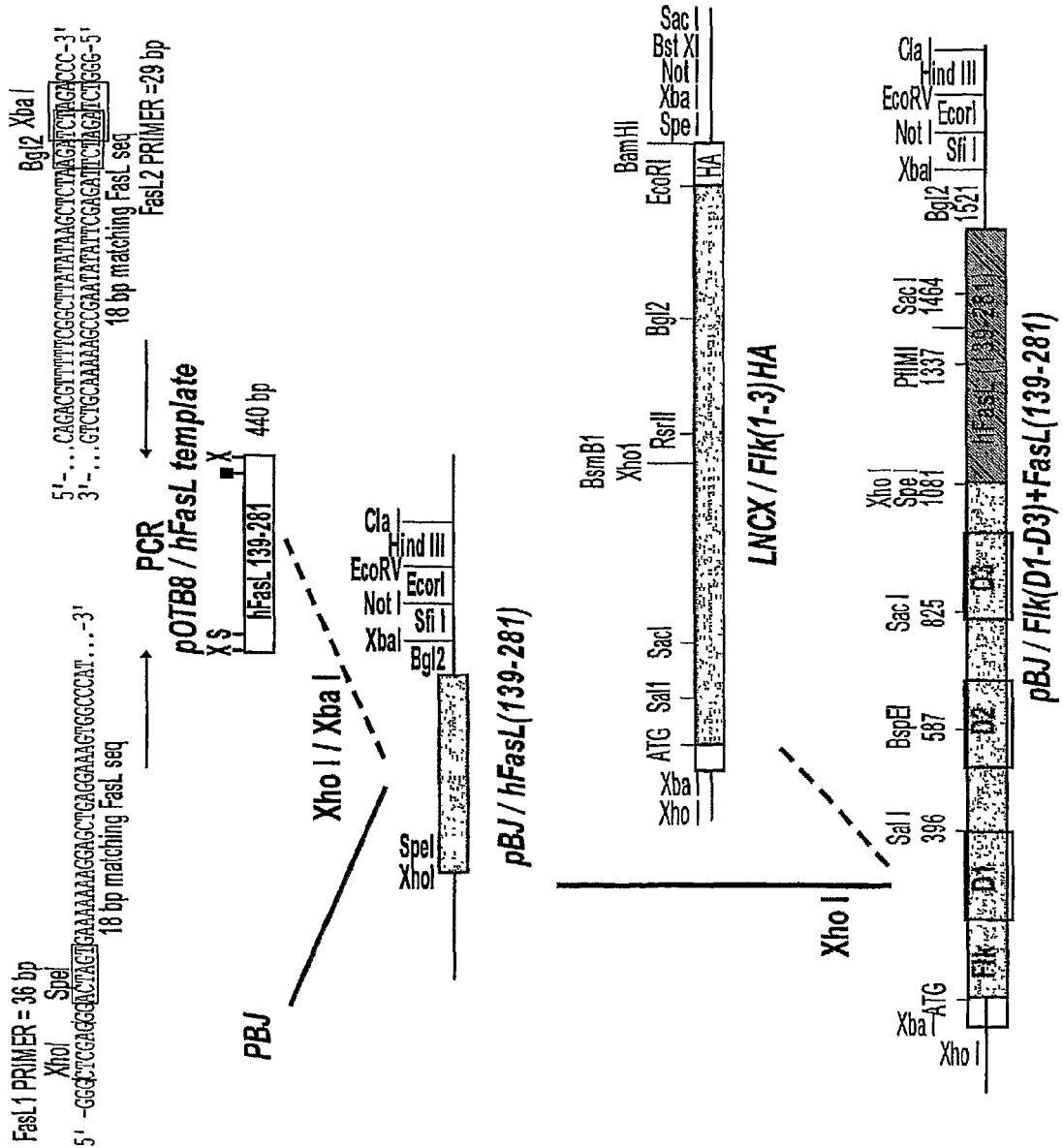
FIG. 5 depicts the construction of a VEGFR/FasL fusion protein encoding nucleic acid, Flk(D1-D3)+FasL(139-281). FasL1 Primer=SEQ ID NO:31; FasL2 Primer=SEQ ID NO:32. Details are described in Example 2.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analog" refers to a compound that has the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. "Amino acid mimetic" refers to a chemical compound that has a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Biological sample" as used herein is a sample of biological tissue or fluid that contains nucleic acids or polypeptides. Such samples are typically from humans, but include tissues isolated from non-human primates, or rodents, e.g., mice, and rats. Biological samples may also include sections of tissues such as biopsy and autopsy samples, frozen sections taken for histological purposes, blood, plasma, serum, sputum, stool, tears, mucus, hair, skin, etc. Biological samples also include explants and primary and/or transformed cell cultures derived from patient tissues. A "biological sample" also refers to a cell or population of cells or a quantity of tissue or fluid from an animal. Most often, the biological sample has been removed from an animal, but the term "biological sample" can also refer to cells or tissue analyzed in vivo, i.e., without removal from the animal. Typically, a "biological sample" will contain cells from the animal, but the term can also refer to noncellular biological material, such as noncellular fractions of blood, saliva, or urine, that can be used to measure cancer-associated polynucleotide or polypeptide levels. Numerous types of biological samples can be used in the present invention, including, but not limited to, a tissue biopsy, a blood sample, a serum sample, or a saliva sample. As used herein, a "tissue biopsy" refers to an amount of tissue removed from an animal, preferably a human, for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc.

"Providing a biological sample" means to obtain a biological sample for use in methods described in this invention. Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, are also useful.

The phrase "changes in cell growth" refers to any change in cell growth and proliferation characteristics in vitro or in vivo, such as formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, *Culture of Animal Cells a Manual of Basic Technique* pp. 231-241 ($3^{rd}$ ed. 1994).

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences.

Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, an often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy (see, Freshney, *Culture of Animal Cells a Manual of Basic Technique* (3rd ed. 1994)).

The term "death ligand" refers to a family of mammalian proteins that can bind to a death receptor and upon binding induce cell killing. Exemplary death ligands include, but are not limited to, FasL, tumor necrosis factor (TNF), lymphotoxin (LT) and tumor necrosis factor-related apoptosis-inducing ligand (TRAIL). Typically, a death ligand polypeptide comprises an oligomerization domain and a death receptor recognition moiety.

The term "death receptor" refers to a family of mammalian proteins expressed on the surface of a mammalian cell that can bind a death ligand and upon binding of the death ligand oligomerize and induce cell killing. Typically, a death receptor polypeptide comprises an oligomerization domain and a death ligand recognition moiety. Eight death receptors and death receptor signaling are reviewed by Lavrik et al., *J Cell Sci*, (2005), 118 (Pt2):265-7, hereby incorporated by reference in its entirety. Exemplary death receptors include, but are not limited to, tumor necrosis factor receptor 1 (TNFR1; also known as DR1, CD120a, p55 and p60), CD95 (also known as DR2, APO-1 and Fas), DR3 (also known as APO-3, LARD, TRAMP and WSL1), TNF-related apoptosis-inducing ligand receptor 1 (TRAILR1; also known as DR4 and APO-2), TRAILR2 (also known as DR5, KILLER and TRICK2), DR6, ectodysplasin A receptor (EDAR) and nerve growth factor receptor (NGFR). These are distinguished by a cytoplasmic region of ~80 residues termed the death domain (DD). When these receptors are triggered by corresponding ligands, a number of molecules are recruited to the DD and subsequently a signaling cascade is activated. Death ligands also interact with decoy receptors (DcRs) that do not possess DDs and so cannot form signaling complexes. To date, four decoy receptors have been characterized: TRAILR3 (also known as DcR1), TRAILR4 (also known as DcR2), DcR3 and osteoprotegrin (OPG).

The term "death receptor recognition moiety" refers to a subdomain of a death ligand necessary and sufficient for binding to a death receptor.

By "determining the functional effect" is meant assaying for a compound that increases or decreases a parameter that is indirectly or directly under the influence of a fusion protein of this invention such as a VEGFR-FasL, e.g., functional, enzymatic, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties for the protein, measuring inducible markers or transcriptional activation of the a fusion protein of this invention such as a VEGFR-FasL; measuring binding activity, e.g., binding to a death receptor, measuring cellular proliferation, measuring apoptosis, or the like. Determination of the functional effect of a compound on cancer can also be performed using assays known to those of skill in the art such as an in vitro assays, e.g., cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo; mRNA and protein expression in cells undergoing metastasis, and other characteristics of cancer cells. The functional effects can be evaluated by many means known to those skilled in the art, e.g., microscopy for quantitative or qualitative measures of alterations in morphological features, measurement of changes in RNA or protein levels, measurement of RNA stability, identification of downstream or reporter gene expression (CAT, luciferase, (β-gal, GFP and the like), e.g., via chemiluminescence, fluorescence, colorimetric reactions, antibody binding, inducible markers, and ligand binding assays. "Functional effects" include in vitro, in vivo, and ex vivo activities.

An "effective amount" of a compound for treating a disorder is an amount that is sufficient to ameliorate, or in some manner, reduce a symptom or stop or reverse progression of a condition. Amelioration of a symptom of a particular disorder by administration of a particular pharmaceutical composition refers to any lessening, whether permanent or temporary, lasting or transit that can be associated An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The term "FasL" or "Fas ligand" refers to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, or 281 amino acids, to a human FasL sequence shown below; (2) bind to antibodies, e.g., polyclonal antibodies, raised against an immunogen comprising an amino acid sequence shown below, or conservatively modified variants thereof; (3) bind to a FasL binding protein; (4) compete with a naturally occurring Fas ligand binding to a Fas ligand binding protein; (5) induce apoptosis in cells having a membrane-bound FasL binding protein; (6) specifically hybridize under stringent hybridization conditions to a nucleic acid sequence shown below, or conservatively modified variants thereof; (7) have a nucleic acid sequence that has greater than about 90%, preferably greater than about 96%, 97%, 98%, 99%, or higher nucleotide sequence identity, preferably over a region of at least about 100, 200, 300, 400 or more nucleotides, to SEQ ID NO:16 (human FasL); and/or (8) have at least 25, often 50, 75, 100, 125 or 143 contiguous amino acid residues of SEQ ID NO:8 or SEQ ID NO:11 (human FasL). A FasL polypeptide may have oligomerization and death receptor recognition domains as described herein.

A FasL polynucleotide or polypeptide sequence is typically from a human, but may be from other mammals, but not limited to, a non-human primate, a rodent, e.g., a rat, mouse, or hamster; a cow, a pig, a horse, a sheep, or other mammal. Therefore, in some embodiments, a FasL polypeptide and a FasL subdomain polypeptide as described herein can comprise a sequence that corresponds to a human FasL sequence. Thus, exemplary FasL are provided herein and are known in the art. For example, GenBank accession numbers for human FasL polypeptide is P48023. The GenBank accession number for mouse FasL polypeptide, for example, is A53062; and for rat FasL, A49266.

The term "FasL binding protein" refers to a polypeptide to which a FasL binds.

A FasL "homolog" or VEGFR "homolog" refers to a polypeptide that comprises an amino acid sequence similar to that of FasL or VEGFR but does not necessarily possess a similar or identical function as FasL or VEGFR.

A FasL "isoform" or VEGFR "isoform" refers to a variant of FasL or VEGFR, respectively, that is encoded by the same gene, but differs in its pI or MW, or both. Such isoforms can differ in their amino acid composition (e.g., as a result of alternative splicing or limited proteolysis) and in addition, or in the alternative, may arise from differential post-translational modification (e.g., glycosylation, acylation or phosphorylation).

A FasL "ortholog" or VEGFR "ortholog" as used herein refers to a non-human polypeptide that (i) comprises an amino acid sequence similar to that of human FasL or VEGFR and (ii) possess a similar or identical function to that of human FasL or VEGFR.

A FasL "related" polypeptide as used herein refers to a FasL homolog, a FasL isoform, or a FasL ortholog. A VEGFR "related" polypeptide, as used herein, refers to a VEGFR homolog, a VEGFR isoform, or a VEGFR ortholog.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect cells, amphibian cells, or mammalian cells such as Cos cells (e.g., Cos-7), CHO, 293, 3T3, HeLa, and the like (see, e.g., American Type Culture Collection).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from about 20 to about 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv Appl Math* 2:482 (1981), by the homology alignment algorithm of Needleman & Wunsch, *J Mol. Bio.* 48:443 (1970), by the search for similarity method of Pearson & Lipman, *Proc Nat'l Acad Sci USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nucl Acids Res* 25:3389-3402 (1977) and Altschul et al., *J Mol Biol* 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, *Proc Natl Acad Sci USA* 89:10915 (1989)) alignments (B) of 50, expectation (E) of 10, M=5, N=-4, and a comparison of both strands.

The BLAST algorithm also performs a statistical analysis of the similarity between two sequences (see, e.g., Karlin & Altschul, *Proc Natl Acad Sci USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

The terms "inhibit", "inhibiting" or "inhibition" includes any measurable reproducible reduction in the interaction of VEGF and a VEGF receptor, angiogenesis; symptoms of diseases correlated to angiogenesis, or any other activity that VEGF may mediate.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The term "modulate" as used herein in reference to a death receptor signal transduction refers to the ability of a compound to alter the function of the death receptor in vitro and/or in vivo. A compound preferably activates the activity of the death receptor depending on the concentration of the compound.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphosphoroamidite linkages (see, Eckstein, *Oligonucleotides and Analogues: A Practical Approach*, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g. to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage et al., *Tetrahedron* 49 (10):1925 (1993) and references therein; Letsinger, *J Org Chem* 35:3800 (1970); Sprinzl et al., *Eur J Biochem* 81:579 (1977); Letsinger et al., *Nucl Acids Res* 14:3487 (1986); Sawai et al., *Chem Lett* 805 (1984), Letsinger et al., *J Am Chem Soc* 110:4470 (1988); and Pauwels et al., *Chemica Scripta* 26:141 91986)), phosphorothioate (Mag et al., *Nucl Acids Res* 19:1437 (1991); and U.S. Pat. No. 5,644,048), phosphorodithioate (Briu et al., *J. Am. Chem. Soc.* 111:2321 (1989), O methylphosphoroamidite linkages (see, Eckstein, *Oligonucleotides and Analogues: A Practical Approach*, Oxford University Press), and peptide nucleic acid backbones and linkages (see, Egholm, *J Am Chem Soc* 114: 1895 (1992); Meier et al., *Chem Int Ed Engl* 31:1008 (1992); Nielsen, *Nature* 365:566 (1993); Carlsson et al., *Nature* 380: 207 (1996), all of which are incorporated by reference). Other analog nucleic acids include those with positive backbones (Denpcy et al., *Proc Natl Acad Sci USA* 92:6097 (1995); non ionic backbones (U.S. Pat. Nos. 5,386,023, 5,637,684, 5,602, 240, 5,216,141 and 4,469,863; Kiedrowski et al., *Angew. Chem. Intl Ed English* 30:423 (1991); Letsinger et al., *J Am Chem Soc* 110:4470 (1988); Letsinger et al., *Nucleoside & Nucleotide* 13:1597 (1994); Chapters 2 and 3, ASC Symposium Series 580, "*Carbohydrate Modifications in Antisense Research*", Ed. Y. S. Sanghui and P. Dan Cook; Mesmaeker et al., *Bioorganic & Medicinal Chem. Lett* 4:395 (1994); Jeffs et al., *J Biomolecular NMR* 34:17 (1994); *Tetrahedron Lett* 37:743 (1996)) and non ribose backbones, including those described in U.S. Pat. Nos. 5,235,033 and 5,034,506, and Chapters 6 and 7, ASC Symposium Series 580, "*Carbohydrate Modifications in Antisense Research*", Ed. Y. S. Sanghui and P. Dan Cook. Nucleic acids containing one or more carbocyclic sugars are also included within one definition of nucleic acids (see, Jenkins et al., *Chem Soc Rev* pp 169 176 (1995)). Several nucleic acid analogs are described in Rawls, C & E News Jun. 2, 1997 page 35. All of these references are hereby expressly incorporated by reference.

Other analogs include peptide nucleic acids (PNA) which are peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched base pairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g., the individual units of a peptide nucleic acid, each containing a base, are referred to herein as a nucleoside.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the breast cancer nucleic acids, proteins and antibodies at any position. Any method known in the art for conjugating the antibody to the label may be employed, including those methods described by Hunter et al., *Nature* 144:945 (1962); David et al., *Biochemistry* 13:1014 (1974); Pain et al., *J Immunol Meth* 40:219 (1981); and Nygren, *J. Histochem. and Cytochem* 30:407 (1982).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

The terms "polypeptide," "peptide" and "protein" as used refer to a polymer of amino acid residues. The terms also apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. Polypeptides and peptides of the present invention include amino acid polymers having D- and L-isoforms of individual amino acid residues, as well as other amino acid variants. Peptides are distinguished by the number of amino acid residues making up the primary structure of the molecule. For purpose of this invention, typically, peptides are amino acid polymers comprising up to 50 amino acid residues and polypeptides comprise more than 50 amino acid residues.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "psoriasis" as used herein refers to a common chronic, squamous dermatosis with polygenic inheritance and a fluctuating course. Methods of diagnosis are well-known to those in the art. It is a chronic skin disorder characterized by hyperproliferation of the epidermis, inflammation and angiogenesis.

The term "rheumatoid arthritis" as used herein refers to a chronic systemic disease primarily of the joints, usually polyarticular, marked by inflammatory changes in the synovial membranes and articular structures and by muscle atrophy and rarefaction of the bones. Forms of rheumatoid arthritis include, but are not limited to, juvenile, chronic villous, cricoarytenoid, deformans, degenerative, mutilans, and proliferative.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel et al.

As used herein, the terms "treat", "treating", and "treatment" include: (1) preventing a disease, such as cancer, i.e. causing the clinical symptoms of the disease not to develop in a subject that may be predisposed to the disease but does not yet experience any symptoms of the disease; (2) inhibiting the disease, i.e. arresting or reducing the development of the disease or its clinical symptoms; or (3) relieving the disease, i.e. causing regression of the disease or its clinical symptoms. Treatment means any manner in which the symptoms or pathology of a condition, disorder, or disease are ameliorated or otherwise beneficially altered. Treatment also encompasses any pharmaceutical use of the compositions herein. Preferably, the subject in need of such treatment is a mammal, more preferable a human.

"Tumor cell" refers to precancerous, cancerous, and normal cells in a tumor.

"VEGF" refers to any member of the vascular endothelial growth factor family as well as splice variants and isoforms. VEGF can be found as four different splice variants known as $VEGF_{121}$ (or VEGF-121), $VEGF_{165}$ (or VEGF-165), $VEGF_{89}$ (or VEGF-189) and $VEGF_{206}$ (or VEGF-206; the number refers to the number of amino acids in the polypeptide). All four isoforms exist as disulfide-linked homodimers. The secretion patterns of the isoforms are different in various cell types, although $VEGF_{165}$ is the most common isoform observed. A fifth variant, $VEGF_{145}$, was recently found in three human carcinoma cell lines that originated from the female reproductive tract (Poltorak et al., *J Biol Chem* (1997) 272:7157-7158). The five isoforms bind with high affinity to two receptors, Flt-1 and Flk-1/KDR, but they differ in their binding affinity for heparin and extracellular matrix. Recently, three new members of the VEGF family have been identified, VEGF-B, VEGF-C, and VEGF-D (Achen et al., *Proc Natl Acad Sci USA* (1998), 95 (2):548-53). Two splice variants of VEGF-B have been found (Olofsson et al., *J Biol Chem* (1996), 271:19310-19317; Olofsson et al., *Proc Natl Acad Sci USA* (1996), 93:2576-2581) that stimulate the growth of endothelial cells.

The term "VEGF binding activity" refers to an activity of a VEGFR polypeptide to bind a VEGF polypeptide. Determination of binding is performed using the binding assays described herein and known in the art.

The "level of VEGF mRNA" in a biological sample refers to the amount of mRNA transcribed from a VEGF gene that is present in a cell or a biological sample. The mRNA generally encodes a functional VEGF polypeptide, although mutations may be present that alter or eliminate the function of the encoded polypeptide. A "level of VEGF mRNA" typically is quantified and compared to a level from a control sample or a level expected of a control sample. However, a "level of VEGF mRNA" can also simply be detected, e.g., a subjective, visual detection by a human, with or without comparison.

The "level of VEGF polypeptide" in a biological sample refers to the amount of a VEGF polypeptide translated from a VEGF mRNA that is present in a cell or a biological sample. The polypeptide may or may not have VEGF polypeptide activity. A "level of VEGF polypeptide" typically is quantified and compared to a level from a control sample or a level expected of a control sample. However, a "level of VEGF polypeptide" can also simply be detected, e.g., a subjective, visual detection by a human, with or without comparison.

As used herein, the phrases "VEGF expression is up-regulated" or "VEGF is overexpressed" and grammatical equivalents thereof refer to a VEGF polypeptide or VEGF polynucleotide above a determined reference level. Thus, for example, in accordance with the present invention, a reference level of VEGF polypeptide or VEGF polynucleotide in a normal or healthy subject is identified as a cut-off value, above which there is a significant correlation between the level of VEGF polypeptide or VEGF polynucleotide and a cancer. Typically, VEGF levels in the serum of cancer patients are at least about 2 times, and in certain cancers, such as ovarian cancer, usually at least about 5 times and more usually at least about 10 times higher than a VEGF level in a normal or healthy person (e.g., see, Manenti et al., *Eur J Cancer* (2003), 39:1948-1956). The terms "up-regulated" and "overexpressed" are used interchangeably herein. Methods for determining VEGF levels are known in the art and include, but are not limited to RT-PCR and use of anti-VEGF antibodies.

"Correlating the amount" means comparing an amount of a substance, molecule or marker (such as VEGF) that has been determined in one sample to an amount of the same substance, molecule or marker determined in another sample. The amount of the same substance, molecule or marker determined in another sample may be specific for a given disease or cancer.

Synonyms of the term "determining the amount" are contemplated within the scope of the present invention and include, but are not limited to, detecting, measuring, testing or determining, the presence, absence, amount or concentration of a molecule, such as VEGF.

The terms "VEGFR" or "VEGF receptor" refer to receptors that bind VEGF or VEGF family members, splice variants and isoforms. The VEGF receptor family of tyrosine kinases is characterized by seven immunoglobin-like sequences in the extracellular domain and a split tyrosine kinase domain. VEGFRs include: (i) Flt-1 (fins-like tyrosine kinase), which is also known as VEGFR-1 (Shibuya et al., *Oncogene* (1990), 5:519-524; De Vries et al., *Science* (1992), 255:989-991); (ii) Flk-1 (fetal liver kinase), the mouse RTK (Quinn et al., *Proc Natl Acad Sci USA* (1993), 90:7533-7537; Millauer et al., *Cell* (1993), 72:835-846) and its human homolog, KDR (kinase insert domain-containing receptor; Terman et al., *Biochem Biophys Res Comm* (1992), 187:1579-1586); and (iii) Flt-4, which is expressed on lymphatic endothelium, but not vascular endothelium (Pajusola et al., *Cancer Res* (1992), 52:5738-43).

The term "VEGFR-FasL" refers to a fusion protein that comprises (i) an amino acid sequence of a VEGFR, a VEGFR fragment, a VEGFR domain, a VEGFR related polypeptide or a fragment of a VEGFR related polypeptide and (ii) an amino acid sequence of a FasL, a FasL fragment, a FasL related polypeptide or a fragment of a FasL related polypeptide. Typically, the amino acid sequence of a VEGFR, a VEGFR fragment, a VEGFR domain, a VEGFR related polypeptide or a fragment of a VEGFR related polypeptide is fused to the N-terminal amino acid sequence of a FasL, a FasL fragment, a FasL related polypeptide or a fragment of a FasL related polypeptide using standard molecular cloning techniques.

The terms "VEGFR polypeptide" or VEGFR nucleic acid" refer to isolated nucleic acids, polypeptides and polymorphic variants, alleles, mutants, and interspecies homologues thereof and as further described herein, that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 50, 75, 100, 150, 200, 250, 300 or more amino acids, to (i) an extracellular domain of a vascular endothelial growth factor (VEGF) receptor-1 sequence shown below; (ii) an extracellular domain of a vascular endothelial growth factor (VEGF) receptor-2 sequence shown below; or (iii) an extracellular domain of a vascular endothelial growth factor (VEGF) receptor-3 sequence shown below; (2) bind to antibodies, e.g., polyclonal antibodies, raised against an immunogen comprising an amino acid sequence shown below, or conservatively modified variants thereof; (3)

bind a VEGF polypeptide; (4) compete with a naturally occurring VEGF receptor-1, VEGF receptor-2 or VEGF receptor-3 protein for binding a VEGF polypeptide; (5) inhibits binding of VEGF to a VEGF receptor; (6) specifically hybridize under stringent hybridization conditions to a nucleic acid sequence shown below, or conservatively modified variants thereof; (7) have a nucleic acid sequence that has greater than about 90%, preferably greater than about 96%, 97%, 98%, 99%, or higher nucleotide sequence identity, preferably over a region of at least about 100, 200, 300, 400, 500, 600, 700, 800, 900, 1,000 or more nucleotides, to SEQ ID NO: 17 or SEQ ID NO:18 (human VEGFR-2); SEQ ID NO:21 (human VEGFR-1); and/or (8) have at least 50, often 75, 100, 115, 150, 175, 200, 250, or 300 contiguous amino acid residues of SEQ ID NO:1 or SEQ ID NO:4 (human VEGFR-2) or of SEQ ID NO:19 or SEQ ID NO:20 (human VEGFR-1) or SEQ ID NO:24 (human neurphilin-1) or SEQ ID NO:25 (human VEGFR-3).

A VEGFR polynucleotide or polypeptide sequence is typically from a human, but may be from other mammals, but not limited to, a non-human primate, a rodent, e.g., a rat, mouse, or hamster; a cow, a pig, a horse, a sheep, or other mammal. Therefore, in some embodiments, a VEGFR polypeptide and a VEGFR subdomain polypeptide as described herein can comprise a sequence that corresponds to a human VEGFR sequence. Thus, exemplary VEGFR are provided herein and are known in the art. For example, GenBank accession numbers for human VEGFR-2 polypeptide are NP_002244 and P35968. The GenBank accession numbers for mouse VEGFR-2 polypeptide, for example, is P35918; and for rat VEGFR-2, 008775. A human VEGFR-2 cDNA sequence can be found at GenBank NM_002253. GenBank accession numbers for human VEGFR-1 polypeptide are NP_002010, P17948, AAC16449, CAI17096, and CAI14846. The GenBank accession numbers for mouse VEGFR-1 polypeptide, for example, is NP_034358; and for rat VEGFR-1, NP_062179 and P53767. A human VEGFR-1 cDNA sequence can be found at GenBank NM_002019.

II. VEGFR-Death Ligand Fusion Proteins

The present invention provides novel fusion proteins that bind to a death receptor. A fusion protein of the present invention comprises (i) a vascular endothelial growth factor receptor (VEGFR) polypeptide that binds a vascular endothelial factor (VEGF) polypeptide and (ii) a death ligand comprising an oligomerization domain and a death receptor recognition moiety, wherein the C-terminus of the VEGFR polypeptide is linked to the N-terminus of the death ligand.

A. VEGF Receptor Polypeptides

VEGFR polypeptides useful for making the fusion proteins of the present invention can be obtained from several VEGFRs, such as Flt-1 (fms-like tyrosine kinase; VEGFR-1), Flk-1 (fetal liver kinase; KDR; VEGFR-2) and Flt-4. For the purpose of the present invention, a VEGFR polypeptide that binds a VEGF, typically comprises an extracellular domain or a portion thereof of a VEGFR.

A preferred VEGFR polypeptide comprises an extracellular domain or a portion of the extracellular domain of VEGFR-1. Preferably, the VEGFR-1 is a human VGEFR-1. An amino acid sequence of a human VEGFR-1 is shown in SEQ ID NO:19.

Several VEGFR-1 polypeptides or VEGFR-1 subdomain polypeptides can be linked to a Fas ligand to generate a fusion protein of the present invention. In a preferred embodiment, a VEGFR-1 polypeptide or a VEGFR-1 subdomain polypeptide is selected from the group consisting of (i) a polypeptide comprising the amino acid sequence of SEQ ID NO:20; (ii) a polypeptide comprising amino acid residues 1 to 747 of SEQ ID NO:19; (iii) a polypeptide comprising amino acid residues 32 to 747 of SEQ ID NO:19; (iv) a polypeptide comprising amino acids 151 to 214 of the amino acid sequence of SEQ ID NO:19; (v) a polypeptide comprising amino acids 230 to 327 of the amino acid sequence of SEQ ID NO:19; (vi) a polypeptide comprising amino acids 129 to 230 of VEGFR1 (SDT-GRPFVEMYSEIPEIIHMTE-GRELVIPCRVTSPNITVTLKKFPLDTLIPDGKRIIWDS RKGFIISNATYKEIGLLTCEATVNGH-LYKTNYLTHRQTNTII (SEQ ID NO:55) as shown in FIG. 10; domain 2 (D2)), and (vii) a polypeptide having VEGF binding activity comprising an amino acid sequence wherein one to several amino acid residues have been deleted, substituted, or added in the amino acid sequence of any one of (i) to (vi).

The phrase "one to several amino acid residues have been deleted, substituted, or added in the amino acid sequence" means that typically less than 25, more typically less than 20, even more typically less than 15 and most typically less than 10 amino acid residues have been deleted, substituted, or added in the amino acid sequence.

Each of the VEGFR-1 subdomain polypeptides comprises at least one IgG-like domain. An IgG-like domain of human VEGFR-1 comprises amino acid residues 1 to 747 of SEQ ID NO:19; amino acid residues 32 to 747 of SEQ ID NO:19; amino acid residues 32 to 123 of SEQ ID NO:19; amino acid residues 151 to 214 of SEQ ID NO:19; amino acid residues 230 to 327 of SEQ ID NO:19; amino acids residues 335 to 4221 of SEQ ID NO:19; amino acid residues 428 to 553 of SEQ ID NO:19; amino acid residues 556 to 654 of SEQ ID NO:19; or amino acid residues 661 to 747 of SEQ ID NO:19.

Also preferred are other mammalian VEGFR-1 polypeptides, including, but not limited mouse and rat VEGFR-1 polypeptides. Other mammalian VEGFR-1 subdomain polypeptides can be identified by alignment of the mammalian VEGFR-1 sequence to the human VEGFR-1 amino acid sequence.

Another preferred VEGFR polypeptide comprises an extracellular domain or a portion of the extracellular domain of VEGFR-2. Preferably, the VEGFR-2 is a human VGEFR-2. In a preferred embodiment of the present invention, a fusion protein comprises a VEGFR-2 polypeptide comprising the amino acid sequence of SEQ ID NO: 1. This VEGFR-2 polypeptide comprises the signal peptide of human VEGFR-2. In another preferred embodiment of the present invention, a fusion protein comprises a VEGFR-2 polypeptide comprising the amino acid sequence of SEQ ID NO:4. This VEGFR-2 polypeptide does not comprises a signal peptide.

Several VEGFR-2 polypeptides or VEGFR-2 subdomain polypeptides can be linked to a Fas ligand to generate a fusion protein of the present invention. In a preferred embodiment, a VEGFR-2 polypeptide or a VEGFR-2 subdomain polypeptide is selected from the group consisting of (i) a polypeptide comprising the amino acid sequence of SEQ ID NO: 1; (ii) a polypeptide comprising the amino acid sequence of SEQ ID NO:2; (iii) a polypeptide comprising the amino acid sequence of SEQ ID NO:3; (iv) a polypeptide comprising the amino acid sequence of SEQ ID NO:4; (v) a polypeptide comprising the amino acid sequence of SEQ ID NO:5; (vi) a polypeptide comprising the amino acid sequence of SEQ ID NO:6; (iiv) a polypeptide comprising amino acids 141 to 207 of the amino acid sequence of SEQ ID NO: 1; (iix) a polypeptide comprising amino acids 224 to 320 of the amino acid sequence of SEQ ID NO:1; and (ix) a polypeptide having VEGF binding activity comprising an amino acid sequence wherein one to several amino acid residues have been deleted, substituted, or added in the amino acid sequence of any one of (i) to (iix).

Each of the VEGFR-2 subdomain polypeptides comprises at least one IgG-like domain. In a preferred embodiment of the present invention a VEGFR-death ligand fusion protein comprises an IgG-like domain of human VEGFR-2 comprising amino acid residues 141 to 207 of the amino acid sequence of SEQ ID NO:1. In another embodiment, an IgG-like domain of human VEGFR-2 comprises amino acid residues 224 to 320 of the amino acid sequence of SEQ ID NO:1.

VEGFR subdomain polypeptides as described herein can be interchanged. Thus, a VEGFR polypeptide may be designed that comprises one or more IgG-like domain of VEGFR-1, preferably human VEGFR-1 and one or more IgG-like domain of human VEGFR-2, preferably human VEGFR-2.

In certain embodiments of the present invention a VEGFR is a VEGFR homolog, a VEGFR isoform, a VEGFR ortholog, or a VEGFR related polypeptide.

B. Death Ligand

The present invention provides novel fusion proteins comprising a VEGFR polypeptide as described above and a death ligand that can bind to a death receptor. The death ligand that is linked to a VEGFR polypeptide comprises an oligomerization domain and a death receptor recognition moiety.

Death ligands useful for making the fusion proteins of the present invention are reviewed in Lavrik et al., *J Cell Sci* (2005), 118:265-267 (hereby incorporated in its entirety by reference) and amino acid sequences and nucleotide sequences are available in GenBank. A death ligand comprising an oligomerization domain and a death receptor recognition moiety useful for making the fusion proteins of the present invention can be obtained from several death ligands, such as Fas ligand (FasL), Tumor necrosis factor (TNF) or lymphotoxin (LT). For the purpose of the present invention, a death ligand comprising an oligomerization domain and a death receptor recognition moiety e that binds to a death receptor typically comprises an extracellular domain or a portion thereof of a death ligand.

C. FasL

In a preferred embodiment of the present invention, the fusion protein binds to Fas and the death ligand is a Fas ligand (FasL). Thus, a preferred fusion protein of the present invention, VEGFR-FasL, comprises a Fas ligand comprising an oligomerization domain and a death receptor recognition moiety. A FasL, within a VEGFR-FasL fusion protein of the present invention contains at least a functional domain or determinants necessary and sufficient to bind to the Fas protein and transmit an apoptotic signal. Typically, such FasL determinants contain only a portion of the extracellular domain, however, they retain the binding specificity of an intact FasL and are soluble.

A preferred FasL polypeptide for use in the present invention comprises an extracellular domain or a portion of the extracellular domain of FasL. Preferably, the FasL is a human FasL. An amino acid sequence of a human FasL polypeptide comprising a trimerization domain and a binding domain for its receptor, Fas, is shown in SEQ ID NO:11. Thus, in a preferred embodiment a fusion protein of the present invention comprises a FasL comprising an amino acid sequence as shown in SEQ ID NO: 11.

In other preferred embodiments, the FasL is a mammalian FasL and includes, but is not limited to, FasL from mouse or rat. Thus, in one embodiment, a fusion protein of the present invention comprises a murine FasL polypeptide as shown in SEQ ID NO:12. In another embodiment, a fusion protein of the present invention comprises a rat FasL polypeptide as shown in SEQ ID NO:13.

Another FasL useful for the present invention is a polypeptide having Fas binding activity comprising an amino acid sequence wherein one to several amino acid residues have been deleted, substituted, or added in the amino acid sequence of SEQ ID NO: 11, SEQ ID NO:12 or SEQ ID NO:13.

A death ligand comprises two subdomains, an oligomerization domain and a death receptor recognition moiety. FIG. 1 schematically shows a FasL trimerization domain (i.e., the oligomerization domain) and the FasL Fas-binding domain (i.e., the death receptor recognition moiety). As described further herein, TNF shows a similar structure.

In one aspect of the invention, death ligand subdomain as described herein can be interchanged. Thus, for example, a FasL polypeptide may be designed that comprises a FasL Fas binding domain and a TNF trimerization domain or vice versa. TNF domains and the corresponding amino acid sequences are known in the art and corresponding domains can be identified by one of ordinary skill in the art without undue experimentation (see also below).

In another aspect, chimeric FasL polypeptides can be designed that comprise, for example, a FasL Fas recognition moiety of a human FasL and a FasL trimerization domain from another mammal, such as mouse or rat.

For use in human patients, preferably the human Fas ligand will be used. FasL from other species may be used for in vitro testing or for in vivo testing in, for example, mice and rats.

FasL fusion proteins or FasL variants are described, for example, in U.S. Pat. Nos. 6,451,759; 6,544,523; 6,348,334; 6,235,878; 6,046,310; 6,001,962; U.S. Patent Application Nos. 2004/0126859; 2004/0053249; and 2005/0013816, all of which are explicitly incorporated herewith by reference. In certain embodiments of the present invention FasL is a FasL homolog, a FasL isoform, a FasL ortholog, or a FasL related polypeptide.

D. VEGFR-Death Ligand Fusion Proteins

As explained herein in detail, the VEGFR-death ligand fusion proteins of the present invention are different from the many agents developed or being developed that target VEGF or its receptors. All of those agents, including neutralizing antibodies, soluble VEGF receptors, RNA aptamers, RNAi, ribozymes, antisense, small molecule kinase inhibitors) are designed to inhibit the expression or activity of VEGF or its receptors. Non of those exploits VEGF overexpression to generate apoptotic activity. The present invention, provides compositions, such as VEGFR-death ligand fusion proteins that do exactly that—exploiting, for example, a tumor's overexpression of VEGF to use the tumor's own weapon as a death factor, i.e., to induce apoptosis on those tumors expressing a death receptor.

The present invention provides novel VEGFR-death ligand fusion proteins. A preferred embodiment of the invention is diagrammed in FIG. 1. Such an embodiment, wherein a VEGFR polypeptide is linked to a FasL, is denoted VEGFR-FasL. In this embodiment the carboxy-terminus of the VEGFR polypeptide is linked to the amino-terminus of FasL. The FasL will preferably be attached to the carboxy-terminus of the VEGFR polypeptide, but may also be attached elsewhere.

A VEGFR-death ligand fusion protein, and in particular a VEGFR-FasL fusion protein, as exemplified herein by VEGFR-2-FasL as shown in SEQ ID NO: 22 and in SEQ ID NO:23, is a soluble protein. This soluble protein combines a VEGF-binding domain from an extracellular domain of a VEGFR with the trimerization domain and a death receptor recognition moiety of a death ligand.

A VEGFR-death ligand fusion protein of the present invention, and in particular a VEGFR-FasL fusion protein, is designed such that VEGF dimmers would bring together VEGFR-death ligand trimers into clusters, which could then bind to, cluster, and activate a death receptor, and in particular Fas. Such an embodiment is schematically depicted in FIG. 1.

Preferred VEGFR-death ligand fusion proteins are depicted in FIGS. 5 to 8. These preferred VEGFR-death ligand fusion proteins comprise the D1, D2 and D3 domains of Flk.

Another preferred VEGFR-death ligand fusion protein of the present invention is depicted in FIGS. 9 and 10. This preferred VEGFR-death ligand fusion protein comprises domain 2 (D2) of VEGFR1.

1. Signal Peptides

The present invention provides novel fusion proteins comprising a VEGFR polypeptide and a death ligand. Full-length fusion proteins including a signal peptide sequence (e.g., see SEQ ID NO:22) and mature full-length fusion proteins without a signal peptide (e.g., SEQ ID NO:23) are useful for practicing the methods of this invention and find use as compositions in the pharmaceutical compositions and kits of this invention.

Thus, the fusion proteins of the present invention may or may not comprise a signal peptide sequence depending on their intended use and mode of production (see further herein). The signal peptide sequence may be a homologous signal peptide sequence, i.e., a signal peptide which is normally found at the N-terminus of a secreted protein (e.g., see FIG. 3). Alternatively, for example, a murine VEGFR signal sequence can replace a human signal VEGFR sequence or vice versa, depending on the expression system used to generate the fusion proteins of this invention.

2. Linker Sequences

Optionally, VEGFR-FasL comprises a linker. Such a polypeptide linker between the N-terminal VEGFR and the C-terminal FasL is preferably made so as to allow binding of a VEGF polypeptide to the VEGFR polypeptide and dimerization or trimerization of FasL and binding of the VEGFR-FasL to Fas. The linker may contain from 1 to about 100 amino acid residues, preferably 5-50. In a preferred embodiment a linker sequence comprises the 5 amino acid residues as shown in SEQ ID NO: 7. Linker sequences that can be inserted between the VEGFR polypeptide and a death ligand polypeptide are not critical. Other preferred linker sequences comprise Gly linkers or Gly/Ser linkers.

E. Other Growth Factor/Death Ligand Proteins

The basic principle of the present invention, i.e., converting a growth factor activity of a growth factor, as exemplified herein by VEGF, into a death factor, can be applied to other growth factors as well. In these embodiments, the VEGFR polypeptide would be replaced by a binding domain for another growth factor, for example, platelet derived growth factor (PDGF). Thus, without undue experimentation and with a reasonable expectation of success, an ordinary skill in the art will be able, by following this disclosure and obtaining relevant information pertaining to sequences of growth factors, or growth factor receptors from public data bases, such as GenBank or obtaining cloned DNAs encoding such growth factors or growth factor receptors from the American Type Culture Collection (ATCC).

F. Other Death Receptors/Death Ligand Proteins

The fusion proteins of the present invention bind to a death receptor, preferably to a death receptor on the surface of a cell expressing the death receptor. Death receptors useful as targets in the methods of the present invention typically belong to the TNF superfamily of receptors and include the p55 and p75 tumor necrosis factor receptor (TNFRs) and Fas (also called FAS/APO1). Tumor Necrosis Factor (TNF-α) and lymphotoxin (TNF-β) bind to both p55 and p75 and thereby initiate events leading to the death of, for example, a tumor cell expressing p55 or p75.

Thus, in another aspect of the present invention, a VEGFR-death ligand fusion protein comprises a VEGFR polypeptide as described herein, and a TNF polypeptide comprising an oligomerization domain and a death receptor recognition moiety for binding to TNFR. In another embodiment, a VEGFR-death ligand fusion protein comprises a VEGFR polypeptide and a LT polypeptide comprising an oligomerization domain and a death receptor recognition moiety for binding to TNFR.

G. Nucleic Acid Encoding VEGFR-FasL Fusion Protein

In another aspect, the invention is directed to recombinant nucleic acids that encode all or part of a VEGFR-FasL fusion protein. In a preferred embodiment of the present invention, a nucleic acid that encodes all or part of a VEGFR-FasL fusion protein comprises the nucleotide sequence shown in FIG. 7. Another preferred nucleic acid that encodes all or part of a VEGFR-FasL fusion protein comprises the nucleotide sequence shown in FIG. 9. Other preferred nucleic acids encoding all or part of a VEGFR-FASL fusion protein are those shown in FIGS. 7 and 9 in which the sequences encoding the linker sequence or the FLAG-tag are not included. Such nucleic acids can be generated by one of skill in the art using PCR and appropriately designed PCR primers.

In general, nucleic acid sequences encoding a VEGFR-death ligand fusion protein and related nucleic acid sequence homologs are cloned from cDNA and genomic DNA libraries by hybridization with a probe, or isolated using amplification techniques with oligonucleotide primers. For example, sequences are typically isolated from mammalian nucleic acid (genomic or cDNA) libraries by hybridizing with a nucleic acid probe.

Amplification techniques using primers can also be used to amplify and isolate nucleic acids from DNA or RNA. Suitable primers for amplification of specific sequences can be designed using principles well known in the art (see, e.g., Dieffenfach & Dveksler, *PCR Primer: A Laboratory Manual* (1995)). These primers can be used, e.g., to amplify either the full length sequence or a fragment of a VEGFR polypeptide or a death ligand.

Synthetic oligonucleotides can also be used to construct VEGFR-death ligand encoding genes for use as probes or for expression of protein. This method is performed using a series of overlapping oligonucleotides usually 40-120 bp in length, representing both the sense and nonsense strands of the gene. These DNA fragments are then annealed, ligated and cloned. Alternatively, amplification techniques can be used with precise primers to amplify a specific subsequence of the nucleic acid. The specific subsequence is then ligated into an expression vector.

The nucleic acid encoding a VEGFR-death ligand fusion protein is typically cloned into intermediate vectors before transformation into prokaryotic or eukaryotic cells for replication and/or expression. These intermediate vectors are typically prokaryotic vectors, e.g., plasmids, or shuttle vectors.

Optionally, nucleic acids encoding chimeric proteins comprising VEGFR, death ligands or domains thereof can be made according to standard techniques.

H. Expression of VEGFR-Death Ligand Fusion Proteins

To obtain high level expression of a VEGFR-death ligand nucleic acid, one typically subclones a VEGFR-death ligand nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook & Russell, *Molecular Cloning, A Laboratory Manual* (3rd Ed, 2001), Ausubel et al. (eds.), *Current Protocols in Molecular Biology*, John Wiley & Sons, NY (1993); and Kriegler, *Gene Transfer and Expression, A Laboratory Manual*, Stockton Press, NY (1990). Bacterial expression systems for expressing the VEGFR-death ligand protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the VEGFR-death ligand-encoding nucleic acid in host cells. A typical expression cassette thus contains a promoter operably linked to the nucleic acid sequence encoding a VEGFR-death ligand and signals required for efficient polyadenylation of the transcript, ribosome binding sites, and translation termination. The nucleic acid sequence encoding a VEGFR-death ligand may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a VEGFR-death ligand—encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of a VEGFR-death ligand protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook and Russell., supra). It is only necessary that the particular genetic engineering procedure used be capable of successfully introducing at least one gene into the host cell capable of expressing a VEGFR-death ligand. Introduction of a VEGFR-FasL nucleic acid into a cell can be performed by transient transfection or stable transfection (Examples 4 and FIGS. 11a and 11B).

After the expression vector is introduced into the cells, the transfected cells are cultured under conditions favoring expression of VEGFR-death ligand, which is recovered from the culture using standard techniques (see, e.g., Scopes, *Protein Purification: Principles and Practice* (1982); U.S. Pat. No. 4,673,641; Ausubel et al., supra; and Sambrook et al., supra). Generation of useful VEGFR-FasL fusion proteins is described in Example 4 and FIGS. 11A and 11B.

I. Purification of VEGFR-FasL Fusion Protein

VEGFR-death ligand fusion proteins of the present invention can be purified using methods well known in the art, e.g., Sambrook & Russell, *Molecular Cloning, A Laboratory Manual* (3rd Ed, 2001); Kriegler, *Gene Transfer and Expression: A Laboratory Manual* (1990); and *Current Protocols in Molecular Biology* (Ausubel et al., eds., 1994-1999).

Figure 6:
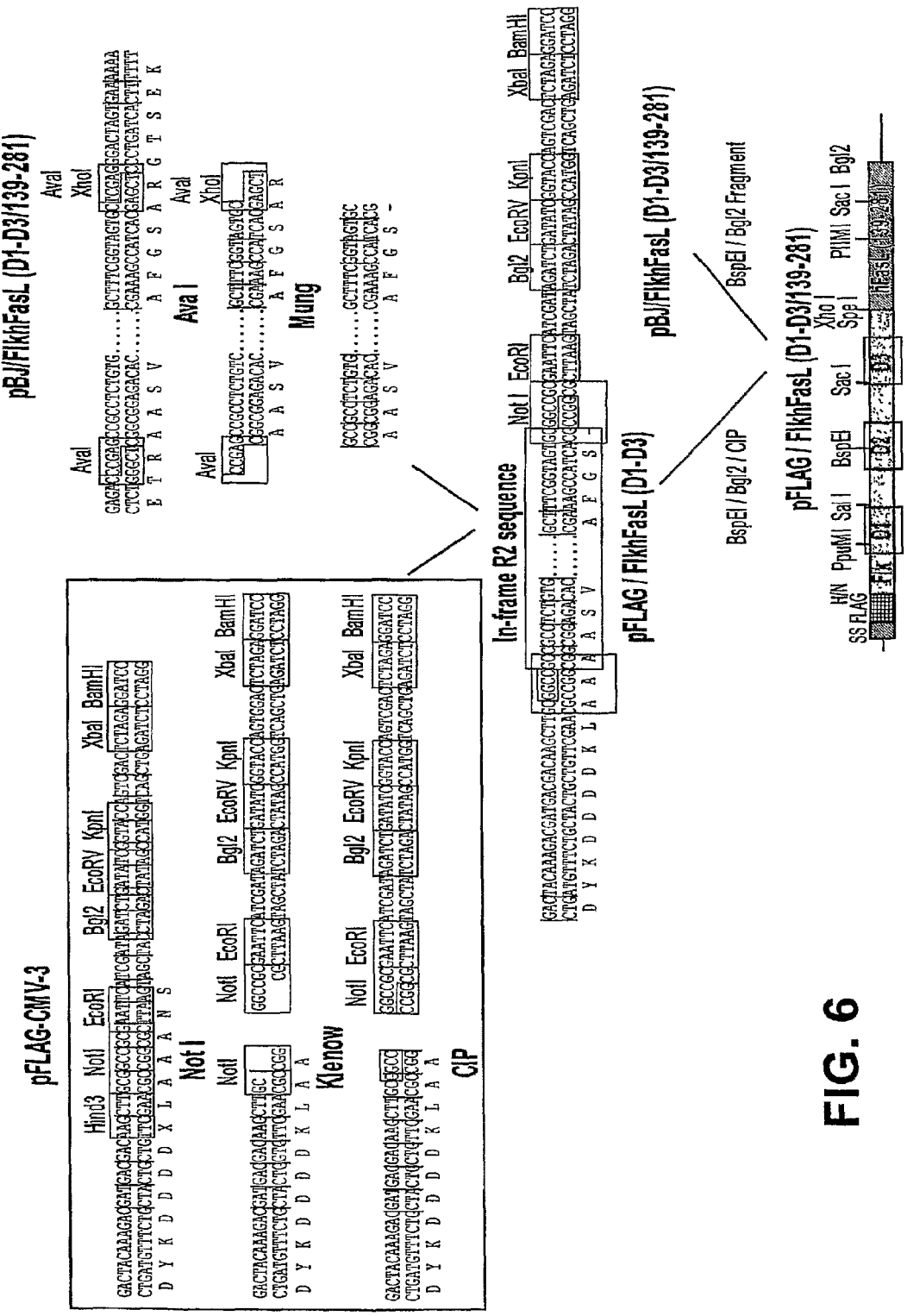
FIG. 6 depicts the construction of a VEGFR/FasL fusion protein encoding nucleic acid, FLAG/FlkhFasL (D1-D3/139-281) (SEQ ID NOS:33-53). Details are described in Example 3.

VEGFR-death ligand fusion protein of the present invention can thus be purified by conventional protein purification methods. Alternatively, a tag attached to the VEGFR-death ligand fusion protein will be employed for protein purification. Tags are known in the art and include, but are not limited to FLAG- and HA-tags. Typically, coding sequences for these tags are linked to a VEGFR-death ligand coding sequence and are expressed when the transcribed RNA is translated. A preferred tag is a FLAG tag. Preferred embodiments of the present invention comprising a FLAG-tagged VEGFR-death ligand fusion protein are shown in FIGS. 6 and 11 and described in detail in Examples 3 and 4.

In a preferred embodiment a cleavable peptide sequence is inserted in between the tag and the VEGFR-death ligand fusion protein. This is particularly advantageous for cleaving off the tag after protein purification.

J. Binding of VEGF to VEGFR-FasL

VEGFR fusion proteins of the invention bind vascular endothelial growth factor (VEGF). Bioassays to monitor binding of VEGF to the extracellular domain of VEGF receptors are known in the art and are described herein. For example, Achen et al. (incorporated hereby by reference) describe a bioassay to monitor the binding a VEGF ligand to the extracellular domain of VEGFR-2 and binding assays with soluble VEGFR extracellular domains. Binding of a VEGF to a VEGFR fusion protein of the present invention can be determined using the assays of Achen et al. (*Proc Natl Acad Sci USA* (1998), 95:548-553).

Binding of VEGF to a VEGFR-FasL fusion protein of the present invention activates the VEGFR-FasL fusion protein. A VEGFR-FasL fusion protein of the present invention may be activated by human VEGF, mouse VEGF (Example 11) or any other mammalian VEGF. In addition, a VEGFR-FasL fusion protein of the present invention may be activated by a VEGF/PlGF heterodimer or by PlGF (Example 11).

K. Binding of VEGFR-FasL to Fas

VEGFR-FasL fusion proteins of the invention bind to Fas. Bioassays to monitor FasL-Fas binding are known in the art and are described herein. For example, Schneider et al. (incorporated hereby by reference) describe cytotoxic assays and in vitro Fas-FasL binding assays to monitor the binding a FasL to the extracellular domain of Fas. Binding of a VEGFR-FasL of the present invention to Fas can be determined using the assays of Schneider et al. (*J Biol Chem* (1997), 272 (30): 18827-18833).

In a preferred embodiment, a VEGFR-FasL fusion protein will have a greater effectiveness relative to soluble FasL or its extracellular domain to induce apoptosis or death in Fas-expressing cancer cells.

III. Method for Neutralization of VEGF Activation of VEGF Receptors Using a VEGFR-Death Ligand Fusion Protein VEGFR-death ligand fusion proteins of the present invention find use in a variety of ways. For example, a VEGFR-death ligand fusion protein, in particular a VEGFR-FasL fusion protein, can be used as an anti-cancer agent for tumors that overexpress VEGF. A VEGFR-death ligand fusion protein of the present invention can also be used as an anti-angiogenic agent for use in diseases characterized by pathologic angiogenesis, such as cancer, rheumatoid arthritis, or proliferative retinopathy.

In a preferred embodiment of this invention, a method of neutralizing a VEGF activation of a VEGF receptor on using a VEGFR-death ligand fusion protein is provided. This method comprises the step of contacting a VEGF with a VEGFR-death ligand fusion protein.

Neutralization of VEGF activation of a VEGF receptor on cells, such as tumor cells, may be performed in vitro or in vivo. Neutralization of VEGF activation of a VEGF receptor comprises contacting a biological sample comprising a cell expressing a VEGF receptor on its cell surface with a fusion protein of this invention. In vitro, the biological sample, can be contacted with the fusion protein, e.g., VEGFR-FasL before, simultaneously with, or after, adding VEGF.

In vivo, a fusion protein of this invention is contacted with a biological fluid, such as blood, or a tumor by administration to a mammal. This in vivo neutralization method is useful for inhibiting or preventing angiogenesis in a mammal associated with pathological conditions such as tumor growth. Thus, the fusion proteins of the present invention, such as VEGFR-FasL are anti-angiogenic and anti-tumor therapeutics.

This method is effective for treating subjects with tumors and neoplasms, including malignant tumors and neoplasms, such as blastomas, carcinomas or sarcomas, and especially highly vascular tumors and neoplasms. Some examples of tumors that can be treated with the antibodies and fragments of the invention include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors.

IV. Methods for Inducing Apoptosis Using a VEGFR-Death Ligand Fusion Protein

A VEGFR-death ligand fusion protein of the present invention finds use in a variety of ways. In a preferred embodiment of this invention, a method of reversing the activity of a VEGF from an angiogenic factor into a cell death factor is provided. This method is based on the observation that VEGF is overexpressed by many cancers, and in particular human cancers. Cancers overexpressing VEGF include, but are not limited to, glioma, melanoma, gastric cancer, Kaposi sarcoma, epidermoid carcinoma, hemangioblastoma, breast cancer, colon cancer, renal cell tumors, pituitary tumors, lung cancer and prostate cancer. A preferred cancer is a glioblastoma. Another preferred cancer is prostate cancer.

The concept of this method is to make the VEGF that is overexpressed by a tumor act as a death factor against the tumor itself or its blood vessels. In essence, to turn the tumor's weapon, overexpressed VEGF, which it needs to sustain growth and metastasize, against the tumor itself. Thus, the compositions of the present invention are useful to induce apoptosis or induce cytotoxic effects in cancer cells.

This method comprises the step of contacting a VEGF with a VEGFR-death ligand fusion protein of the present invention. This method further comprises the step of contacting a death receptor on the surface of a cell with a VEGFR-death ligand fusion protein of the present invention to which a VEGF polypeptide has bound. Thus, in this embodiment, without binding a VEGF polypeptide, a VEGFR-death ligand fusion protein will not bind to a death receptor.

The compositions of the present invention are also useful to induce apoptosis or induce cytotoxic effects in cells other than cancer cells. For example, the VEGFR-FasL fusion proteins of the present invention are useful for inducing apoptosis and cytotoxic effects in microvascular endothelial cells, such as adrenal cortical endothelial cells.

Upon binding of the VEGFR-death ligand fusion protein (having bound a VEGF polypeptide) to a death receptor on a cell, apoptosis, i.e., cell death, is induced. The VEGFR-death ligand fusion protein binds to the death receptor via a death receptor recognition moiety as described herein. For example a FasL which is produced as a trimer, induces apoptosis by binding to, clustering and thereby activating Fas. A VEGFR-FasL fusion protein of the present invention comprising a FasL polypeptide comprising an oligomerization domain and a death receptor recognition moiety induces apoptosis in the same manner. Thus, an important feature is that Fas clustering by FasL or by a VEGFR-FasL fusion protein is required for Fas activation.

Preferably, a VEGFR-ligand fusion protein of the present invention has no or minimal apoptotic activity in the absence of VEGF. This has been demonstrated in several in vitro experiments and is shown exemplary in FIGS. 11, 13, 14 and 15.

Preferably, a VEGFR-ligand fusion protein of the present invention has increased apoptotic activity in the absence of VEGF. This has been demonstrated in several in vitro experiments and is shown exemplary in FIGS. 11, 13, 14 and 15. An "increased apoptotic activity" in this context means at least a two-fold stimulation as compared to without VEGF, preferably a three-fold stimulation, more preferably a five-fold In a preferred embodiment, the method for inducing apoptosis in a cell wherein VEGF expression is up-regulated and wherein the cell expresses a death receptor comprises the step of exposing the cell to a composition or contacting the cell with a composition comprising a VEGFR-death ligand fusion protein or a polynucleotide encoding a VEGFR-death ligand fusion protein as described herein. In a preferred embodiment, the polynucleotide encodes the VEGFR-death ligand fusion protein of SEQ ID NO:22 or SEQ ID NO:23.

In another preferred embodiment of the present invention, the polynucleotide comprises SEQ ID NO:14.

In one aspect of the present invention, a VEGFR-death ligand fusion protein or polynucleotide is used to induce apoptosis in vitro, e.g., in a cultured cell line. In another preferred aspect, the VEGFR-death ligand fusion protein or polynucleotide is used to induce apoptosis in vivo, i.e., in an animal, preferably a mammal, including human, and preferably in cancer cells.

V. Method for Treating a Cancer Overexpressing VEGF and Expressing Fas Receptor

A. Measuring of VEGF in Normal Individuals and in Cancer Patients

Bioassays for measuring or determining VEGF in normal individuals and in cancer patients have been described in the prior art and are useful to determine levels of endogenous VEGF in an individual prior to administering a VEGFR-death ligand fusion protein of the present invention. For example, Cooper et al. assessed the clinical relevance of serum VEGF levels in distinguishing patients with ovarian cancer from those with benign adnexal masses and concluded that preoperative VEGF levels may be useful in differentiating benign adnexal masses from malignancy (*Clin Cancer Res*, (2002) 8 (10):3193-7).

B. Measuring Fas Receptor Expressed in a Cancer Cell

Bioassays for measuring or determining Fas receptor expressed in a cancer cell have been described in the prior art and are useful to determine whether a targeted cancer cell expresses Faso e any other death receptor and thus, is susceptible for induction of apoptosis by a VEGFR-death ligand fusion protein of the present invention. Determining whether the cancer in a patient expresses Fas or any other death receptor is desirable prior to administering a VEGFR-death ligand fusion protein of the invention. For example, the bioassay described by Algeciras-Schimnich et al., *Proc Natl Acad Sci USA*, (2003) 100:11445 can be used.

C. Method for Treating Cancer

Methods of the present invention comprise treating a cancer cell wherein VEGF is up-regulated and wherein the cancer cell expresses a death receptor. The method typically comprises inducing apoptosis using a VEGFR-death ligand fusion protein of the present invention. A preferred cancer cell is selected from the group consisting of breast cancer, prostate cancer, colon cancer, lung cancer, glioblastoma, and ovarian cancer.

This method is effective for treating subjects with tumors and neoplasms, including malignant tumors and neoplasms, such as blastomas, carcinomas or sarcomas, and especially highly vascular tumors and neoplasms. Some examples of tumors that can be treated with the antibodies and fragments of the invention include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors.

The present invention provides a method for treatment of a cancer wherein VEGF expression is up-regulated. This method comprises the step of administering to a patient a pharmaceutical composition. Such pharmaceutical compositions comprise, for example, a VEGFR-death ligand fusion protein, a VEGFR-death ligand fusion protein analog, a VEGFR-death ligand fusion protein mimetic, a VEGFR-death ligand fusion protein related polypeptide; or a polynucleotide encoding a VEGFR-death ligand fusion protein, a VEGFR-death ligand fusion protein analog, a VEGFR-death ligand fusion protein mimetic, a VEGFR-death ligand fusion protein related polypeptide. Pharmaceutical compositions of the present invention are administered alone or in combination with one or more additional therapeutic compounds or treatments. Examples of such therapeutic compounds or treatments include, but are not limited to, taxol, cyclophosphamide, tamoxifen, fluoruracil and doxorubicin.

D. Inhibition of Cell Proliferation

A VEGFR-death ligand fusion protein of the present invention finds use in a variety of ways. In a preferred embodiment of this invention, a method of inhibiting proliferation of a cell that overexpresses VEGF is provided. "Proliferation" refers to the growth of a cell, the reproduction or multiplication of a cell or morbid cysts. The VEGF that is overexpressed can be either a VEGF polypeptide or a VEGF mRNA. This method comprises the step of contacting the cell with an amount of a VEGFR-death ligand fusion protein effective to inhibit proliferation of the cell.

In a preferred embodiment of the present invention, this method is practiced in vitro. As further described herein, methods of the present invention can also be practiced in vivo.

VI. Methods for Treating Diseases and Disorders Related to Unregulated Angiogenesis and/or Vasculogenesis Using a VEGFR-FasL Fusion Protein Preventing or inhibiting angiogenesis is also useful to treat diseases, disorders and non-neoplastic pathologic conditions, related to unregulated angiogenesis and/or vasculogenesis, such as rheumatoid arthritis, neovascular glaucoma, proliferative retinopathy including proliferative diabetic retinopathy, macular degeneration, hemangiomas, angiofibromas, and psoriasis. Compositions of this invention are useful to treat such diseases.

VEGFR-death ligand fusion proteins of the present invention find use in a variety of ways. In another preferred embodiment of this invention a method of treating a disease associated with overexpression of VEGF or pathologic angiogenesis is provided. This method comprises the step of administering to a subject, preferably to a subject in need of such treatment, an amount of a polypeptide having VEGFR-death ligand fusion protein activity effective for treating the disease. Preferably, the subject is a human.

A. Rheumatoid Arthritis

In a preferred embodiment of the present invention, the disease treated with a VEGFR-death ligand fusion protein of the present invention or with a polynucleotide encoding a VEGFR-death ligand fusion protein, is rheumatoid arthritis. Rheumatoid arthritis (RA) is an inflammatory joint disease that is characterized by cellular infiltration of synovial fluid by neutrophils, and of the synovial membrane by T lymphocytes and macrophages, hyperproliferation of cells of the synovial membrane which results in formation of a pannus, and destruction of cartilage and bone (Feldman et al., *Ann Rev Immunol* (1996), 14:397-440; Paleolog, *Br J Rheumatol* (1996), 35:917-920). Angiogenesis is thought to have an important role in the pathogenesis of RA (Colville-Nash & Scott, *Annals Rheumatic Diseases* (1992), 51:919-925, and references therein).

The strongest evidence for a role as a direct angiogenic factor in RA exists for VEGF. VEGF expression is significantly higher in synovial fluid and tissue from RA patients than from patients with other types of arthritis (Fava, et al., J. Exp. Med. (1994) 180:341-346; Koch et al., *J Immunol* (1994) 152:4149-4156). The source of this VEGF appears to be elevated expression in synovial lining cells, subsynovial macrophages, fibroblasts surrounding microvessels, and vascular smooth muscle cells (Fava, et al., J. Exp. Med. (1994), 180:341-346; Koch et al., *J Immunol* (1994), 152:4149-4156; Nagashima et al., *J Rheumatol* (1995), 22:1624-1630). Indirect induction of VEGF by other factors may occur as well.

B. Psoriasis

In another preferred embodiment of the present invention, the disease treated with a VEGFR-death ligand fusion protein of the present invention or with a polynucleotide encoding a VEGFR-death ligand fusion protein, is psoriasis. Psoriasis is a chronic skin disorder that is characterized by hyperproliferation of the epidermis, inflammation, and angiogenesis. Angiogenesis appears to be crucial in the pathogenesis of psoriasis, and microvascular changes are one of the earliest detectable events in developing psoriatic lesions (for a review see Creamer & Barker, *Clin Exp Dermatol* (1995), 20:6-9). Several reports have implicated the epidermis as the origin of angiogenic factors (Nishioka & Ryan, *J Invest Dermatol* (1972), 58:33-45; Wolf & Harrison, *J Invest Dermatol* (1973), 59:40-43; Barnhill et al., *Br J Dermatol* (1984), 110: 273-281; Malhotra et al., *Lab Invest* (1989), 61:162-165).

Of the many angiogenic factors identified in skin (Arbiser, *Am Acad Derm* (1996), 34:486-497), VEGF has been the best characterized as a direct inducer of angiogenesis. VEGF is overexpressed in keratinocytes of psoriatic skin, but only minimally expressed in normal epidermis (Detmar et al., *J Exp Med* (1994), 180:1141-1146). VEGF is also overexpressed in other skin diseases such as bullous pemphigoid, dermatitis herpetiformis, and erythema multiforme (Brown et al., *Invest Dermatol* 1995, 104, 744-749), in delayed skin hypersensitivity reactions (Brown et al., *J Immunol* 1995, 154, 2801-2807), and probably after sun exposure, as suggested by the induction of VEGF expression in cultured keratinocytes following exposure to ultraviolet light (Brauchle et al., *J Biol Chem* (1996), 271:21793-21797).

C. Macular Degeneration

In a preferred embodiment of the present invention, the disease treated with a VEGFR-death ligand fusion protein of the present invention or with a polynucleotide encoding a VEGFR-death ligand fusion protein, is macular degeneration. The release of angiogenic factors from the ischemic retina has been hypothesized to be the central stimulus for retinal neovascularization. Glaucoma, vitreous hemorrhage and retinal detachment, secondary to intraocular neovascularization, accounts for the resultant vision loss in several ocular disorders such as retinopathy of prematurity, age-related macular degeneration, and diabetic retinopathy. The release of angiogenic factors by the ischemic retina to induce new blood vessel growth and increase the oxygen supply to the area turns out to be harmful as the new vessels do not grow with normal architecture. Edema, hemorrhage, vessel tortuosity, and pathological neovascularization subsequently result in retinal detachment and lead to blindness.

VEGF is constitutively expressed in the vascularized tissues of the normal eye (Adamis et al., *Arch Ophthalmol* (1996), 114:66-71), however, intraocular VEGF gene expression is increased in disease states like diabetic retinopathy (Adamis et al., *Amer J Ophthalmology* (1994), 118:445-450; Malecaze et al., *Arch Ophthalmology* (1994), 112:1476-1482).

VII. Combination Therapies

As detailed herein, the invention provides methods for using VEGFR-death ligand fusion proteins for neutralizing VEGF activation of VEGF receptors. These methods are particularly useful for inducing apoptosis, inducing cytotoxic effects in cells, treating cancer and diseases or disorders related to unregulated angiogenesis and/or vasculogenesis. In a preferred embodiment of the present invention, each of these methods may further comprise administering to a patient a second therapeutic agent, such as a chemotherapeutic agent or radiation therapy.

Examples of chemotherapeutic agents include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, The Merck Manual of Diagnosis and Therapy, 15th Ed. 1987, pp. 1206-1228, Berkow et al., eds., Rahway, N.J.

In a preferred embodiment of the present invention, a chemotherapeutic agent is selected from the group consisting of camptothecin, etoposide, bisindolylmaleimide VIII, cisplatin, taxol, doxorubicin, temozolomide, bortezomid, LY294002, and valproic acid.

VIII. Administering a VEGFR-Death Ligand Fusion Protein

In one aspect of the present invention, a nucleic acid molecule that express a VEGFR-death ligand fusion protein, such as a VEGFR-FasL as described in detail herein, may be used to introduce that nucleic acid into a mammalian cell or target tissue. Conventional viral and non-viral based gene transfer methods can be used to introduce nucleic acids encoding VEGFR-death ligand fusion proteins in mammalian cells or target tissues. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see, Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6 (10):1149-1154 (1988); Vigne, *Restorative Neurology and Neuroscience* 8:35-36 (1995); Kremer & Perricaudet, *British Medical Bulletin* 51 (1):31-44 (1995); Haddada et al., in *Current Topics in Microbiology and Immunology* Doerfler and Bohm (eds) (1995); and Yu et al., *Gene Therapy* 1:13-26 (1994).

A. Non-Viral Delivery Methods

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

B. Viral Delivery Methods

The use of RNA or DNA viral based systems for the delivery of VEGFR-death ligand fusion protein encoding nucleic acids is known in the art. Conventional viral based systems for include retroviral, lentivirus, adenoviral, adeno-associated and herpes simplex virus vectors for gene transfer.

In many gene therapy applications, it is desirable that the gene therapy vector be delivered with a high degree of specificity to a particular tissue type, e.g., lung tissue or breast tissue. A viral vector can be modified to have specificity for a given cell type by expressing a ligand as a fusion protein with a viral coat protein on the viruses outer surface. The ligand is chosen to have affinity for a receptor known to be present on the cell type of interest. For example, Han et al., *Proc Natl. Acad. Sci. U.S.A.* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient.

Ex vivo cell transfection for diagnostics, research, or for gene therapy (e.g., via re-infusion of the transfected cells into the host organism) is well known to those of skill in the art. In some embodiments, cells are isolated from the subject organism, transfected with VEGFR-death ligand encoding nucleic acids and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can also be administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences,* 17th ed., 1989).

IX. Pharmaceutical Compositions

The present invention provides pharmaceutical compositions comprising a VEGFR-death ligand fusion protein of the present invention.

In a preferred embodiment of the present invention, a pharmaceutical composition comprises (i) a fusion protein comprising: (1) a VEGFR polypeptide that binds a VEGF protein; and (2) a Fas ligand comprising an oligomerization domain and a Fas receptor recognition moiety of the extracellular domain of a Fas ligand protein; and (ii) a pharmaceutically acceptable excipient, carrier and/or diluent.

In another embodiment of the present invention, a composition is provided comprising a vector comprising a nucleic acid encoding a VEGFR-death ligand fusion protein and a pharmaceutically acceptable excipient, carrier and/or diluent. In one embodiment, the nucleic acid encoding a VEGFR-death ligand fusion protein has a nucleotide sequence as shown in SEQ ID NO:14.

Pharmaceutical compositions are useful for treating cancers overexpressing VEGF and expressing a death receptor, such as Fas. Pharmaceutical compositions are also useful for treating diseases characterized by pathologic angiogenesis as described herein.

A. Administration of Pharmaceutical Compositions

Pharmaceutical compositions comprising an activator of VEGFR-death ligand fusion protein or a VEGFR-death ligand fusion protein encoding polynucleotide can be administered to a patient for the treatment of cancer, e.g., lung cancer or breast cancer. As described in detail below, the compounds are administered, optionally with pharmaceutically acceptable carriers.

A VEGFR-death ligand fusion protein or a VEGFR-death ligand fusion protein encoding polynucleotide can be administered to a patient at therapeutically effective doses to prevent, treat, or control cancer. The compounds are administered to a patient in an amount sufficient to elicit an effective therapeutic response in the patient. An effective therapeutic response is a response that at least partially arrests or slows the symptoms or complications of the disease. An amount adequate to accomplish this is defined as "therapeutically effective dose." The dose will be determined by the efficacy of the particular VEGFR-death ligand employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the ED50 with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally.

For oral administration, the pharmaceutical compositions can take the form of, for example, tablets or capsules prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

B. Therapeutic Effective Amount and Dosing

In one embodiment of the present invention, a pharmaceutical composition or medicament is administered to a subject, preferably a human or a non-human animal, at a therapeutically effective dose to prevent, treat, or control a pathological condition or disease as described herein. The pharmaceutical composition or medicament is administered to a subject in an amount sufficient to elicit an effective therapeutic response in the subject. An effective therapeutic response is a response that at least partially arrests or slows the symptoms or complications of the pathological condition, disorder, or disease. An amount adequate to accomplish this is defined as "therapeutically effective dose" also referred to as "therapeutically effective amount."

The dosage of active agents administered is dependent on the species of warm-blooded animal (mammal), the body weight, age, individual condition, surface area or volume of the area to be treated and on the form of administration. The size of the dose also will be determined by the existence, nature, and extent of any adverse effects that accompany the administration of a particular small molecule compound in a particular subject. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

The dosage of active agents administered is also dependent on the nature of the agent. For example, a therapeutically effective amount of protein or polypeptide of the present invention (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks.

In addition, it is understood that the specific dose level for any particular animal subject will depend upon a variety of factors including the activity of the specific VEGFR-FasL fusion protein employed, the age, body weight, general health, gender, and diet of the subject, the time of administration, the route of administration, the rate of excretion, any drug combination, and the degree of expression or activity to be modulated.

In one embodiment of the present invention, a pharmaceutical composition or medicament comprising a VEGFR-death ligand fusion protein of the present invention is administered in a daily dose in the range from about 1 mg of each compound per kg of subject weight (1 mg/kg) to about 1 g/kg for multiple days. In another embodiment, the daily dose is a dose in the range of about 5 mg/kg to about 500 mg/kg. In yet another embodiment, the daily dose is about 10 mg/kg to about 250 mg/kg. In another embodiment, the daily dose is about 25 mg/kg to about 150 mg/kg. A preferred dose is about 10 mg/kg. The daily dose can be administered once per day or divided into subdoses and administered in multiple doses, e.g., twice, three times, or four times per day. However, as will be appreciated by a skilled artisan, polypeptides and proteins, such as the VEGFR-death ligand fusion proteins of the present invention may be administered in different amounts and at different times. The skilled artisan will also appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments.

To achieve the desired therapeutic effect, VEGFR-death ligand fusion proteins or nucleic acids encoding them may be administered for multiple days at the therapeutically effective daily dose. Thus, therapeutically effective administration of VEGFR-death ligand fusion proteins or nucleic acids encoding them to treat a pathological condition or disease described herein in a subject requires periodic (e.g., daily) administration that continues for a period ranging from three days to two weeks or longer. Typically, VEGFR-death ligand fusion proteins or nucleic acids encoding them will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the VEGFR-death ligand fusion proteins or nucleic acids encoding them are not administered daily, so long as the administration is repeated frequently enough to maintain a therapeutically effective concentration of the VEGFR-death ligand fusion proteins or nucleic acids encoding them in the subject. For example, one can administer the VEGFR-death ligand fusion proteins or nucleic acids encoding them every other day, every third day, or, if higher dose ranges are employed and tolerated by the subject, once a week.

Optimum dosages, toxicity, and therapeutic efficacy of VEGFR-death ligand fusion proteins or nucleic acids encoding them may vary depending on the relative potency of individual VEGFR-death ligand fusion proteins or nucleic acids encoding them and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. VEGFR-death ligand fusion proteins or nucleic acids encoding them that exhibit large therapeutic indices are preferred. While VEGFR-death ligand fusion proteins or nucleic acids encoding them that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such VEGFR-death ligand fusion proteins or nucleic acids encoding them lies preferably within a range of circulating concentrations that include the $ED_{50}$ with little or no toxicity. The dosage can vary within this range depending upon the dosage form employed and the route of administration. For any VEGFR-death ligand fusion protein or nucleic acid encoding them used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Following successful treatment, it may be desirable to have the subject undergo maintenance therapy to prevent the recurrence of the condition or disease treated.

X. Kits for Use in Diagnostic, Research, and Therapeutic Applications

For use in diagnostic, research, and therapeutic applications suggested above, kits are also provided by the invention. In the diagnostic and research applications such kits may include any or all of the following: assay reagents, buffers, VEGFR-death ligand polypeptides, VEGFR-death ligand specific nucleic acids or antibodies, hybridization probes and/or primers, VEGFR-death ligand expression constructs, small molecule activators of VEGFR-death ligand etc. A therapeutic product may include sterile saline or another pharmaceutically acceptable emulsion and suspension base.

In addition, the kits may include instructional materials containing directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In a preferred embodiment of the present invention, the kit is a pharmaceutical kit and comprises a pharmaceutical composition comprising (i) a polynucleotide encoding a VEGFR-death ligand polypeptide and (ii) a pharmaceutical acceptable carrier. In another preferred embodiment of the present invention, the kit is a pharmaceutical kit and comprises a pharmaceutical composition comprising (i) a VEGFR-death ligand polypeptide and (ii) a pharmaceutical acceptable carrier. Pharmaceutical kits optionally comprise an instruction stating that the pharmaceutical composition can or should be used for treating a cancer wherein VEGF expression is up-regulated.

The kits according to the present invention may further comprise a reagent for performing mass spectrometry. Such reagents are well known to those skilled in the art and include, for example, a probe or a chip.

Additional kit embodiments of the present invention include optional functional components that would allow one of ordinary skill in the art to perform any of the method variations described herein.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

As can be appreciated from the disclosure above, the present invention has a wide variety of applications. The invention is further illustrated by the following examples, which are only illustrative and are not intended to limit the definition and scope of the invention in any way.

XI. Examples

Example 1

Material and Methods

1. General Recombinant DNA Methods

Unless otherwise indicated, for generating nucleic acids encoding the fusion proteins of the present invention and for expression of the fusion proteins, routine techniques in the field of recombinant genetics were employed. Basic texts disclosing the general methods of use in this invention include Sambrook & Russell, *Molecular Cloning, A Laboratory Manual* (3rd Ed, 2001); Kriegler, *Gene Transfer and Expression: A Laboratory Manual* (1990); and *Current Protocols in Molecular Biology* (Ausubel et al., eds., 1994-1999).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

2. Cell Lines and Tissue Culture

Cos-7 cells were obtained from the UCSF Cell Culture Facility. Cells were grown in DME-H21 medium supplemented with 10% fetal bovine serum and penicillin/streptomycin, in a tissue culture incubator at 37° C. with 5% $CO_2$.

T-47D human breast cancer cells were obtained from the UCSF Cell Culture Facility. Cells were grown in RPMI-1640 medium supplemented with insulin (0.2 U/mL), 10% fetal bovine serum, and penicillin/streptomycin, in a tissue culture incubator at 37° C. with 5% $CO_2$.

Jurkat E6.1 cells were obtained from the UCSF Cell Culture Facility. Cells were grown in RPMI-1640 medium supplemented 10% fetal bovine serum, and penicillin/streptomycin, in a tissue culture incubator at 37° C. with 5% $CO_2$.

U87MG and U373 are human glioblastoma cell line that were obtained from the American Type Culture Collection (ATCC; Mannassas, Va. 20108, USA). Both are cultured in MEM Eagle's with Earl's BSS medium, supplemented with 10% fetal calf serum and antibiotics. U373 cells are resistant to Fas receptor-mediated apoptosis, while U87MG cells are sensitive (Rieger et al., 1998, *FEBS Lett* 427:124-128; Yount et al., 1999, *Cancer Res* 59:1362-1365).

DU145 is a human prostate cancer cell line. DU145 was obtained from the ATCC and cultured in MEM Eagle's with Earl's BSS medium, supplemented with 10% fetal calf serum and antibiotics.

Human umbilical vein endothelial cells (HUVEC) were obtained from Clonetics and cultured in manufacturer's supplied medium EGM-2 supplemented with fetal calf serum, hydrocortisone, hFGF, IGF, and ascorbic acid. Bovine adrenal cortical endothelial cells (microvascular cells) were obtained from Dr. Richard Weiner at University of California at San Francisco. These cells were cultured in DME H-16 with 1 g/L glucose, supplemented with 10% fetal calf serum and antibiotics (Ferrara et al., 1991, Endocrinology 129:896-900).

3. Western Blotting

Antibody against the extracellular domain of VEGFR-2 was purchased from Becton-Dickinson/Pharmingen (#555307). The rat monoclonal antibody was used for Western blotting at a final concentration of 0.5 micrograms/mL. The secondary antibody was goat anti-rat IgG HRP-conjugated antibody purchased from Santa Cruz Biotechnology (#SC-2065) and used at a final concentration of 0.4 micrograms/mL. Bands were visualized using chemiluminescence (ECL reagents from Amersham).

4. PCR Methods

PCR was used to amplify a fragment of human FasL encoding amino acids 139-281. The sense primer (purchased from the UCSF Biomedical Core) was: 5'-GGGCTCGAGGGAC-TAGTGAAAAAAAGGAGCTGAGGAAAGTGGCCCAT-3' (SEQ ID NO:31), which includes XhoI and SpeI sites on the 5' end. The antisense primer (purchased from the UCSF Biomedical Core) was: 5'-GGGTCTAGATCTTAGAGCT-TATATAAGCCGAAAAACGTCTG-3' (SEQ ID NO:32), which includes a BglII site and an XbaI site on the 3' end. The template was pOTB7/hFasL (purchased from ATCC); the DNA polymerase was Pfu (Stratagene); and the dNTPs were from Roche.

PCR conditions: Template pOTB7/hFasL: 2.0 micrograms; Primers: 100 pMol; dNTPs: 20 nMol; Pfu: 2.5 Units; First cycle: 95° C. for 5'; 95° C. to 35° C. over 10'; 72° C. for 5'; Cycles 2-11: 95° C. for 45"; 60° C. for 45"; 72° C. for 60". A 440 bp PCR fragment was purified by agarose gel chromatography, purified with the Gel Extraction kit (Qiagen), and subcloned into the pBJ vector at the XhoI/XbaI restriction sites.

5. Apoptosis Analysis

Apoptosis and cytotoxicity was assayed by three assays: cell counting, FACS analysis of Annexin V positive cells, and LDH (lactate dehydrogenase) release. For cell counting of Jurkat cells, 100 uL of cell suspension was mixed with an equal volume of Trypan blue stain (0.4%), and kept at room temperature for 2 minutes. Live cells were counted using a hemocytometer in triplicate. Mean number of cells/visual field and SEM were calculated using InStat statistical software. For FACS analysis, the Annexin-V-Fluos kit from Roche was used according to the manufacturer's protocol. Briefly, after treatment with FlkFasL or control conditioned medium±VEGF-165 (2 nM, from Peprotech), Jurkat cells were pelleted and resuspended in 100 μL of Annexin-V-Fluos labeling solution (FITC-Annexin V plus propidium iodide) for 15 minutes at room temperature. FACS analysis was performed on a Becton Dickinson FACSCalibur™ using CellQuest Software, with gating to distinguish Annexin V-positive (apoptotic) versus negative cells, and propidium iodide-positive (i.e. necrotic) versus negative cells. The percent of the cell population that was apototic (Annexin-V-positive and propidium iodide-negative) was determined. For LDH release assays, the LDH Cytotoxicity Detection kit from Roche was used according to the manufacturer's protocol. Briefly, after 48 hours treatment with FlkFasL or control conditioned medium±VEGF-165 (2 nM), cell culture supernatants were centrifuged 500 g for 3 minutes to pellet cell debris. 25 μL of supernatant in triplicate was mixed with LDH detection reagent, and LDH activity quantified by measuring absorbance at 492 nM. Mean and SEM was calculated using InStat statistical software.

Example 2

Construction of Nucleic Acids Encoding a Chimeric Mouse/Human VEGFR/FasL Fusion Protein The pBJ plasmid encoding FlkFasL, pBJ/Flk(D1-D3)+FasL(139-281), was constructed in a stepwise manner. First, PCR was performed to amplify the human FasL sequence encoding amino acids 139-281 with flanking 5' Xho I/Spe 1 and 3' Bgl II/Xba I sites. The PCR fragment was digested with Xho I and Xba I, and subcloned into the pBJ mammalian expression vector at Xho I and Xba I sites to create pBJ/hFasL (139-281) (FIG. 6). This plasmid was then cut with Xho I, and into it was subcloned the Xho I/Xho I fragment from the plasmid LNCX/Flk(1-3)HA, which included the Flk-1 signal sequence and immunoglobulin-like domains 1-3. The resulting plasmid pBJ/Flk(D1-D3)+FasL(139-281) (FIG. 5) contains the FlkFasL nucleotide sequence shown in FIG. 7.

The plasmid pBJ/Flk(D1-D3)+FasL(139-281) encodes the VEGFR-2-FasL fusion protein having an amino acid sequence shown in FIG. 8.

Example 3

Construction of Nucleic Acids Encoding Chimeric Mouse/Human FLAG-VEGFR/FasL Fusion Proteins To generate a plasmid expressing FlkFasL with a FLAG epitope tag, pFLAG/FlkhFasL (D1-D3/139-281; FIG. 6), the pFLAG-CMV-3 vector was purchased from SIGMA. As shown in FIG. 6, the pFLAG-CMV-3 vector was cut with NotI and the ends filled in with Klenow enzyme. The plasmid pBJ/FlkFasL (D1-D3/139-281) was cut with AvaI and blunted with Mung bean nuclease. The resulting fragment encodes the Flk-1 extracellular domain from amino acid Ala-19, at the end of the signal sequence, to Ser-336 at the end of domain 3. Ligation of the AvaI/Mung fragment into NotI/Klenow-treated pFLAG-CMV-3 produces pFLAG-Flk(D1-D3), in which the Flk-1 sequence is placed in-frame downstream of the nucleotides encoding the FLAG epitope tag. To complete the assembly of the FlkFasL cDNA in the pFLAG vector, the BspEI/Bgl II fragment from pBJ/FlkFasL (D1-D3/139-281) was subcloned in. The final plasmid, pFLAG-Flk-FasL, encodes FlkFasL with an N-terminal FLAG epitope tag.

R1[D2]FasL protein consists of the second domain of human VEGFR1 (amino acids 129 to 230: (SDTGRPFVE-MYSEIPEIIHMTEGRELVIPCRVTSP-NITVTLKKFPLDTLIPDGKRIIWDS RKGFIISNATYKEI-GLLTCEATVNGHLYKTNYLTHRQTNTII (SEQ ID NO:55); FIG. 10) fused to the trimerization and Fas receptor binding domains of hFasL (amino acids 139 to 281). A five amino acid linker sequence (ARGTS; SEQ ID NO:7) is present between the VEGFR1 and FasL domains. The linker sequence and the FasL domains are identical to the originally described R2FasL protein. In addition, at the 3' end there is an in-frame preprotrypsin leader sequence and a FLAG epitope tag, which were present in the pFLAG3 vector.

Briefly, a plasmid including the R1[D2]FasL nucleic acid sequence was constructed as follows. The cDNA for VEGFR1 domain 2 was amplified from a VEGFR1-containing plasmid (deVries et al., 1992, *Science* 255:989-991) using as 5' primer (5'-CCCGCGGCCGCCAGTGATACAGGTA-GACCTTTCG-3') SEQ ID NO:56 and as 3' primer (5'-GGC-CTCGAGCTATGATTGTATTGGTTTGTCG-3') SEQ ID NO:57. The resulting PCR fragment was subcloned into NotI and XhoI restriction sites to yield the pFLAG3/R1[D2]FasL plasmid. The nucleic acid sequence of FLAG-tagged r1[D2]FasL is shown in FIG. 9.

Example 4

Generation of Conditioned Medium Containing VEGFR/FasL Fusion Proteins

Figure 11A:
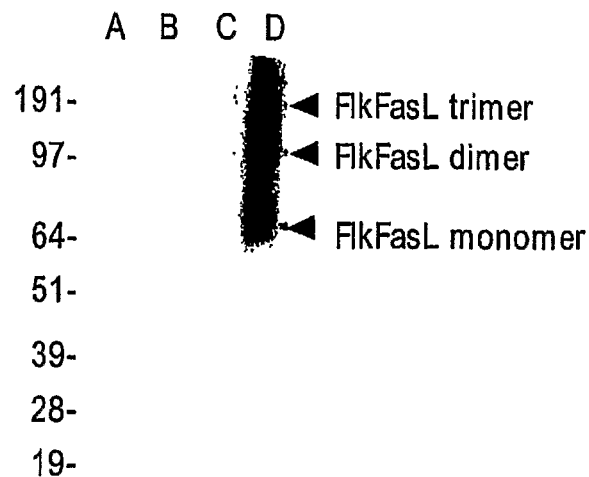
FIG. 11A shows expression of FlkFasL trimers in Cos-7 cells. Cos-7 cells were transfected using a DEAE-dextran protocol with control plasmid pSV/Neo (lane A) or with plasmid pBJ/FlkFasL (lanes B-D). In lane B, cells were transfected with 1 μg plasmid DNA for 30 minutes; lane C, with 3 μg plasmid DNA for 30 minutes; and lane D, with 3 μg plasmid DNA for 3 hours. Forty-four hours after transfection cells were lysed, lysates were electrophoresed by PAGE, and immunoblotted with antibody against the extracellular domain of VEGFR-2.

Cos-7 cells were used to generate conditioned medium containing FlkFasL protein. Cos-7 cells were transfected using a DEAE-dextran protocol modified from Sambrook & Russell, *Molecular Cloning, A Laboratory Manual* (3rd Ed, 2001). Briefly, Cos-7 cells grown in 10 cm plates were washed twice in medium without serum or antibiotics. Three mL of medium without serum or antibiotics were added to each plate, and 3 mL of a DEAE-dextran solution to yield a final concentration of DEAE/dextran=0.4 mg/mL. Plasmid DNA (1 to 3 µg of either pBJ/FlkFasL or control plasmid pBJ/Neo encoding only the neomycin resistance gene) was added to each plate, and plates were returned to the incubator. After 30 minutes or 3 hours the DEAE-dextran-DNA solution was aspirated and each plate was washed with complete medium with serum. Twenty-four hours later the medium was changed to serum-free medium (Hybridoma-SFM, GIBCO). Conditioned medium was collected from the plates after 72 hours, filtered through a 0.2 µM filter, and stored at 4° C. for use in experiments. To confirm expression of FlkFasL protein, 48 hours after DEAE-dextran transfection Cos-7 cells were lysed with glycerol/Triton X-100 lysis buffer. Lysates were separated by PAGE and immunoblotted with antibody against the extracellular domain of VEGFR-2 (Pharmingen), confirming expression of FlkFasL at molecular weight sizes consistent with monomers, dimers, and trimers (FIG. 11A).

Figure 11B:
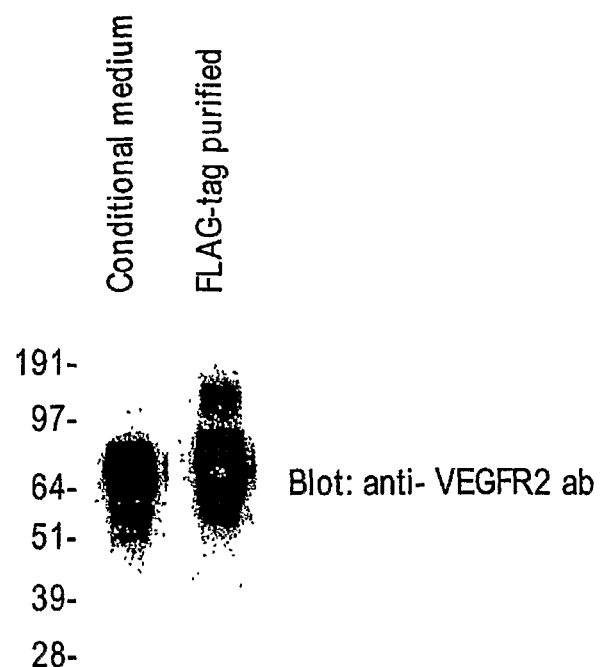
FIG. 11B shows expression of R2FasL by stably transfected CHO cells. The Western blot depicts detection of R2FasL in conditioned medium and after FLAG-tag purification using an anti-VEGFR2 antibody. Details are described in Example 4.

Stably transfected CHO cells secreting FLAG-tagged R2FasL were also generated. Briefly, CHO cells were electroporated with a mixture of pFLAG/R2FasL and the neomycin resistance-expressing vector pBSR-alpha at a ratio of 10:1. Forty-eight hours later cells were split and grown in complete medium with neomycin (1 mg/mL). Colonies growing in neomycin were selected for subculture and their conditioned media were screened for secretion of R2FasL by Western blotting using an antibody against the extracellular domain of VEGFR2 (Pharmingen). A positive clone was reselected by limiting cell dilution and secretion of R2FasL into the conditioned medium reconfirmed by Western blotting. Affinity chromatography of the conditioned medium using anti-FLAG antibody (Sigma) demonstrated expression of the FLAG-tagged R2FasL protein (FIG. 11B).

To produce R1[D2]FasL protein, the pFLAG3/R1[D2]FasL plasmid was transfected into Cos7 cells using DEAE-dextran mediated transfection. Conditioned medium was collected at 96 hours. R1[D2]FasL was purified from the conditioned medium using anti-FLAG antibody affinity chromatography (M2 gel from Sigma) and eluted with FLAG epitope peptide.

Example 5

Cell Killing by a VEGFR/FasL Fusion Protein is Dose-Dependent

Figure 12:
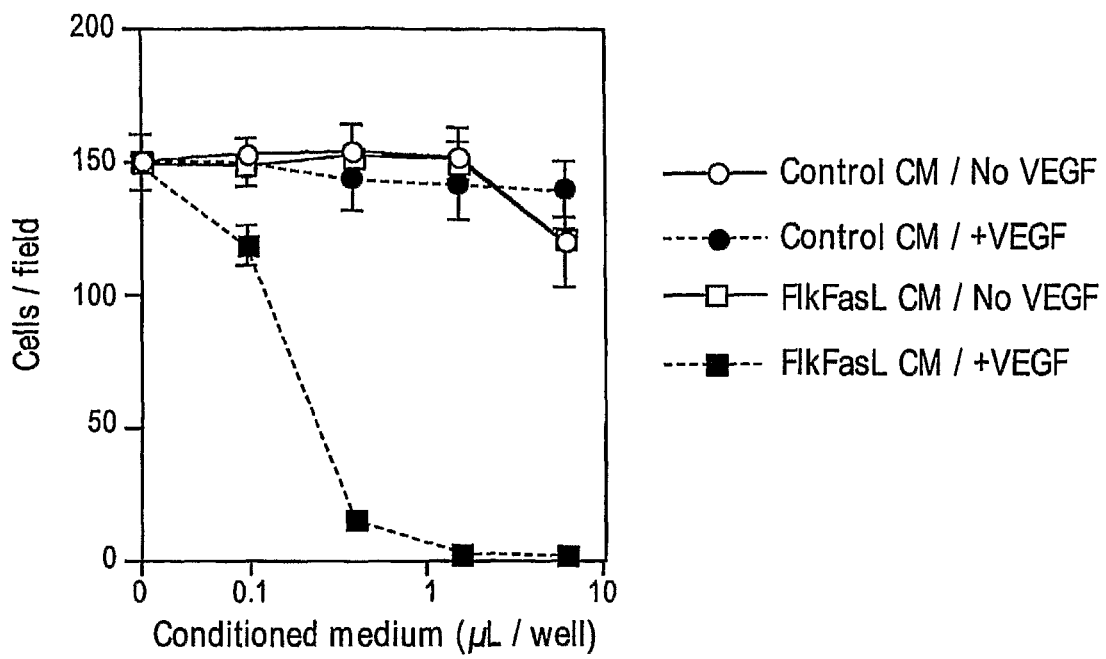
FIG. 12 shows killing of Jurkat cells by FlkFasL in a VEGF-dependent manner. Various amounts of conditioned medium including FlkFasL was added to Jurkat cells. Data are shown as mean number of cells per hemocytometer field±SEM. For some data points the SEM is smaller than the icon used. Details are described in Example 5.

Jurkat cells were plated in 24-well plates (500,000 cells in 500 µl/well) and were treated with increasing volumes of conditioned medium obtained from Cos-7 cells transfected either with either control plasmid pSV/Neo or plasmid pBJ/FlkFasL. Jurkat cells were additionally treated with VEGF-165 (2 nM, from Peprotech) or without VEGF. Thirty-two hours later viable cells were counted after trypan blue staining. A representative result is shown in FIG. 12.

Example 6

Cell Killing by a VEGFR/FasL Fusion Protein is Dependent on the Amount of VEGF

Figure 13:
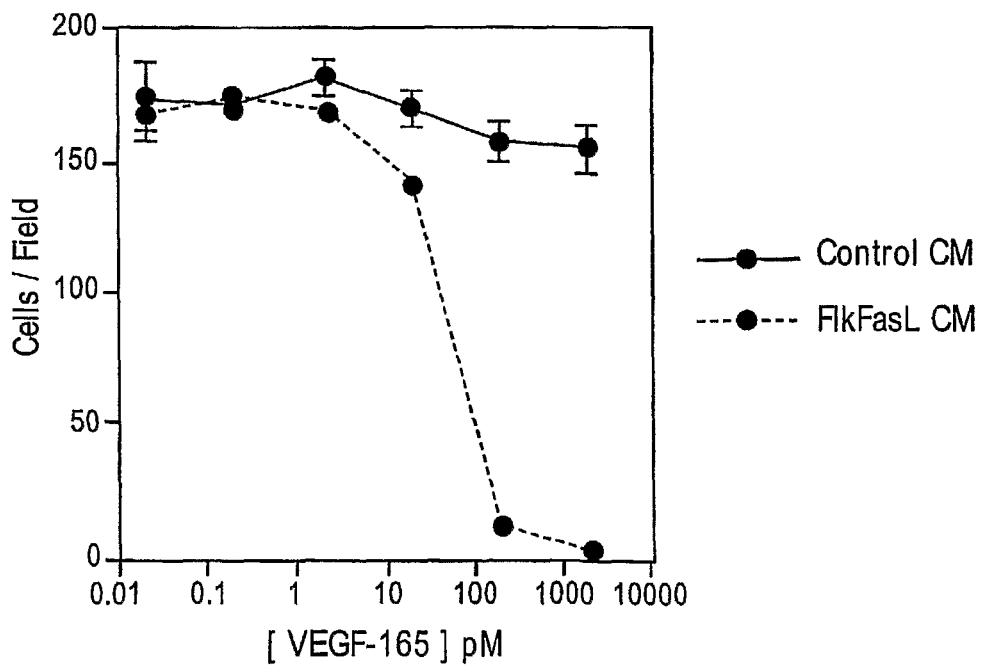
FIG. 13 shows that killing of Jurkat cells by FlkFasL is dependent on the amount of VEGF. Various amounts of VEGF-165 were added to Jurkat cells. Data are shown as mean number of cells per hemocytometer field±SEM. For some data points the SEM is smaller than the icon used. Details are described in Example 6.

Jurkat cells were plated in 24-well plates (500,000 cells in 500 µl/well) and were treated with 25 µL/well of conditioned medium obtained from Cos-7 cells transfected either with control plasmid pSV/Neo or plasmid pBJ/FlkFasL. Jurkat cells were additionally treated with varying amounts of VEGF-165. Twenty-four hours later viable cells were counted after trypan blue staining. A representative result is shown in FIG. 13.

Example 7

FlkFasL Induces Apoptosis in a VEGF-Dependent Manner

Figure 14:
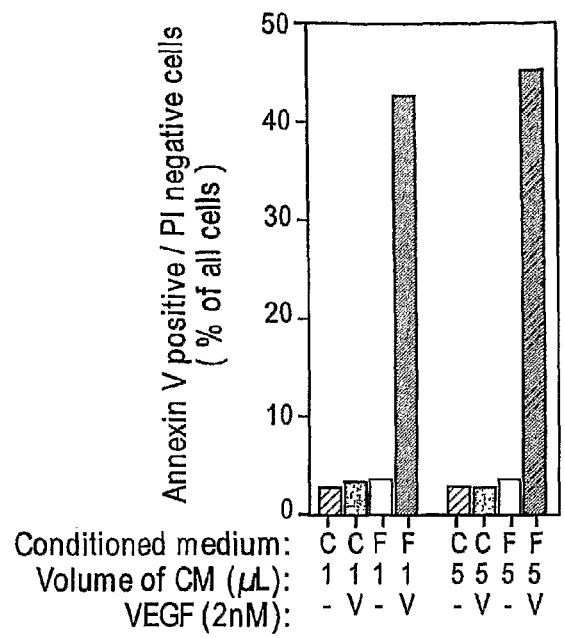
FIG. 14 shows induction of apoptosis by FlkFasL in a VEGF-dependent manner. Jurkat cells were incubated with control conditioned medium (C) or with conditioned medium including FlkFasL (F) in the indicated volumes of 1 μL or 5 μL. Cells were additionally treated with 2 nM VEGF-165 (V) or without (−) for 60 minutes. Induction of apoptosis was assessed by FACS analysis of Annexin V-positive/propidium-iodine negative cells. Details are described in Example 7.

Jurkat cells were plated in 24-well plates (500,000 cells in 500 µl/well) and were treated with either 1 µL/well or 5 µL/well of conditioned medium obtained from Cos-7 cells transfected either with control plasmid pSV/Neo or plasmid pBJ/FlkFasL. Some wells were additionally treated with VEGF-165 (2 nM) for 60 minutes. Induction of apoptosis was assessed by FACS analysis of FITC-Annexin V-positive/propidium-iodide negative cells. A representative result is shown in FIG. 14.

Example 8

VEGFR/FasL Fusion Protein Induces Apoptosis in Breast Cancer Cells

Figure 15:
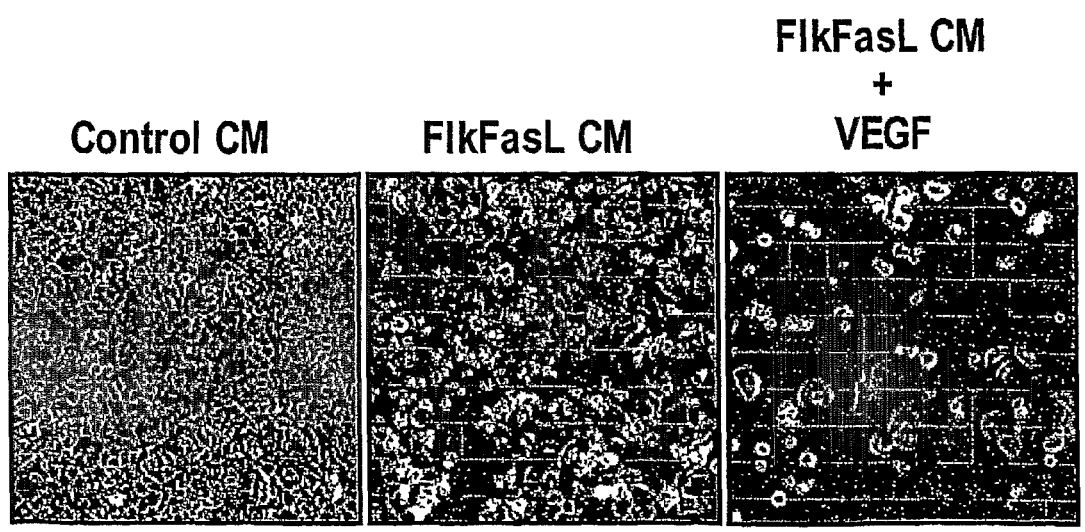
FIG. 15 shows induction of apoptosis in a human breast cancer cell line. T-47D human breast cancer cells were treated with 25 μL of conditioned medium from Cos-7 cells transfected with control plasmid pSV/Neo (Control CM) or plasmid FlkFasL (FlkFasL CM). In the right panel, cells were additionally treated with 2 nM VEGF-165. Cells were photographed 24 hours after treatment. The center panel shows little cell death induced by FlkFasL. The drastically increased cell death in the right panel shows that FlkFasL apoptotic activity is regulated by VEGF. Details are described in Example 8.

T-47D human breast cancer cells were plated in 24-well plates (500,000 cells in 500 µl/well) and grown to confluence. Cells were treated with 25 µL/well of conditioned medium from Cos-7 cells transfected either with control plasmid pSV/Neo or plasmid FlkFasL. Cells were also treated with 2 nM VEGF-165 or without. Cells were photographed 24 hours after treatment. In the presence of endogenous VEGF produced by T-47D cells, FlkFasL induced apoptosis (FIG. 13, center). Upon adding exogenous VEGF, a drastic increase in cell death is observed indicating that FlkFasL apoptotic activity is regulated by VEGF. A representative result is shown in FIG. 15.

Example 9

VEGFR/FasL Fusion Protein Induces Cytotoxicity in Breast Cancer Cells in a VEGF-Dependent Manner T-47D human breast cancer cells were plated in 24-well plates (500,000 cells in 500 μl/well) and grown to confluence. Cells were treated with 25 μL/well of conditioned medium from Cos-7 cells transfected either with control plasmid pSV/Neo or plasmid FlkFasL. Cells were also treated with 2 nM VEGF-165 or without. Forty-eight hours later cytotoxicity was assayed by LDH Cytotoxicity Detection kit (Roche). In the presence of endogenous VEGF produced by T-47D cells, FlkFasL induced cytotoxicity (FIG. 14, lane B). Upon adding exogenous VEGF, a drastic increase in cytotoxicity is observed indicating that FlkFasL apoptotic activity is regulated by VEGF (FIG. 16, lane D).

Figure 16:
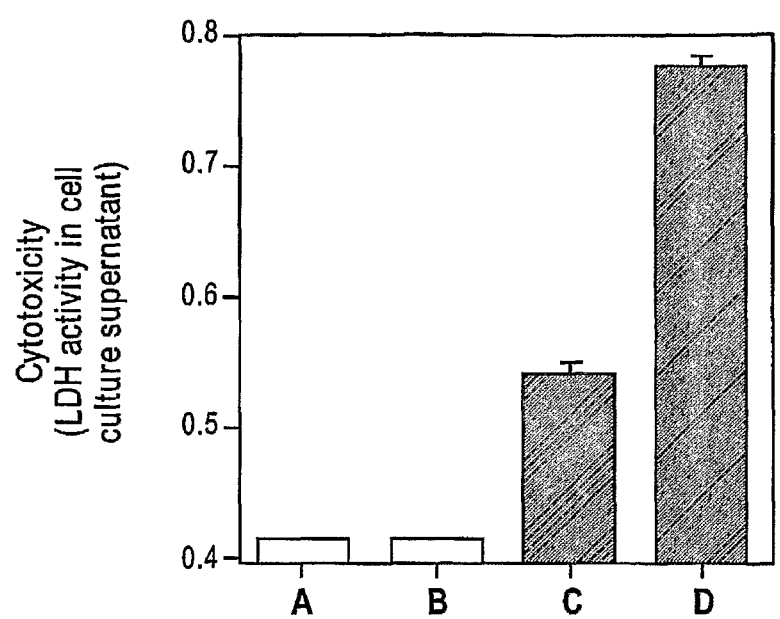
FIG. 16 shows stimulation of cytotoxicity by FlkFasL in a human breast cancer cell line. T-47D human breast cancer cells were treated with 25 μL conditioned medium from Cos-7 cells transfected with control plasmid pSV/Neo (B) or plasmid FlkFasL (C and D). Cells in D were also treated with 2 nM VEGF-165. No conditioned medium was added in lane A. Cells were photographed 24 hours after treatment. Forty-eight hours later cytotoxic response was assayed by quantifying lactate dehydrogenase (LDH) release into the cell culture supernatant. Details are described in Example 9.

Upon comparing the results shown in FIG. 14 (induction of apoptosis in Jurkat cells) to those shown in FIG. 16 (stimulation of cytotoxicity in a breast cancer cell) one notes that the base level of apoptosis induction/cytotoxicity stimulation in the presence of a control conditioned medium with or without added VEGF is similarly low (compare FIG. 16, lanes A and B to FIG. 16). While adding a conditioned medium in the absence of VEGF did not increase apoptotic induction in Jurkat cells (FIG. 14), a marked increase is observed when breast cancer cells are analyzed under similar conditions (FIG. 16, lane C). It is known that breast cancer cells express and secrete endogenous VEGF. Thus, the induction of stimulation of cytotoxic effects in breast cancer cells can be explained by the endogenous VEGF binding to FlkFasL and subsequent binding of the FlkFasL fusion protein (having bound a VEGF polypeptide) to a Fas on the surface of the breast cancer cells. Thus, FIG. 16, lane C describes an apoptotic response to endogenous VEGF that is secreted by a cancer cell and demonstrates the visibility of in vivo administration of the fusion proteins of the present invention. Notably, upon adding exogenous VEGF, the cytotoxic effect is even enhanced.

Example 10

Figure 17A:
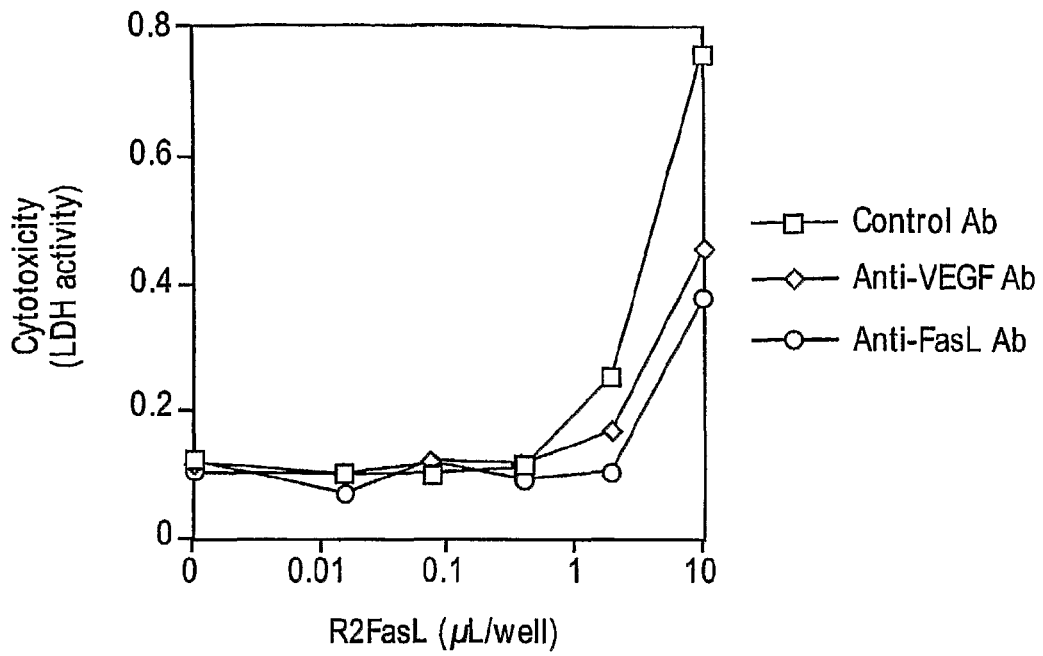
FIG. 17 shows that R2FasL induces cytotoxicity or apoptosis in U87MG human glioblastoma cells and DU145 human prostate cancer cells, but not in U373 human glioblastoma cells. A. R2FasL induces cytotoxicity in U87MG cells, which is inhibited by neutralizing antibodies against VEGF (Anti-VEGF Ab) or FasL (Anti-FasL Ab). B. R2FasL induces cell death in U87MG glioblastoma cells, which is inhibited by neutralizing antibodies against VEGF (Anti-VEGF Ab) or FasL (Anti-FasL Ab). C. R2FasL induces cytotoxicity in DU145 human prostate cancer cells. CM, conditioned medium. D. R2FasL does not induce cytotoxicity in U373 glioblastoma cells. Details are described in Example 10.

R2FasL Induces Cytotoxicity or Apoptosis in U87MG Human Glioblastoma Cells and DU145 Human Prostate Cancer Cells, but not in U373 Human Glioblastoma Cells To investigate if R2FasL induces cytotoxicity in human glioblastoma the following experiment was performed. U87MG human glioblastoma cells were plated in 96-well plates in 100 μL of complete medium with 10% fetal calf serum at 25,000 cells/well, and allowed to grow for 84 hours without change of medium. R2FasL solution (0, 0.01, 0.1, 1, or 10 μL), purified by FLAG epitope tag affinity chromatography, was then added to each well (FIG. 17A). In addition, each well received 300 ng of neutralizing anti-VEGF antibody, neutralizing anti-FasL antibody, or control goat Ig (all from R&S Systems). Twenty-four hours later the cells were assayed for cytotoxicity using the LDH release assay (Roche), in which 10 μL of cell supernatant is mixed with 100 μL LDH reaction mixture in a total reaction volume of 200 μL. Cytotoxicity was assayed spectrophotometrically by measuring absorbance at 492 nm. Inhibition of cytotoxicity by neutralizing antibodies against VEGF or FasL demonstrate that both are required for R2FasL-mediated cytotoxicity (FIG. 17A).

Figure 17B:
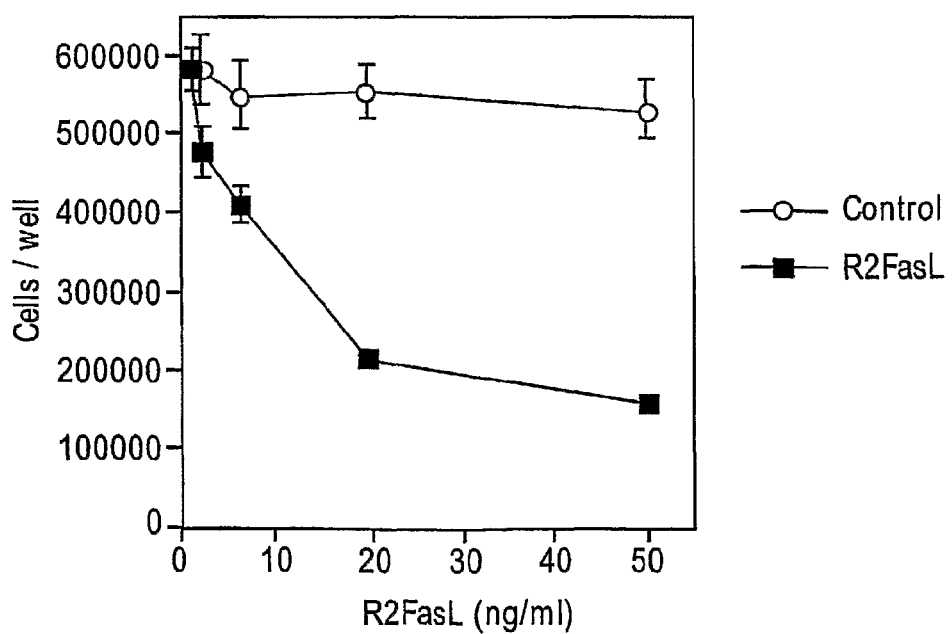

To investigate if R2FasL induces apoptosis in human glioblastoma the following experiment was performed. U87MG human glioblastoma cells were plated in 12-well plates in 500 μL of complete medium with 10% fetal calf serum at approximately 287,500 cells/well. Twenty-four hours later conditioned medium from Cos7 cells transfected with either pFLAG/R2FasL or empty pFLAG vector was added (FIG. 17B). The concentration of R2FasL was determined separately by quantitative immunoblotting using commercially produced rhsFasL as standard (R&S Systems). After 36 more hours, cells were trypsinized, stained with Trypan blue, and counted on a hemocytometer. Data in FIG. 17B are shown as mean±SEM.

Figure 17C:
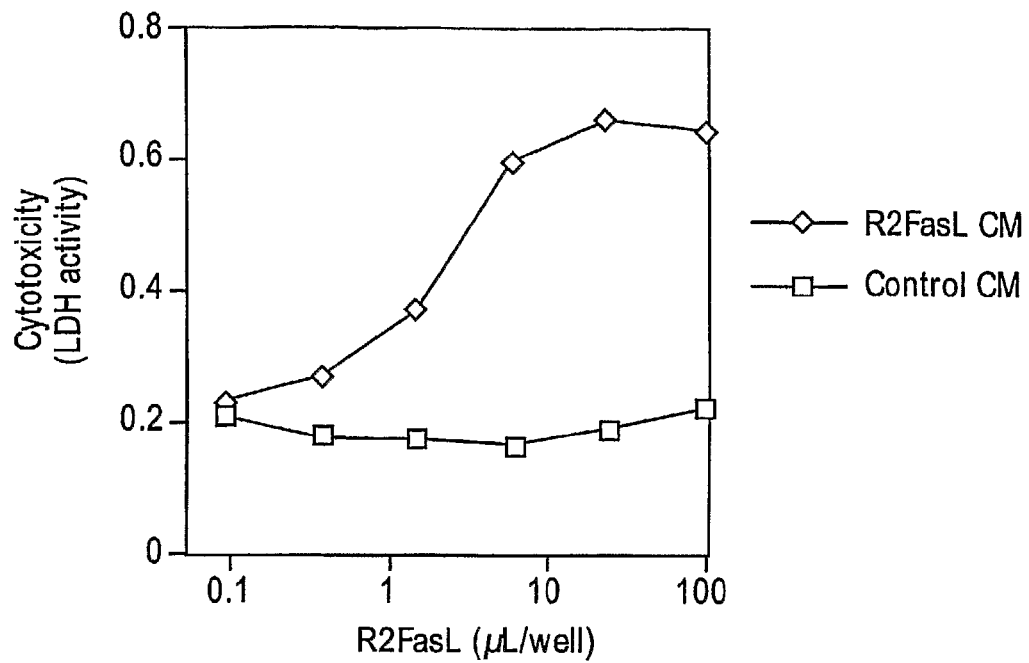

To investigate if R2FasL induces cytotoxicity in human prostate cancer cells the following experiment was performed. DU145 human prostate cancer cells were plated in 24-well plates in 500 μL of complete medium with 10% fetal calf serum and allowed to grow for 54 hours without change of medium. Conditioned medium from Cos7 cells transfected with either pFLAG/R2FasL or empty pFLAG vector was added in the indicated volumes. After 34 more hours cytotoxicity was assayed using the LDH release assay as described above. A representative set of data is shown in FIG. 17C.

Figure 17D:
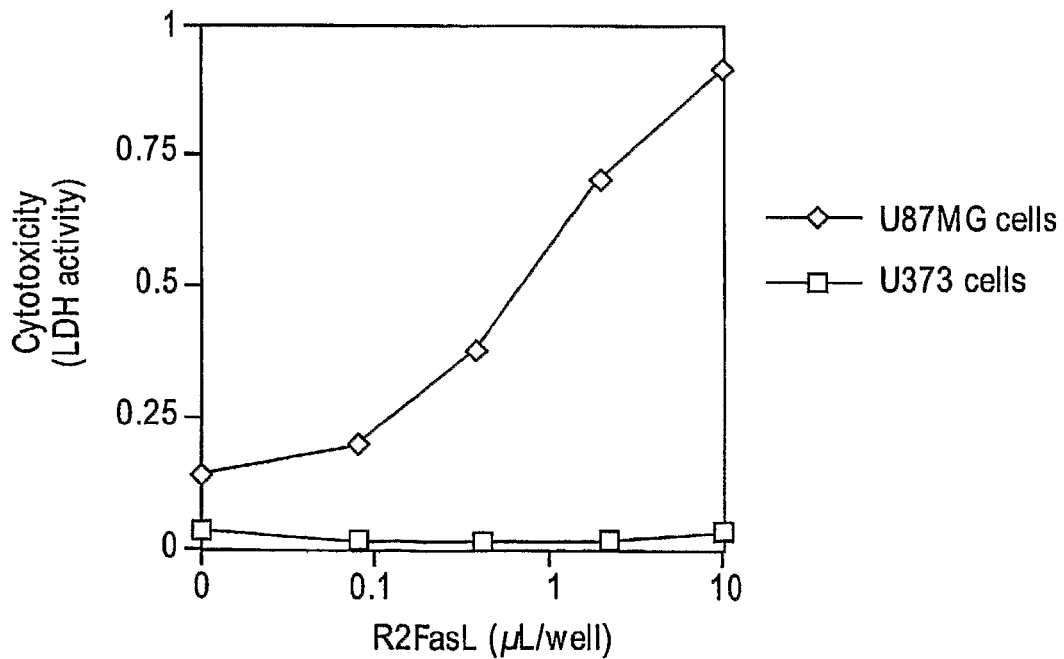

To investigate the specificity of the R2FasL activity on U87MG glioblastoma cells, the cytotoxic effect of R2FasL on the U373 glioblastoma cell line, was analyzed. U373 cells are known to be resistant to Fas receptor-mediated killing, i.e., U373 cells are essentially a negative control to show that R2FasL is not constitutively toxic. U87MG and U373 human glioblastoma cells were plated in 96-well plates in 100 μL of complete medium with 10% fetal calf serum at 25,000 cells/well, and allowed to grow for 96 hours without change of medium. Conditioned medium from Cos7 cells transfected with pFLAG/R2FasL vector was added in the indicated volumes. After 36 more hours cytotoxicity was assayed using the LDH release assay as described herein (FIG. 17D).

Example 11

R1[D2]FasL Induces Apoptosis in a VEGF-Dependent Manner

Figure 18A:
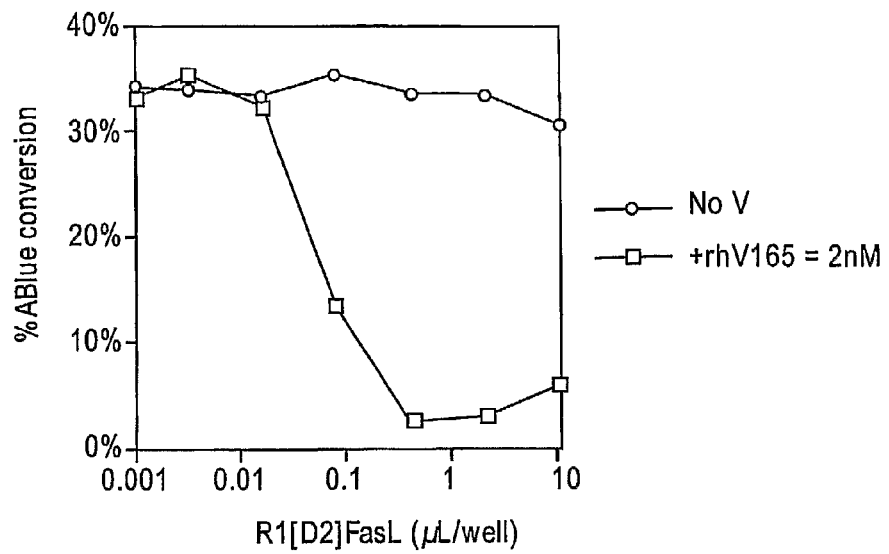
FIG. 18 depicts the apoptotic activity of R1[D2]FasL. A. R1[D2]FasL induces apoptosis in a VEGF-dependent manner. Recombinant human VEGF (rhV165) was added at a concentration of 2 nM. As a control, no VEGF (No V) was added. B. R1[D2]FasL is activated by human and mouse VEGF-165; human VEGF-121, human VEGF:PlGF heterodimer, and human PlGF. C. The $ED_{50}$ for hVEGF-165 on R1[D2]FasL is approximately 100 pM. Details are described in Example 11.

To investigate if R1[D2]FasL induces apoptosis in a VEGF-dependent manner the following experiment was performed. Jurkat E6.1 human T cells were plated in 96-well plates in 100 μL of complete medium with 10% fetal calf serum. Conditioned medium (0.001, 0.01, 0.1, 1, or 10 μL) from Cos7 cells transfected with pFLAG/R1[D2]FasL vector was added in the absence or presence of rhVEGF-165 (final concentration 2 nM). Twenty-two hours later cell viability was assayed using the resazurin assay (AlamarBlue reagent from BioSource). Conversion of AlamarBlue substrate to product by viable cells was determined by adding 20 μL of AlamarBlue to each well and measuring absorbance at 540 nm and 620 nM. Calculation of % conversion of substrate to product was performed according to the manufacturer's protocol. A representative set of data demonstrating that R1[D2]FasL induces apoptosis in a VEGF-dependent manner is shown in FIG. 18A.

Figure 18B:
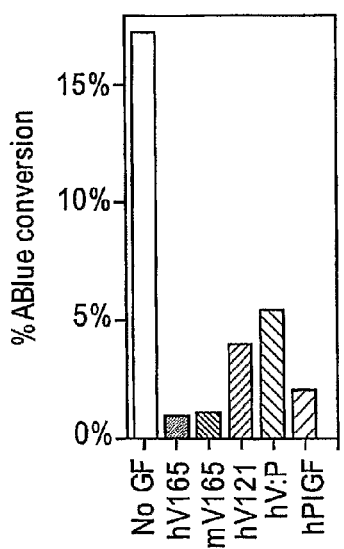

To investigate which growth factors activate R1[D2]FasL the following experiment was performed. Jurkat E6.1 human T cells were plated in 96-well plates in 100 μL of complete medium with 10% fetal calf serum. Conditioned medium from Cos7 cells transfected with pFLAG/R1[D2]FasL vector was added (2 μL/well), in the absence or presence of rhVEGF-165 (recombinant human VEGF-165), rmVEGF-164 (recombinant mouse VEGF-164), rhVEGF-121 (recombinant human VEGF-121), rhVEGF-165/rhPlGF-129 heterodimer, or rhPlGF-129. All growth factors were used at a final concentration of 10 nM, and were from Peprotech or R&D Systems. Nineteen hours later cell viability was assayed using the resazurin assay as described above. Representative data are shown in FIG. 18B. The results show that R1[D2] FasL is activated by all growth factors tested in these experiments.

Figure 21A:
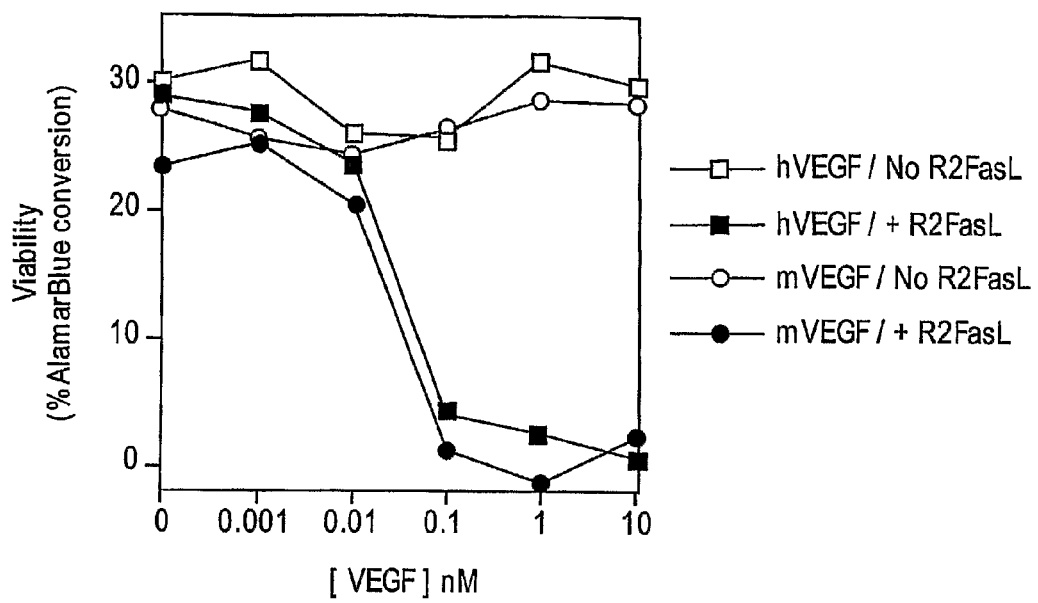
FIG. 21A depicts that R2FasL is activated by both human and mouse VEGF-165 (hVEGF and mVEGF, respectively).

In a similar experiment, the concentration of the growth factors tested was varied. Briefly, Jurkat E6.1 human T cells were plated in 96-well plates in 100 µL of complete medium with 10% fetal calf serum. Conditioned medium from Cos7 cells transfected with either pFLAG/R2FasL vector or empty pFLAG vector was added (1 µL/well), in the absence or presence of rhVEGF-165 or rmVEGF-165 at the final concentrations of 0.001, 0.01, 0.1, 1, and 10 nM. Eighteen hours later cell viability was assayed using the resazurin assay as described herein. The data shown in FIG. 21A demonstrate that human and mouse VEGF-165 similarly activate R2FasL.

Figure 18C:
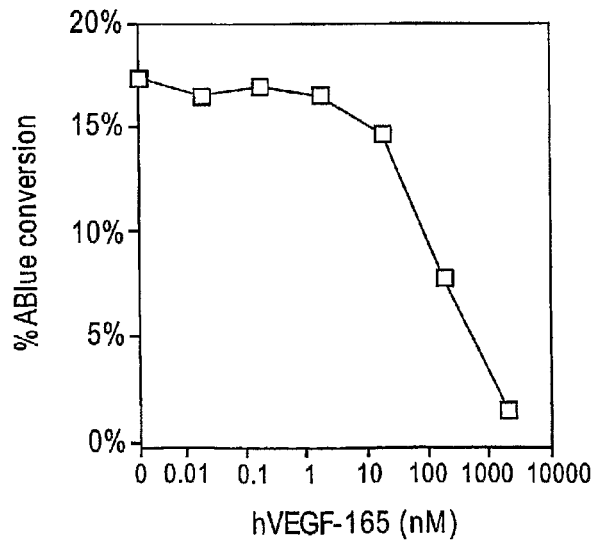

To determine the ED50 for hVEGF-165 on R1[D2]FasL the following experiment was performed. Jurkat E6.1 human T cells were plated in 96-well plates in 100 µL of complete medium with 10% fetal calf serum. Conditioned medium from Cos7 cells transfected with pFLAG/R1[D2]FasL vector was added (2 µL/well), in the absence or presence of rhVEGF-165 at 0, 0.01, 0.1, 1, 10, 100, 1,000, or 10,000 nM. Nineteen hours later cell viability was assayed using the resazurin assay as described above. The ED50 for hVEGF-165 on R1[D2]FasL was found to be approximately 100 pM (FIG. 18C).

Figure 21B:
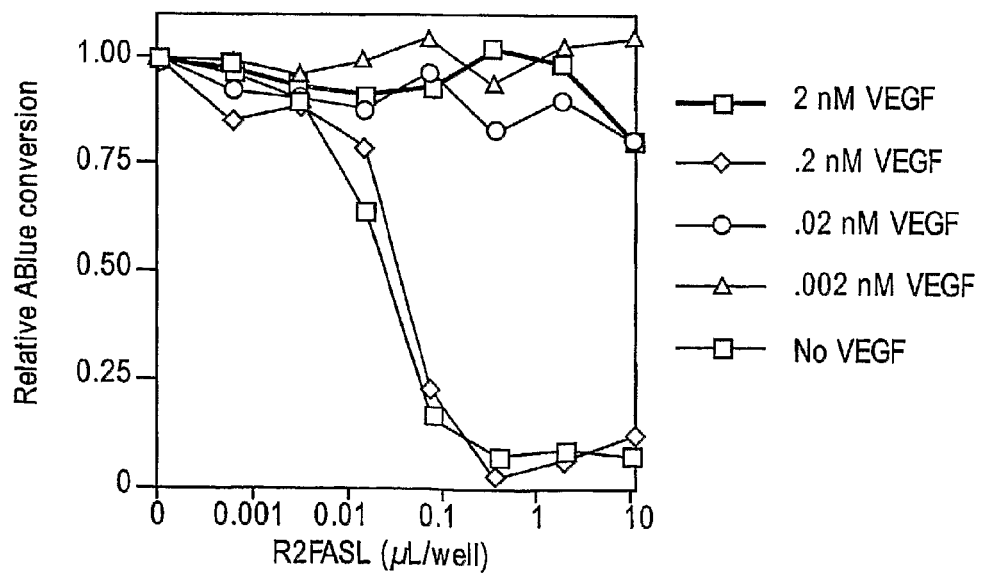
FIG. 21B shows that the ED50 of VEGF-165 is between 20 and 200 pM. Details are described in Example 14.

In a similar experiment the ED50 for hVEGF-165 on R2FasL was determined. Briefly, Jurkat E6.1 human T cells were plated in 96-well plates in 100 µL of complete medium with 10% fetal calf serum. Conditioned medium from Cos7 cells transfected with pFLAG/R2FasL vector was added in the volumes indicated, in the absence or presence of rhVEGF-165 at the final concentrations of 0, 0.02, 0.02, 0.2 and 2 nM. Eighteen hours later cell viability was assayed using the resazurin assay. The ED50 for rhVEGF-165 was between 20 pM and 200 pM (FIG. 21B).

Example 12

R2FasL Activity is Potentiated by Chemotherapeutic Agents

Figure 19A:
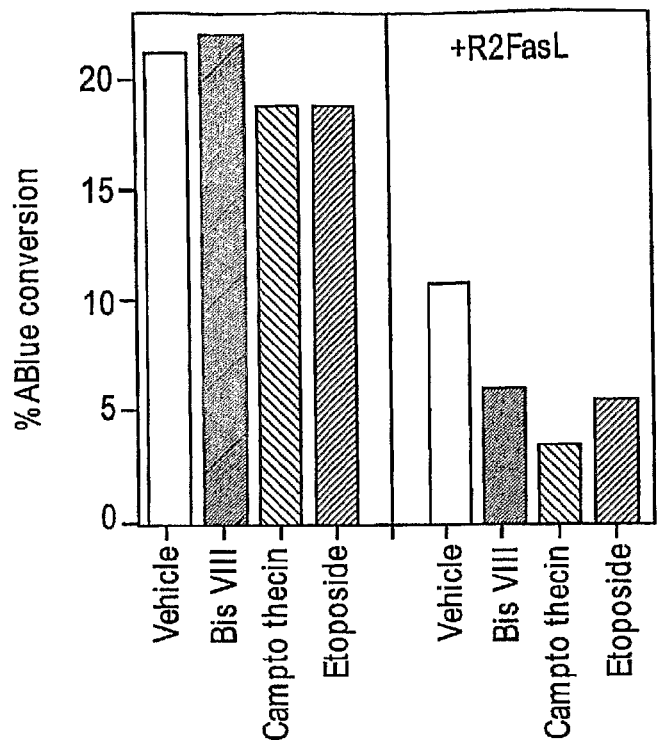
FIG. 19 depicts potentiation of R2FasL activity by chemotherapeutic agents. A. Potentiation of R2FasL apoptotic activity on U87MG glioblastoma cells by BisVIII, camptothecin, and etoposide. B. Potentiation of R2FasL cytotoxic activity on U87MG glioblastoma cells by BisVIII, camptothecin, and etoposide. Details are described in Example 12.
Figure 19B:
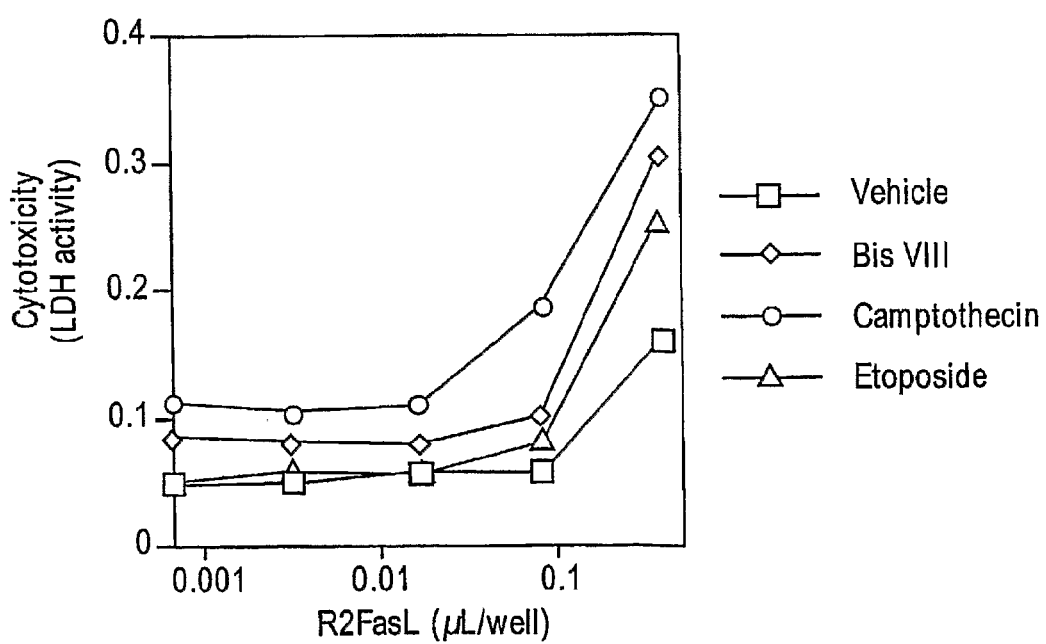

To determine if the activity of R2FasL can be potentiated by chemotherapeutic agents, the following experiments were performed. U87MG human glioblastoma cells were plated in 96-well plates in 100 µL of complete medium with 10% fetal calf serum at 25,000 cells/well. Forty-eight hours later cells were treated with either bisindolylmaleimide VIII (Bis VIII, final concentration 1 µM), camptothecin (final concentration 20 nM), etoposide (final concentration 5 µM), or DMSO vehicle (1 µL/well). Bis VIII, camptothecin, and etoposide (all from Biomol) were dissolved in DMSO and added at 1 µL/well. After 72 hours of drug exposure, cells were treated with FLAG antibody affinity-purified R2FasL solution (10 µL/well), and incubated for an additional 40 hours. Cell viability and cytotoxicity were assayed using the resazurin assay and the LDG release assay, respectively, as described above. The result shown in FIGS. 19A and 19B demonstrates that the activity of R2FasL is potentiated by the chemotherapeutic agents tested in these experiments.

Example 13

Figure 20A:
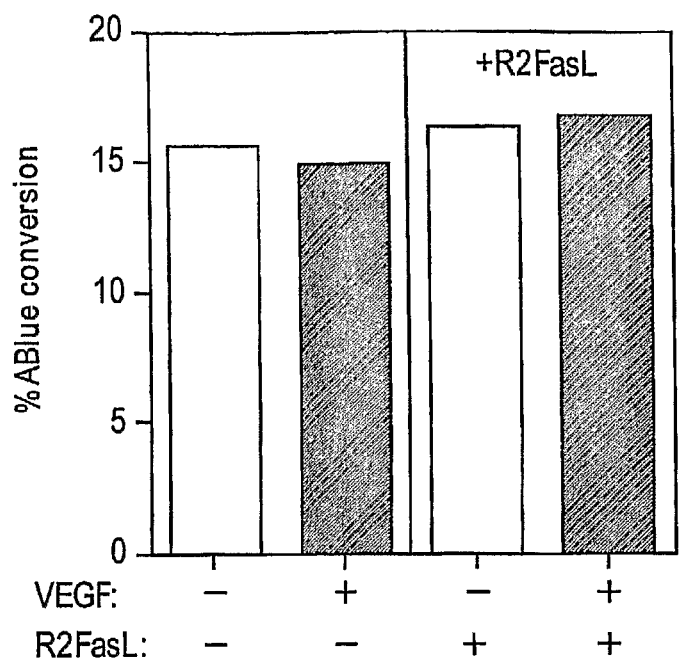
FIG. 20A depicts that R2FasL+VEGF does not induce cytotoxicity in human umbilical vein endothelial cells.

R2FasL does not Induce Cytotoxicity in Macrovascular Endothelial Cells, but does have Activity in Microvascular Endothelial Cells To determine if R2FasL induces cytotoxicity in macrovascular endothelial cells may express different populations of death factor receptors and growth factor receptors. R2FasL may be differentially active in tumor endothelial cells (microvascular) and less toxic to normal macrovascular endotherlial cells, such as arteries and veins. To determine if R2FasL induces cytotoxicity in macrovascular endothelial cells, the following experiments were performed. Human umbilical vein endothelial cells (macrovascular endothelial cells; HUVEC, passage 4, from Clonetics) were plated in 96-well plates in 100 µL of the supplied medium with 10% fetal calf serum but without VEGF. Twenty-four hours later serum starvation was begun (to sensitize cells to death signals) by withdrawing serum. After fifteen hours of serum starvation cells were treated Cos7 cell conditioned medium containing R2FasL (10 µL/well) in the absence or presence of rh VEGF-165 (final concentration 2 nM). After 22 hours of treatment with R2FasL±rhVEGF cell viability was assayed using the resazurin assay as described herein. No effect of R2FasL+VEGF was seen on these macrovascular endothelial cells (FIG. 20A).

Figure 20B:
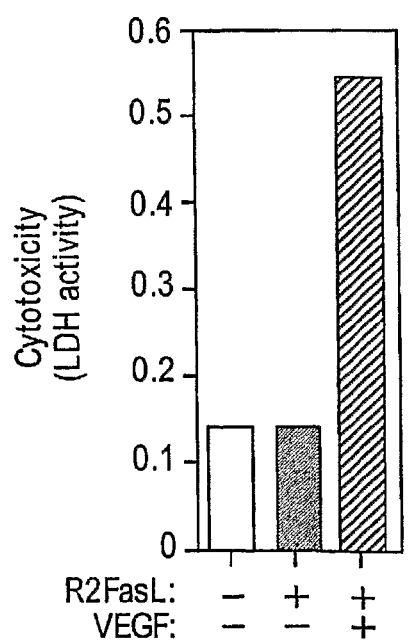
FIG. 20B depicts that R2FasL+VEGF induces cytotoxicity in bovine adrenal cortical endothelial cells (microvascular endothelial cells). Details are described in Example 13.

To determine if R2FasL induces cytotoxicity in microvascular endothelial cells, the following experiments were performed. Bovine adrenal cortical endothelial cells (microvascular endothelial cells) were plated in 96-well plates in 100 µL of complete medium with 1% fetal calf serum. Twenty-two hours later conditioned medium from Cos7 cells transfected with either pFLAG/R2FasL or empty pFLAG vector was added (2 µL/well), in the absence or presence of rhVEGF-165 (final concentration 2 nM). Twenty-four hours later cytotoxicity was assayed using the LDH release assay as described above. FIG. 20B shows that R2FasL and VEGF induce cytotoxicity in adrenal cortical endothelial cells. Thus, R2FasL does not have activity on macrovascular endothelial cells (e.g., HUVEC), but does have activity on microvascular endothelial cells.

Example 14

Testing VEGFR-FasL In Vivo

The activity of a fusion protein of the present invention can also be tested in vivo, for example, in an adjuvant arthritis model. The term "adjuvant arthritis model" is used herein to refer to rats, preferably Wistar-Lewis or other rat strains commonly known to those skilled in the art, in which disease was induced by injecting 0.1 mL Freund's adjuvant into the base of the tail. This adjuvant arthritis model is only one example of an animal model that can be used to test the compounds of the invention. For a review of the three most common animal models, see Oliver & Brahn (1996) J. Rheumatol. 23:56-60, hereby enclosed herein by reference in its entirety, including any drawings, figures, or tables.

A number of animal models have been developed to investigate the function of VEGF in tumor angiogenesis. For example, rat C6 glioma and human U87MG glioblastoma cells secrete VEGF and grow subcutaneously in athymic mice (Saleh et al., *Cancer Res* (1996) 56:393-401; Cheng et al., Proc. Natl. Acad. Sci. USA (1996), 93:8502-8507). The introduction of antisense constructs to VEGF mRNA into these cell lines reduces their in vivo growth, as well as the degree of neovascularization. Monoclonal antibodies against VEGF inhibit the subcutaneous growth of human rhabdomyosarcoma, glioblastoma, leiomyosarcoma (Kim et al., *Nature* (1993), 362:841-844) and fibrosarcoma (Asano et al., *Cancer Res* (1995), 55:5296-5301) in athymic mice. Metastasis of fibrosarcoma (Asano et al., *Cancer Res* (1995), 55:5296-5301) and colon cancer tumors (Warren et al., *J Clin Invest* (1995), 95:1789-1797) was also blocked by anti-VEGF antibodies. Thus, these animal models will be useful for testing the in vivo activities of the fusion proteins of the present invention.

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

All publications and patent applications cited in this specification are herein incorporated by reference as if each individual publication or patent application were specifically and individually indicated to be incorporated by reference.

What is claimed is:

1. A soluble fusion protein which binds to a death receptor and induces apoptosis, the fusion protein comprising:
   (i) a soluble vascular endothelial growth factor receptor-1 (VEGFR-1) polypeptide that binds a vascular endothelial growth factor (VEGF) polypeptide, wherein the VEGFR-1 polypeptide comprises an amino acid sequence at least 95% identical to amino acid residues 129 to 230 of SEQ ID NO: 19; and
   (ii) a soluble human tumor necrosis factor-related apoptosis-inducing ligand (TRAIL) extracellular domain, wherein the C-terminus of the VEGFR-1 polypeptide is linked to the N-terminus of the TRAIL extracellular domain.

2. The fusion protein of claim 1, wherein the VEGFR-1 is a human VEGFR-1.

3. The fusion protein of claim 1, further comprising:
   (iii) an epitope tag.

4. The fusion protein of claim 3, wherein the epitope tag comprises a FLAG-like tag or an HA tag.

5. The fusion protein of claim 4, wherein the epitope tag can be cleaved off.

6. A method of inducing a death receptor-mediated pathway comprising the step of:
   contacting a TRAIL receptor expressing cell with an effective amount of a fusion protein of claim 1, wherein the amount of the fusion protein is effective to induce the TRAIL receptor-mediated pathway.

7. The method of claim 6, which is practiced in vitro.

8. The method of claim 6, which is practiced in vivo.

9. The method of claim 6, wherein the cell is a cancer cell.

10. The method of claim 9, wherein the cancer cell overexpresses VEGF.

11. The method of claim 9, wherein the cancer cell is selected from the group consisting of breast cancer cell, prostate cancer cell, colon cancer cell, lung cancer cell, glioblastoma cell, and ovarian cancer cell.

12. The method of claim 6, wherein the TRAIL receptor-mediated pathway is modulated in a disease selected from the group consisting of rheumatoid arthritis, psoriasis, and macular degeneration.

13. The method of claim 6, further comprising the step of contacting the death receptor expressing cell with a chemotherapeutic agent.

14. The method of claim 13, wherein the chemotherapeutic agent is selected from the group consisting of camptothecin, etoposide, bisindolylmaleimide VIII, cisplatin, taxol, doxorubicin, temozolomide, bortezomid, LY294002, and valproic acid.

15. A pharmaceutical composition comprising:
   (i) the fusion protein of claim 1; and
   (ii) a pharmaceutically acceptable excipient, carrier and/or diluent.

* * * * *

SEQUENCE LISTING

```
<160> NUMBER OF SEQ ID NOS: 57

<210> SEQ ID NO 1
<211> LENGTH: 334
<212> TYPE: PRT
<213> ORGANISM: Homo sapiens
<220> FEATURE:
<223> OTHER INFORMATION: human vascular endothelial growth factor (VEGF,
      VPF, vasculotropin) receptor-2 (VEGFR-2), kinase domain receptor
      (KDR), fetal liver kinase 1 (Flk-1), type III receptor
      tyrosine kinase, kinase NYK extracellular domain

<400> SEQUENCE: 1

Met Gln Ser Lys Val Leu Leu Ala Val Ala Leu Trp Leu Cys Val Glu
  1               5                  10                  15

Thr Arg Ala Ala Ser Val Gly Leu Pro Ser Val Ser Leu Asp Leu Pro
                 20                  25                  30

Arg Leu Ser Ile Gln Lys Asp Ile Leu Thr Ile Lys Ala Asn Thr Thr
             35                  40                  45

Leu Gln Ile Thr Cys Arg Gly Gln Arg Asp Leu Asp Trp Leu Trp Pro
         50                  55                  60

Asn Asn Gln Ser Gly Ser Glu Gln Arg Val Glu Val Thr Glu Cys Ser
 65                  70                  75                  80

Asp Gly Leu Phe Cys Lys Thr Leu Thr Ile Pro Lys Val Ile Gly Asn
                 85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
            115                 120                 125

Val Ser Asp Gln His Gly Val Val Tyr Ile Thr Glu Asn Lys Asn Lys
        130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
```

```
                260                 265                 270
Val Asn Arg Asp Leu Lys Thr Gln Ser Gly Ser Glu Met Lys Lys Phe
            275                 280                 285

Leu Ser Thr Leu Thr Ile Asp Gly Val Thr Arg Ser Asp Gln Gly Leu
        290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser
                325                 330

<210> SEQ ID NO 2
<211> LENGTH: 336
<212> TYPE: PRT
<213> ORGANISM: Mus musculus
<220> FEATURE:
<223> OTHER INFORMATION: mouse vascular endothelial growth factor (VEGF,
      VPF, vasculotropin) receptor-2 (VEGFR-2), kinase domain receptor
      (KDR), fetal liver kinase 1 (Flk-1), type III receptor
      tyrosine kinase, kinase NYK extracellular domain

<400> SEQUENCE: 2

Met Glu Ser Lys Ala Leu Leu Ala Val Ala Leu Trp Phe Cys Val Glu
1               5                   10                  15

Thr Arg Ala Ala Ser Val Gly Leu Pro Gly Asp Phe Leu His Pro Pro
            20                  25                  30

Lys Leu Ser Thr Gln Lys Asp Ile Leu Thr Ile Leu Ala Asn Thr Thr
        35                  40                  45

Leu Gln Ile Thr Cys Arg Gly Gln Arg Asp Leu Asp Trp Leu Trp Pro
    50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val
                85                  90                  95

Gly Asn Asp Thr Gly Ala Tyr Lys Cys Ser Tyr Arg Asp Val Asp Ile
            100                 105                 110

Ala Ser Thr Val Tyr Val Tyr Val Arg Asp Tyr Arg Ser Pro Phe Ile
        115                 120                 125

Ala Ser Val Ser Asp Gln His Gly Ile Val Tyr Ile Thr Glu Asn Lys
    130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
                165                 170                 175

Asn Arg Ile Ser Trp Asp Ser Glu Ile Gly Phe Thr Leu Pro Ser Tyr
            180                 185                 190

Met Ile Ser Tyr Ala Gly Met Val Phe Cys Glu Ala Lys Ile Asn Asp
        195                 200                 205

Glu Thr Tyr Gln Ser Ile Met Tyr Ile Val Val Val Gly Tyr Arg
    210                 215                 220

Ile Tyr Asp Val Ile Leu Ser Pro His Glu Ile Glu Leu Ser Ala
225                 230                 235                 240

Gly Glu Lys Leu Val Leu Asn Cys Thr Ala Arg Thr Glu Leu Asn Val
                245                 250                 255

Gly Leu Asp Phe Thr Trp His Ser Pro Pro Ser Lys Ser His His Lys
            260                 265                 270

Lys Ile Val Asn Arg Asp Val Lys Pro Phe Pro Gly Thr Val Ala Lys
```

```
              275                 280                 285
Met Phe Leu Ser Thr Leu Thr Ile Glu Ser Val Thr Lys Ser Asp Gln
        290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
                325                 330                 335

<210> SEQ ID NO 3
<211> LENGTH: 334
<212> TYPE: PRT
<213> ORGANISM: Rattus norvegicus
<220> FEATURE:
<223> OTHER INFORMATION: rat vascular endothelial growth factor (VEGF,
      VPF, vasculotropin) receptor-2 (VEGFR-2), kinase domain receptor
      (KDR), fetal liver kinase 1 (Flk-1), type III receptor
      tyrosine kinase, kinase NYK extracellular domain

<400> SEQUENCE: 3

Met Glu Ser Arg Ala Leu Leu Ala Val Ala Leu Trp Phe Cys Val Glu
  1               5                  10                  15

Thr Arg Ala Ala Ser Val Gly Leu Pro Gly Asp Ser Leu His Pro Pro
                 20                  25                  30

Lys Leu Ser Thr Gln Lys Asp Ile Leu Thr Ile Leu Ala Asn Thr Thr
             35                  40                  45

Leu Gln Ile Thr Cys Arg Gly Gln Arg Asp Leu Asp Trp Leu Trp Pro
         50                  55                  60

Asn Thr Pro Arg Asp Ser Glu Glu Arg Val Leu Val Thr Glu Cys Gly
 65                  70                  75                  80

Asp Ser Ile Phe Cys Lys Thr Leu Thr Val Pro Arg Val Val Gly Asn
                 85                  90                  95

Asp Thr Gly Ala Tyr Lys Cys Phe Tyr Arg Asp Thr Asp Val Ser Ser
                100                 105                 110

Ile Val Tyr Val Tyr Val Gln Asp His Arg Ser Pro Phe Ile Ala Ser
            115                 120                 125

Val Ser Asp Glu His Gly Ile Val Tyr Ile Thr Glu Asn Lys Asn Lys
        130                 135                 140

Thr Val Val Ile Pro Cys Arg Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Glu Lys Gly Phe Thr Ile Pro Ser Tyr Met Ile
                180                 185                 190

Ser Tyr Ala Gly Met Val Phe Cys Glu Ala Lys Ile Asn Asp Glu Thr
            195                 200                 205

Tyr Gln Ser Ile Met Tyr Ile Val Leu Val Val Gly Tyr Arg Ile Tyr
        210                 215                 220

Asp Val Val Leu Ser Pro Pro His Glu Ile Glu Leu Ser Ala Gly Glu
225                 230                 235                 240

Lys Leu Val Leu Asn Cys Thr Ala Arg Thr Glu Leu Asn Val Gly Leu
                245                 250                 255

Asp Phe Ser Trp Gln Phe Pro Ser Ser Lys His Gln His Lys Lys Ile
                260                 265                 270

Val Asn Arg Asp Val Lys Ser Leu Pro Gly Thr Val Ala Lys Met Phe
            275                 280                 285

Leu Ser Thr Leu Thr Ile Asp Ser Val Thr Lys Ser Asp Gln Gly Glu
```

```
            290                 295                 300
Tyr Thr Cys Thr Ala Tyr Ser Gly Leu Met Thr Lys Lys Asn Lys Thr
305                 310                 315                 320

Phe Val Arg Val His Thr Lys Pro Phe Ile Ala Phe Gly Ser
                325                 330
```

<210> SEQ ID NO 4
<211> LENGTH: 315
<212> TYPE: PRT
<213> ORGANISM: Homo sapiens
<220> FEATURE:
<223> OTHER INFORMATION: human vascular endothelial growth factor (VEGF, VPF, vasculotropin) receptor-2 (VEGFR-2), kinase domain receptor (KDR), fetal liver kinase 1 (Flk-1), type III receptor tyrosine kinase, kinase NYK extracellular domain

<400> SEQUENCE: 4

```
Ala Ser Val Gly Leu Pro Ser Val Ser Leu Asp Leu Pro Arg Leu Ser
 1               5                  10                  15

Ile Gln Lys Asp Ile Leu Thr Ile Lys Ala Asn Thr Thr Leu Gln Ile
                20                  25                  30

Thr Cys Arg Gly Gln Arg Asp Leu Asp Trp Leu Trp Pro Asn Asn Gln
            35                  40                  45

Ser Gly Ser Glu Gln Arg Val Glu Val Thr Glu Cys Ser Asp Gly Leu
        50                  55                  60

Phe Cys Lys Thr Leu Thr Ile Pro Lys Val Ile Gly Asn Asp Thr Gly
65                  70                  75                  80

Ala Tyr Lys Cys Phe Tyr Arg Glu Thr Asp Leu Ala Ser Val Ile Tyr
                85                  90                  95

Val Tyr Val Gln Asp Tyr Arg Ser Pro Phe Ile Ala Ser Val Ser Asp
            100                 105                 110

Gln His Gly Val Val Tyr Ile Thr Glu Asn Lys Asn Lys Thr Val Val
        115                 120                 125

Ile Pro Cys Leu Gly Ser Ile Ser Asn Leu Asn Val Ser Leu Cys Ala
130                 135                 140

Arg Tyr Pro Glu Lys Arg Phe Val Pro Asp Gly Asn Arg Ile Ser Trp
145                 150                 155                 160

Asp Ser Lys Lys Gly Phe Thr Ile Pro Ser Tyr Met Ile Ser Tyr Ala
                165                 170                 175

Gly Met Val Phe Cys Glu Ala Lys Ile Asn Asp Glu Ser Tyr Gln Ser
            180                 185                 190

Ile Met Tyr Ile Val Val Val Gly Tyr Arg Ile Tyr Asp Val Val
        195                 200                 205

Leu Ser Pro Ser His Gly Ile Glu Leu Ser Val Gly Glu Lys Leu Val
    210                 215                 220

Leu Asn Cys Thr Ala Arg Thr Glu Leu Asn Val Gly Ile Asp Phe Asn
225                 230                 235                 240

Trp Glu Tyr Pro Ser Ser Lys His Gln His Lys Lys Leu Val Asn Arg
                245                 250                 255

Asp Leu Lys Thr Gln Ser Gly Ser Glu Met Lys Lys Phe Leu Ser Thr
            260                 265                 270

Leu Thr Ile Asp Gly Val Thr Arg Ser Asp Gln Gly Leu Tyr Thr Cys
        275                 280                 285

Ala Ala Ser Ser Gly Leu Met Thr Lys Lys Asn Ser Thr Phe Val Arg
    290                 295                 300

Val His Glu Lys Pro Phe Val Ala Phe Gly Ser
```

<210> SEQ ID NO 5
<211> LENGTH: 317
<212> TYPE: PRT
<213> ORGANISM: Mus musculus
<220> FEATURE:
<223> OTHER INFORMATION: mouse vascular endothelial growth factor (VEGF, VPF, vasculotropin) receptor-2 (VEGFR-2), kinase domain receptor (KDR), fetal liver kinase 1 (Flk-1), type III receptor tyrosine kinase, kinase NYK extracellular domain

<400> SEQUENCE: 5

```
Ala Ser Val Gly Leu Pro Gly Asp Phe Leu His Pro Pro Lys Leu Ser
  1               5                  10                  15

Thr Gln Lys Asp Ile Leu Thr Ile Leu Ala Asn Thr Thr Leu Gln Ile
             20                  25                  30

Thr Cys Arg Gly Gln Arg Asp Leu Asp Trp Leu Trp Pro Asn Ala Gln
         35                  40                  45

Arg Asp Ser Glu Glu Arg Val Leu Val Thr Glu Cys Gly Gly Gly Asp
     50                  55                  60

Ser Ile Phe Cys Lys Thr Leu Thr Ile Pro Arg Val Val Gly Asn Asp
 65                  70                  75                  80

Thr Gly Ala Tyr Lys Cys Ser Tyr Arg Asp Val Asp Ile Ala Ser Thr
                 85                  90                  95

Val Tyr Val Tyr Val Arg Asp Tyr Arg Ser Pro Phe Ile Ala Ser Val
            100                 105                 110

Ser Asp Gln His Gly Ile Val Tyr Ile Thr Glu Asn Lys Asn Lys Thr
        115                 120                 125

Val Val Ile Pro Cys Arg Gly Ser Ile Ser Asn Leu Asn Val Ser Leu
    130                 135                 140

Cys Ala Arg Tyr Pro Glu Lys Arg Phe Val Pro Asp Gly Asn Arg Ile
145                 150                 155                 160

Ser Trp Asp Ser Glu Ile Gly Phe Thr Leu Pro Ser Tyr Met Ile Ser
                165                 170                 175

Tyr Ala Gly Met Val Phe Cys Glu Ala Lys Ile Asn Asp Glu Thr Tyr
            180                 185                 190

Gln Ser Ile Met Tyr Ile Val Val Val Gly Tyr Arg Ile Tyr Asp
        195                 200                 205

Val Ile Leu Ser Pro Pro His Glu Ile Glu Leu Ser Ala Gly Glu Lys
    210                 215                 220

Leu Val Leu Asn Cys Thr Ala Arg Thr Glu Leu Asn Val Gly Leu Asp
225                 230                 235                 240

Phe Thr Trp His Ser Pro Pro Ser Lys Ser His His Lys Lys Ile Val
                245                 250                 255

Asn Arg Asp Val Lys Pro Phe Pro Gly Thr Val Ala Lys Met Phe Leu
            260                 265                 270

Ser Thr Leu Thr Ile Glu Ser Val Thr Lys Ser Asp Gln Gly Glu Tyr
        275                 280                 285

Thr Cys Val Ala Ser Ser Gly Arg Met Ile Lys Arg Asn Arg Thr Phe
    290                 295                 300

Val Arg Val His Thr Lys Pro Phe Ile Ala Phe Gly Ser
305                 310                 315
```

<210> SEQ ID NO 6
<211> LENGTH: 315
<212> TYPE: PRT

```
<213> ORGANISM: Rattus norvegicus
<220> FEATURE:
<223> OTHER INFORMATION: rat vascular endothelial growth factor (VEGF,
      VPF, vasculotropin) receptor-2 (VEGFR-2), kinase domain receptor
      (KDR), fetal liver kinase 1 (Flk-1), type III receptor
      tyrosine kinase, kinase NYK extracellular domain

<400> SEQUENCE: 6

Ala Ser Val Gly Leu Pro Gly Asp Ser Leu His Pro Pro Lys Leu Ser
 1               5                  10                  15

Thr Gln Lys Asp Ile Leu Thr Ile Leu Ala Asn Thr Thr Leu Gln Ile
            20                  25                  30

Thr Cys Arg Gly Gln Arg Asp Leu Asp Trp Leu Trp Pro Asn Thr Pro
        35                  40                  45

Arg Asp Ser Glu Glu Arg Val Leu Val Thr Glu Cys Gly Asp Ser Ile
    50                  55                  60

Phe Cys Lys Thr Leu Thr Val Pro Arg Val Val Gly Asn Asp Thr Gly
65                  70                  75                  80

Ala Tyr Lys Cys Phe Tyr Arg Asp Thr Asp Val Ser Ser Ile Val Tyr
                85                  90                  95

Val Tyr Val Gln Asp His Arg Ser Pro Phe Ile Ala Ser Val Ser Asp
            100                 105                 110

Glu His Gly Ile Val Tyr Ile Thr Glu Asn Lys Asn Lys Thr Val Val
        115                 120                 125

Ile Pro Cys Arg Gly Ser Ile Ser Asn Leu Asn Val Ser Leu Cys Ala
    130                 135                 140

Arg Tyr Pro Glu Lys Arg Phe Val Pro Asp Gly Asn Arg Ile Ser Trp
145                 150                 155                 160

Asp Ser Glu Lys Gly Phe Thr Ile Pro Ser Tyr Met Ile Ser Tyr Ala
                165                 170                 175

Gly Met Val Phe Cys Glu Ala Lys Ile Asn Asp Glu Thr Tyr Gln Ser
            180                 185                 190

Ile Met Tyr Ile Val Leu Val Gly Tyr Arg Ile Tyr Asp Val Val
        195                 200                 205

Leu Ser Pro Pro His Glu Ile Glu Leu Ser Ala Gly Glu Lys Leu Val
    210                 215                 220

Leu Asn Cys Thr Ala Arg Thr Glu Leu Asn Val Gly Leu Asp Phe Ser
225                 230                 235                 240

Trp Gln Phe Pro Ser Ser Lys His Gln His Lys Lys Ile Val Asn Arg
                245                 250                 255

Asp Val Lys Ser Leu Pro Gly Thr Val Ala Lys Met Phe Leu Ser Thr
            260                 265                 270

Leu Thr Ile Asp Ser Val Thr Lys Ser Asp Gln Gly Glu Tyr Thr Cys
        275                 280                 285

Thr Ala Tyr Ser Gly Leu Met Thr Lys Lys Asn Lys Thr Phe Val Arg
    290                 295                 300

Val His Thr Lys Pro Phe Ile Ala Phe Gly Ser
305                 310                 315

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:linker
      sequence between VEGFR1 and FasL domains

<400> SEQUENCE: 7
```

```
Ala Arg Gly Thr Ser
 1               5

<210> SEQ ID NO 8
<211> LENGTH: 281
<212> TYPE: PRT
<213> ORGANISM: Homo sapiens
<220> FEATURE:
<223> OTHER INFORMATION: human Fas ligand (FasL), tumor necrosis factor
      ligand superfamily member 6 (TNFSF6), apoptosis
      antigen ligand (APTL, APT1LG1), CD178 antigen,
      CD95L protein, death receptor ligand

<400> SEQUENCE: 8

Met Gln Gln Pro Phe Asn Tyr Pro Tyr Pro Gln Ile Tyr Trp Val Asp
 1               5                  10                  15

Ser Ser Ala Ser Ser Pro Trp Ala Pro Pro Gly Thr Val Leu Pro Cys
             20                  25                  30

Pro Thr Ser Val Pro Arg Arg Pro Gly Gln Arg Arg Pro Pro Pro Pro
         35                  40                  45

Pro Pro Pro Pro Pro Leu Pro Pro Pro Pro Pro Pro Pro Pro Leu Pro
     50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

<210> SEQ ID NO 9
<211> LENGTH: 279
<212> TYPE: PRT
<213> ORGANISM: Mus musculus
<220> FEATURE:
<223> OTHER INFORMATION: mouse Fas ligand (FasL), tumor necrosis factor
      ligand superfamily member 6 (TNFSF6), apoptosis
``` antigen ligand (APTL, APT1LG1), CD178 antigen,
CD95L protein, death receptor ligand

<400> SEQUENCE: 9

```
Met Gln Gln Pro Met Asn Tyr Pro Cys Pro Gln Ile Phe Trp Val Asp
1               5                  10                  15

Ser Ser Ala Thr Ser Ser Trp Ala Pro Pro Gly Ser Val Phe Pro Cys
            20                  25                  30

Pro Ser Cys Gly Pro Arg Gly Pro Asp Gln Arg Arg Pro Pro Pro Pro
        35                  40                  45

Pro Pro Pro Val Ser Pro Leu Pro Pro Ser Gln Pro Leu Pro Leu
    50                  55                  60

Pro Pro Leu Thr Pro Leu Lys Lys Asp His Asn Thr Asn Leu Trp
65                  70                  75                  80

Leu Pro Val Val Phe Phe Met Val Leu Ala Leu Val Gly Met Gly
                85                  90                  95

Leu Gly Met Tyr Gln Leu Phe His Leu Gln Lys Glu Leu Ala Glu Leu
            100                 105                 110

Arg Glu Phe Thr Asn Gln Ser Leu Lys Val Ser Ser Phe Glu Lys Gln
        115                 120                 125

Ile Ala Asn Pro Ser Thr Pro Ser Glu Lys Lys Glu Pro Arg Ser Val
130                 135                 140

Ala His Leu Thr Gly Asn Pro His Ser Arg Ser Ile Pro Leu Glu Trp
145                 150                 155                 160

Glu Asp Thr Tyr Gly Thr Ala Leu Ile Ser Gly Val Lys Tyr Lys Lys
                165                 170                 175

Gly Gly Leu Val Ile Asn Glu Thr Gly Leu Tyr Phe Val Tyr Ser Lys
            180                 185                 190

Val Tyr Phe Arg Gly Gln Ser Cys Asn Asn Gln Pro Leu Asn His Lys
        195                 200                 205

Val Tyr Met Arg Asn Ser Lys Tyr Pro Glu Asp Leu Val Leu Met Glu
    210                 215                 220

Glu Lys Arg Leu Asn Tyr Cys Thr Thr Gly Gln Ile Trp Ala His Ser
225                 230                 235                 240

Ser Tyr Leu Gly Ala Val Phe Asn Leu Thr Ser Ala Asp His Leu Tyr
                245                 250                 255

Val Asn Ile Ser Gln Leu Ser Leu Ile Asn Phe Glu Glu Ser Lys Thr
            260                 265                 270

Phe Phe Gly Leu Tyr Lys Leu
        275
```

<210> SEQ ID NO 10
<211> LENGTH: 278
<212> TYPE: PRT
<213> ORGANISM: Rattus norvegicus
<220> FEATURE:
<223> OTHER INFORMATION: rat Fas ligand (FasL), tumor necrosis factor
ligand superfamily member 6 (TNFSF6), apoptosis
antigen ligand (APTL, APT1LG1), CD178 antigen,
CD95L protein, death receptor ligand

<400> SEQUENCE: 10

```
Met Gln Gln Pro Val Asn Tyr Pro Cys Pro Gln Ile Tyr Trp Val Asp
1               5                  10                  15

Ser Ser Ala Thr Ser Pro Trp Ala Pro Pro Gly Ser Val Phe Ser Cys
            20                  25                  30

Pro Ser Ser Gly Pro Arg Gly Pro Gly Gln Arg Arg Pro Pro Pro Pro
```

```
                35                  40                  45
Pro Pro Pro Ser Pro Leu Pro Pro Ser Gln Pro Pro Leu
        50                  55                  60
Pro Pro Leu Ser Pro Leu Lys Lys Asp Asn Ile Glu Leu Trp Leu
65                  70                  75                  80
Pro Val Ile Phe Phe Met Val Leu Val Ala Leu Val Gly Met Gly Leu
                85                  90                  95
Gly Met Tyr Gln Leu Phe His Leu Gln Lys Glu Leu Ala Glu Leu Arg
            100                 105                 110
Glu Phe Thr Asn His Ser Leu Arg Val Ser Ser Phe Glu Lys Gln Ile
        115                 120                 125
Ala Asn Pro Ser Thr Pro Ser Glu Thr Lys Lys Pro Arg Ser Val Ala
    130                 135                 140
His Leu Thr Gly Asn Pro Arg Ser Arg Ser Ile Pro Leu Glu Trp Glu
145                 150                 155                 160
Asp Thr Tyr Gly Thr Ala Leu Ile Ser Gly Val Lys Tyr Lys Lys Gly
                165                 170                 175
Gly Leu Val Ile Asn Glu Ala Gly Leu Tyr Phe Val Tyr Ser Lys Val
            180                 185                 190
Tyr Phe Arg Gly Gln Ser Cys Asn Ser Gln Pro Leu Ser His Lys Val
        195                 200                 205
Tyr Met Arg Asn Phe Lys Tyr Pro Gly Asp Leu Val Leu Met Glu Glu
    210                 215                 220
Lys Lys Leu Asn Tyr Cys Thr Thr Gly Gln Ile Trp Ala His Ser Ser
225                 230                 235                 240
Tyr Leu Gly Ala Val Phe Asn Leu Thr Val Ala Asp His Leu Tyr Val
                245                 250                 255
Asn Ile Ser Gln Leu Ser Leu Ile Asn Phe Glu Glu Ser Lys Thr Phe
            260                 265                 270
Phe Gly Leu Tyr Lys Leu
            275

<210> SEQ ID NO 11
<211> LENGTH: 143
<212> TYPE: PRT
<213> ORGANISM: Artificial Sequence
<220> FEATURE:
<223> OTHER INFORMATION: Description of Artificial Sequence:human Fas
      ligand (FasL) sequence in VEGFR-FasL fusion
      protein

<400> S

Leu Thr Ser Ala Asp His Leu Tyr Val Asn Val Ser Glu Leu Ser Leu
        115                 120                 125

Val Asn Phe Glu Glu Ser Gln Thr Phe Phe Gly Leu Tyr Lys Leu
    130                 135                 140

<210> SEQ ID NO 12
<211> LENGTH: 143
<212> TYPE: PRT
<213> ORGANISM: Artificial Sequence
<220> FEATURE:
<223> OTHER INFORMATION: Description of Artificial Sequence:mouse Fas
      ligand (FasL) sequence in VEGFR-FasL fusion
      protein

<400> SEQUENCE: 12

Glu Lys Lys Glu Pro Arg Ser Val Ala His Leu Thr Gly Asn Pro His
  1               5                  10                  15

Ser Arg Ser Ile Pro Leu Glu Trp Glu Asp Thr Tyr Gly Thr Ala Leu
             20                  25                  30

Ile Ser Gly Val Lys Tyr Lys Lys Gly Gly Leu Val Ile Asn Glu Thr
         35                  40                  45

Gly Leu Tyr Phe Val Tyr Ser Lys Val Tyr Phe Arg Gly Gln Ser Cys
     50                  55                  60

Asn Asn Gln Pro Leu Asn His Lys Val Tyr Met Arg Asn Ser Lys Tyr
 65                  70                  75                  80

Pro Glu Asp Leu Val Leu Met Glu Glu Lys Arg Leu Asn Tyr Cys Thr
                 85                  90                  95

Thr Gly Gln Ile Trp Ala His Ser Ser Tyr Leu Gly Ala Val Phe Asn
            100                 105                 110

Leu Thr Ser Ala Asp His Leu Tyr Val Asn Ile Ser Gln Leu Ser Leu
        115                 120                 125

Ile Asn Phe Glu Glu Ser Lys Thr Phe Phe Gly Leu Tyr Lys Leu
    130                 135                 140

<210> SEQ ID NO 13
<211> LENGTH: 143
<212> TYPE: PRT
<213> ORGANISM: Artificial Sequence
<220> FEATURE:
<223> OTHER INFORMATION: Description of Artificial Sequence:rat Fas
      ligand (FasL) sequence in VEGFR-FasL fusion protein

<400> SEQUENCE: 13

Glu Thr Lys Lys Pro Arg Ser Val Ala His Leu Thr Gly Asn Pro Arg
  1               5                  10                  15

Ser Arg Ser Ile Pro Leu Glu Trp Glu Asp Thr Tyr Gly Thr Ala Leu
             20                  25                  30

Ile Ser Gly Val Lys Tyr Lys Lys Gly Gly Leu Val Ile Asn Glu Ala
         35                  40                  45

Gly Leu Tyr Phe Val Tyr Ser Lys Val Tyr Phe Arg Gly Gln Ser Cys
     50                  55                  60

Asn Ser Gln Pro Leu Ser His Lys Val Tyr Met Arg Asn Phe Lys Tyr
 65                  70                  75                  80

Pro Gly Asp Leu Val Leu Met Glu Glu Lys Lys Leu Asn Tyr Cys Thr
                 85                  90                  95

Thr Gly Gln Ile Trp Ala His Ser Ser Tyr Leu Gly Ala Val Phe Asn
            100                 105                 110

Leu Thr Val Ala Asp His Leu Tyr Val Asn Ile Ser Gln Leu Ser Leu

```
                    115                 120                 125
Ile Asn Phe Glu Glu Ser Lys Thr Phe Phe Gly Leu Tyr Lys Leu
                130                 135                 140

<210> SEQ ID NO 14
<211> LENGTH: 1455
<212> TYPE: DNA
<213> ORGANISM: Artificial Sequence
<220> FEATURE:
<223> OTHER INFORMATION: Description of Artificial Sequence:VEGFR-FasL
      fusion protein Flk(D1-D3)FasL(139-281), including
      signal peptide and linker sequence, FlkFasL cDNA

<400> SEQUENCE: 14
atggagagca aggcgctgct agctgtcgct ctgtggttct gcgtggagac ccgagccgcc        60
tctgtgggtt tgcctggcga ttttctccat cccccaagc tcagcacaca gaaagacata       120
ctgacaattt tggcaaatac aacccttcag attacttgca ggggacagcg ggacctggac       180 tggcttggc ccaatgctca gcgtgattct gaggaaaggg tattggtgac tgaatgcggc       240
ggtggtgaca gtatcttctg caaaacactc accattccca gggtggttgg aaatgatact       300
ggagcctaca gtgctcgta ccgggacgtc gacatagcct ccactgttta tgtctatgtt       360
cgagattaca gatcaccatt catcgcctct gtcagtgacc agcatggcat cgtgtacatc       420
accgagaaca gaacaaaac tgtggtgatc ccctgccgag ggtcgatttc aaacctcaat       480
gtgtctcttt gcgctaggta tccagaaaag agatttgttc cggatggaaa cagaatttcc       540
tgggacagcg ataggctt tactctcccc agttacatga tcagctatgc cggcatggtc       600
ttctgtgagg caaagatcaa tgatgaaacc tatcagtcta tcatgtacat agttgtggtt       660
gtaggatata ggatttatga tgtgattctg agccccccgc atgaaattga gctatctgcc       720
ggagaaaaac ttgtcttaaa ttgtacagcg agaacagagc tcaatgtggg gcttgatttc       780
acctggcact ctccaccttc aaagtctcat cataagaaga ttgtaaaccg ggatgtgaaa       840
ccctttcctg ggactgtggc gaagatgttt ttgagcacct tgacaataga agtgtgacc       900 aagagtgacc aagggaata cacctgtgta gcgtccagtg acgatgat caagagaaat       960 agaacatttg tccgagttca cacaaagcct tttattgctt tcggtagtgc tcagggact      1020 agtgaaaaaa aggagctgag gaaagtggcc catttaacag gcaagtccaa ctcaaggtcc      1080
atgcctctgg aatgggaaga cacctatgga attgtcctgc tttctggagt gaagtataag      1140
aagggtggcc ttgtgatcaa tgaaactggg ctgtactttg tatattccaa agtatacttc      1200
cggggtcaat cttgcaacaa cctgcccctg agccacaagg tctacatgag gaactctaag      1260
tatccccagg atctggtgat gatggagggg aagatgatga gctactgcac tactgggcag      1320
atgtgggccc gcagcagcta cctgggggca gtgttcaatc ttaccagtgc tgatcattta      1380
tatgtcaacg tatctgagct ctctctggtc aattttgagg aatctcagac gttttttcggc      1440 ttatataagc tctaa                                                      1455

<210> SEQ ID NO 15
<211> LENGTH: 951
<212> TYPE: DNA
<213> ORGANISM: Mus musculus
<220> FEATURE:
<223> OTHER INFORMATION: mouse vascular endothelial growth factor (VEGF,
      VPF, vasculotropin) receptor-2 (VEGFR-2), kinase domain receptor
      (KDR), fetal liver kinase 1 (Flk-1), type III receptor
      tyrosine kinase, kinase NYK extracellular domain (19-336) cDNA

<400> SEQUENCE: 15
```

```
gcctctgtgg gtttgcctgg cgattttctc catcccccca agctcagcac acagaaagac    60
atactgacaa ttttggcaaa tacaacccct cagattactt gcaggggaca gcggacctg    120 gactggcttt ggcccaatgc tcagcgtgat tctgaggaaa gggtattggt gactgaatgc    180
ggcggtggtg acagtatctt ctgcaaaaca ctcaccattc caggggtggt tggaaatgat    240
actggagcct acaagtgctc gtaccgggac gtcgacatag cctccactgt ttatgtctat    300
gttcgagatt acagatcacc attcatcgcc tctgtcagtg accagcatgg catcgtgtac    360
atcaccgaga acaagaacaa aactgtggtg atccctgcc gaggtcgat ttcaaacctc    420 aatgtgtctc tttgcgctag gtatccagaa aagagattg ttccggatgg aaacagaatt    480
tcctgggaca gcgagatagg ctttactctc cccagttaca tgatcagcta tgccggcatg    540
gtcttctgtg aggcaaagat caatgatgaa acctatcagt ctatcatgta catagttgtg    600
gttgtaggat ataggatta tgatgtgatt ctgagcccc cgcatgaaat tgagctatct    660
gccgagaaaa aacttgtctt aaattgtaca gcgagaacag agctcaatgt ggggcttgat    720
ttcacctggc actctccacc ttcaaagtct catcataaga agattgtaaa ccgggatgtg    780 aaacccttc ctgggactgt ggcgaagatg tttttgagca ccttgacaat agaaagtgtg    840
accaagagtg accaagggga atacacctgt gtagcgtcca gtggacggat gatcaagaga    900
aatagaacat ttgtccgagt tcacacaaag cctttattg ctttcggtag t    951
```

<210> SEQ ID NO 16
<211> LENGTH: 429
<212> TYPE: DNA
<213> ORGANISM: Homo sapiens
<220> FEATURE:
<223> OTHER INFORMATION: human Fas ligand (FasL) (139-281) cDNA

<400> SEQUENCE: 16

```
gaaaaaagg agctgaggaa agtggcccat ttaacaggca agtccaactc aaggtccatg     60
cctctggaat gggaagacac ctatggaatt gtcctgcttt ctggagtgaa gtataagaag    120
ggtggccttg tgatcaatga aactgggctg tactttgtat attccaaagt atacttccgg    180
ggtcaatctt gcaacaacct gccctgagc cacaaggtc acatgaggaa ctctaagtat    240
ccccaggatc tggtgatgat ggaggggaag atgatgagct actgcactac tgggcagatg    300
tgggcccgca gcagctacct gggggcagtg ttcaatctta ccagtgctga tcatttatat    360
gtcaacgtat ctgagctctc tctggtcaat tttgaggaat ctcagacgtt tttcggctta    420
tataagctc                                                           429
```

<210> SEQ ID NO 17
<211> LENGTH: 1002
<212> TYPE: DNA
<213> ORGANISM: Homo sapiens
<220> FEATURE:
<223> OTHER INFORMATION: human vascular endothelial growth factor (VEGF,
      VPF, vasculotropin) receptor-2 (VEGFR-2)
      extracellular domain (1-334) cDNA, including
      signal peptide

<400> SEQUENCE: 17

```
atgcagagca aggtgctgct ggccgtcgcc ctgtggctct gcgtggagac ccggccgcc     60 tctgtgggtt tgcctagtgt ttctcttgat ctgcccaggc tcagcataca aaaagacata    120
cttacaatta aggctaatac aactcttcaa attacttgca ggggacagag ggacttggac    180
tggctttggc ccaataatca gagtggcagt gagcaaaggg tggaggtgac tgagtgcagc    240
```

```
gatggcctct tctgtaagac actcacaatt ccaaaagtga tcggaaatga cactggagcc      300
tacaagtgct tctaccggga aactgacttg gcctcggtca tttatgtcta tgttcaagat      360
tacagatctc catttattgc ttctgttagt gaccaacatg gagtcgtgta cattactgag      420
aacaaaaaca aaactgtggt gattccatgt ctcgggtcca tttcaaatct caacgtgtca      480
ctttgtgcaa gatacccaga aaagagattt gttcctgatg gtaacagaat tcctgggac       540 agcaagaagg gctttactat tcccagctac atgatcagct atgctggcat ggtcttctgt      600
gaagcaaaaa ttaatgatga aagttaccag tctattatgt acatagttgt cgttgtaggg      660
tataggattt atgatgtggt tctgagtccg tctcatggaa ttgaactatc tgttggagaa      720
aagcttgtct taaattgtac agcaagaact gaactaaatg tggggattga cttcaactgg      780
gaataccctt cttcgaagca tcagcataag aaacttgtaa accgagacct aaaaacccag      840
tctgggagtg agatgaagaa attttttgagc accttaacta tagatggtgt aacccggagt     900
gaccaaggat tgtacacctg tgcagcatcc agtgggctga tgaccaagaa gaacagcaca      960
tttgtcaggg tccatgaaaa acctttttgtt gcttttggaa gt                       1002

<210> SEQ ID NO 18
<211> LENGTH: 945
<212> TYPE: DNA
<213> ORGANISM: Homo sapiens
<220> FEATURE:
<223> OTHER INFORMATION: human vascular endothelial growth factor (VEGF,
      VPF, vasculotropin) receptor-2 (VEGFR-2)
      extracellular domain (19-334) cDNA

<400> SEQUENCE: 18
gcctctgtgg gtttgcctag tgtttctctt gatctgccca ggctcagcat acaaaaagac       60
atacttacaa ttaaggctaa tacaactctt caaattactt gcaggggaca gagggacttg      120
gactggcttt ggcccaataa tcagagtggc agtgagcaaa gggtggaggt gactgagtgc      180
agcgatggcc tcttctgtaa gacactcaca attccaaaag tgatcggaaa tgacactgga      240
gcctacaagt gcttctaccg ggaaactgac ttggcctcgg tcatttatgt ctatgttcaa      300
gattacagat ctccatttat tgcttctgtt agtgaccaac atggagtcgt gtacattact      360
gagaacaaaa acaaaactgt ggtgattcca tgtctcgggt ccatttcaaa tctcaacgtg      420
tcactttgtg caagataccc agaaaagaga tttgttcctg atggtaacag aatttcctgg      480
gacagcaaga gagggcttta ctattcccag ctacatgatc agctatgctgg catggtcttc     540 tgtgaagcaa aaattaatga tgaaagttac cagtctatta tgtacatagt tgtcgttgta      600
gggtatagga tttatgatgt ggttctgagt ccgtctcatg gaattgaact atctgttgga      660
gaaaagcttg tcttaaattg tacagcaaga actgaactaa atgtggggat tgacttcaac      720
tgggaatacc cttcttcgaa gcatcagcat aagaaacttg taaaccgaga cctaaaaacc      780
cagtctggga gtgagatgaa gaaattttttg agcaccttaa ctatagatgg tgtaacccgg     840
agtgaccaag gattgtacac ctgtgcagca tccagtgggc tgatgaccaa gaagaacagc      900
acatttgtca gggtccatga aaaacctttt gttgcttttg gaagt                      945

<210> SEQ ID NO 19
<211> LENGTH: 1338
<212> TYPE: PRT
<213> ORGANISM: Homo sapiens
<220> FEATURE:
<223> OTHER INFORMATION: human vascular endothelial growth factor (VEGF,
      VPF, vasculotropin) receptor-1 (VEGFR-1), Fms-like tyrosine
``` kinase-1 (Flt-1), tyrosine-protein kinase FRT

<400> SEQUENCE: 19

```
Met Val Ser Tyr Trp Asp Thr Gly Val Leu Leu Cys Ala Leu Leu Ser
 1               5                  10                  15

Cys Leu Leu Thr Gly Ser Ser Ser Gly Ser Lys Leu Lys Asp Pro
             20                  25                  30

Glu Leu Ser Leu Lys Gly Thr Gln His Ile Met Gln Ala Gly Gln Thr
             35                  40                  45

Leu His Leu Gln Cys Arg Gly Glu Ala Ala His Lys Trp Ser Leu Pro
 50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
                100                 105                 110

Pro Thr Ser Lys Lys Lys Glu Thr Glu Ser Ala Ile Tyr Ile Phe Ile
             115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
275                 280                 285

Ala Asn Ile Phe Tyr Ser Val Leu Thr Ile Asp Lys Met Gln Asn Lys
            290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400
```

```
Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Phe Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
```

-continued

```
            820                 825                 830
Leu Gly Arg Gly Ala Phe Gly Lys Val Val Gln Ala Ser Ala Phe Gly
            835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
        930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
        995                1000                1005

Gly Met Glu Phe Leu Ser Ser Arg Lys Cys Ile His Arg Asp Leu Ala
    1010                1015                1020

Ala Arg Asn Ile Leu Leu Ser Glu Asn Asn Val Val Lys Ile Cys Asp
1025                1030                1035                1040

Phe Gly Leu Ala Arg Asp Ile Tyr Lys Asn Pro Asp Tyr Val Arg Lys
                1045                1050                1055

Gly Asp Thr Arg Leu Pro Leu Lys Trp Met Ala Pro Glu Ser Ile Phe
            1060                1065                1070

Asp Lys Ile Tyr Ser Thr Lys Ser Asp Val Trp Ser Tyr Gly Val Leu
        1075                1080                1085

Leu Trp Glu Ile Phe Ser Leu Gly Gly Ser Pro Tyr Pro Gly Val Gln
        1090                1095                1100

Met Asp Glu Asp Phe Cys Ser Arg Leu Arg Glu Gly Met Arg Met Arg
1105                1110                1115                1120

Ala Pro Glu Tyr Ser Thr Pro Glu Ile Tyr Gln Ile Met Leu Asp Cys
                1125                1130                1135

Trp His Arg Asp Pro Lys Glu Arg Pro Arg Phe Ala Glu Leu Val Glu
            1140                1145                1150

Lys Leu Gly Asp Leu Leu Gln Ala Asn Val Gln Gln Asp Gly Lys Asp
        1155                1160                1165

Tyr Ile Pro Ile Asn Ala Ile Leu Thr Gly Asn Ser Gly Phe Thr Tyr
        1170                1175                1180

Ser Thr Pro Ala Phe Ser Glu Asp Phe Phe Lys Glu Ser Ile Ser Ala
1185                1190                1195                1200

Pro Lys Phe Asn Ser Gly Ser Ser Asp Asp Val Arg Tyr Val Asn Ala
                1205                1210                1215

Phe Lys Phe Met Ser Leu Glu Arg Ile Lys Thr Phe Glu Glu Leu Leu
            1220                1225                1230

Pro Asn Ala Thr Ser Met Phe Asp Asp Tyr Gln Gly Asp Ser Ser Thr
        1235                1240                1245
```

```
Leu Leu Ala Ser Pro Met Leu Lys Arg Phe Thr Trp Thr Asp Ser Lys
    1250                1255                1260

Pro Lys Ala Ser Leu Lys Ile Asp Leu Arg Val Thr Ser Lys Ser Lys
1265                1270                1275                1280

Glu Ser Gly Leu Ser Asp Val Ser Arg Pro Ser Phe Cys His Ser Ser
                1285                1290                1295

Cys Gly His Val Ser Glu Gly Lys Arg Arg Phe Thr Tyr Asp His Ala
            1300                1305                1310

Glu Leu Glu Arg Lys Ile Ala Cys Cys Ser Pro Pro Pro Asp Tyr Asn
        1315                1320                1325

Ser Val Val Leu Tyr Ser Thr Pro Pro Ile
1330                1335
```

<210> SEQ ID NO 20
<211> LENGTH: 732
<212> TYPE: PRT
<213> ORGANISM: Homo sapiens
<220> FEATURE:
<223> OTHER INFORMATION: human vascular endothelial growth factor
      (VEGF, VPF, vasculotropin) receptor-1 (VEGFR-1), Fms-like tyrosine
      kinase-1 (Flt-1), tyrosine-protein kinase FRT
      extracellular domain (27-758)

<400> SEQUENCE: 20

```
Ser Lys Leu Lys Asp Pro Glu Leu Ser Leu Lys Gly Thr Gln His Ile
  1               5                  10                  15

Met Gln Ala Gly Gln Thr Leu His Leu Gln Cys Arg Gly Glu Ala Ala
             20                  25                  30

His Lys Trp Ser Leu Pro Glu Met Val Ser Lys Glu Ser Glu Arg Leu
         35                  40                  45

Ser Ile Thr Lys Ser Ala Cys Gly Arg Asn Gly Lys Gln Phe Cys Ser
     50                  55                  60

Thr Leu Thr Leu Asn Thr Ala Gln Ala Asn His Thr Gly Phe Tyr Ser
 65                  70                  75                  80

Cys Lys Tyr Leu Ala Val Pro Thr Ser Lys Lys Lys Glu Thr Glu Ser
                 85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
    130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Gln Ile
        195                 200                 205

Ser Thr Pro Arg Pro Val Lys Leu Leu Arg Gly His Thr Leu Val Leu
    210                 215                 220

Asn Cys Thr Ala Thr Thr Pro Leu Asn Thr Arg Val Gln Met Thr Trp
225                 230                 235                 240

Ser Tyr Pro Asp Glu Lys Asn Lys Arg Ala Ser Val Arg Arg Arg Ile
                245                 250                 255
```

```
Asp Gln Ser Asn Ser His Ala Asn Ile Phe Tyr Ser Val Leu Thr Ile
            260                 265                 270
Asp Lys Met Gln Asn Lys Asp Lys Gly Leu Tyr Thr Cys Arg Val Arg
275                 280                 285
Ser Gly Pro Ser Phe Lys Ser Val Asn Thr Ser Val His Ile Tyr Asp
    290                 295                 300
Lys Ala Phe Ile Thr Val Lys His Arg Lys Gln Gln Val Leu Glu Thr
305                 310                 315                 320
Val Ala Gly Lys Arg Ser Tyr Arg Leu Ser Met Lys Val Lys Ala Phe
                325                 330                 335
Pro Ser Pro Glu Val Val Trp Leu Lys Asp Gly Leu Pro Ala Thr Glu
            340                 345                 350
Lys Ser Ala Arg Tyr Leu Thr Arg Gly Tyr Ser Leu Ile Ile Lys Asp
                355                 360                 365
Val Thr Glu Glu Asp Ala Gly Asn Tyr Thr Ile Leu Leu Ser Ile Lys
370                 375                 380
Gln Ser Asn Val Phe Lys Asn Leu Thr Ala Thr Leu Ile Val Asn Val
385                 390                 395                 400
Lys Pro Gln Ile Tyr Glu Lys Ala Val Ser Ser Phe Pro Asp Pro Ala
                405                 410                 415
Leu Tyr Pro Leu Gly Ser Arg Gln Ile Leu Thr Cys Thr Ala Tyr Gly
            420                 425                 430
Ile Pro Gln Pro Thr Ile Lys Trp Phe Trp His Pro Cys Asn His Asn
            435                 440                 445
His Ser Glu Ala Arg Cys Asp Phe Cys Ser Asn Asn Glu Glu Ser Phe
    450                 455                 460
Ile Leu Asp Ala Asp Ser Asn Met Gly Asn Arg Ile Glu Ser Ile Thr
465                 470                 475                 480
Gln Arg Met Ala Ile Ile Glu Gly Lys Asn Lys Met Ala Ser Thr Leu
                485                 490                 495
Val Val Ala Asp Ser Arg Ile Ser Gly Ile Tyr Ile Cys Ile Ala Ser
            500                 505                 510
Asn Lys Val Gly Thr Val Gly Arg Asn Ile Ser Phe Tyr Ile Thr Asp
            515                 520                 525
Val Pro Asn Gly Phe His Val Asn Leu Glu Lys Met Pro Thr Glu Gly
    530                 535                 540
Glu Asp Leu Lys Leu Ser Cys Thr Val Asn Lys Phe Leu Tyr Arg Asp
545                 550                 555                 560
Val Thr Trp Ile Leu Leu Arg Thr Val Asn Asn Arg Thr Met His Tyr
                565                 570                 575
Ser Ile Ser Lys Gln Lys Met Ala Ile Thr Lys Glu His Ser Ile Thr
            580                 585                 590
Leu Asn Leu Thr Ile Met Asn Val Ser Leu Gln Asp Ser Gly Thr Tyr
            595                 600                 605
Ala Cys Arg Ala Arg Asn Val Tyr Thr Gly Glu Glu Ile Leu Gln Lys
    610                 615                 620
Lys Glu Ile Thr Ile Arg Asp Gln Glu Ala Pro Tyr Leu Leu Arg Asn
625                 630                 635                 640
Leu Ser Asp His Thr Val Ala Ile Ser Ser Ser Thr Thr Leu Asp Cys
                645                 650                 655
His Ala Asn Gly Val Pro Glu Pro Gln Ile Thr Trp Phe Lys Asn Asn
            660                 665                 670
```

```
                His Lys Ile Gln Gln Glu Pro Gly Ile Ile Leu Gly Pro Gly Ser Ser
                675                 680                 685

Thr Leu Phe Ile Glu Arg Val Thr Glu Asp Glu Gly Val Tyr His
                690                 695                 700

Cys Lys Ala Thr Asn Gln Lys Gly Ser Val Glu Ser Ser Ala Tyr Leu
                705                 710                 715                 720

Thr Val Gln Gly Thr Ser Asp Lys Ser Asn Leu Glu
                                725                 730

<210> SEQ ID NO 21
<211> LENGTH: 2196
<212> TYPE: DNA
<213> ORGANISM: Homo sapiens
<220> FEATURE:
<223> OTHER INFORMATION: human vascular endothelial growth factor (VEGF,
      VPF, vasculotropin) receptor-1 (VEGFR-1), Fms-like tyrosine
      kinase-1 (Flt-1), tyrosine-protein kinase FRT
      extracellular domain (27-758) cDNA

<400> SEQUENCE: 21
tcaaaattaa aagatcctga actgagttta aaaggcaccc agcacatcat gcaagcaggc      60
cagacactgc atctccaatg cagggggaa gcagcccata atggtctttt gcctgaaatg      120
gtgagtaagg aaagcgaaag gctgagcata actaaatctg cctgtggaag aaatggcaaa    180
caattctgca gtactttaac cttgaacaca gctcaagcaa accacactgg cttctacagc    240
tgcaaatatc tagctgtacc tacttcaaag aagaaggaaa cagaatctgc aatctatata    300
tttattagtg atacaggtag acctttcgta gagatgtaca gtgaaatccc cgaaattata    360
cacatgactg aaggaaggga gctcgtcatt ccctgccggg ttacgtcacc taacatcact    420
gttactttaa aaagtttcc acttgacact ttgatccctg atggaaaacg cataatctgg    480
gacagtagaa agggcttcat catatcaaat gcaacgtaca agaaatagg gcttctgacc    540 tgtgaagcaa cagtcaatgg gcatttgtat aagacaaact atctcacaca tcgacaaacc    600
aatacaatca tagatgtcca ataagcaca ccacgcccag tcaaattact tagaggccat    660
actcttgtcc tcaattgtac tgctaccact cccttgaaca cgagagttca atgacctgg    720 agttaccctg atgaaaaaaa taagagagct tccgtaaggc gacgaattga ccaaagcaat    780
tcccatgcca acatattcta cagtgttctt actattgaca aaatgcagaa caaagacaaa    840
ggactttata cttgtcgtgt aaggagtgga ccatcattca aatctgttaa cacctcagtg    900
catatatatg ataaagcatt catcactgtg aaacatcgaa acagcaggt gcttgaaacc    960 gtagctggca agcggtctta ccggctctct atgaaagtga aggcatttcc ctcgccggaa  1020
gttgtatggt taaagatgg gttacctgcg actgagaaat ctgctcgcta tttgactcgt   1080
ggctactcgt taattatcaa ggacgtaact gaagaggatg cagggaatta tacaatcttg    1140
ctgagcataa acagtcaaa tgtgtttaaa acctcactg ccactctaat tgtcaatgtg     1200 aaacccccaga tttacgaaaa ggccgtgtca tcgtttccag acccggctct tacccactg    1260 ggcagcagac aaatcctgac ttgtaccgca tatggtatcc ctcaacctac aatcaagtgg    1320
ttctggcacc cctgtaacca taatcattcc gaagcaaggt gtgactttg ttccaataat     1380 gaagagtcct ttatcctgga tgctgacagc aacatgggaa acagaattga gagcatcact    1440
cagcgcatgg caataataga aggaaagaat aagatggcta gcaccttggt tgtggctgac    1500
tctagaattt ctggaatcta catttgcata gcttccaata agttgggac tgtgggaaga    1560 aacataagct tttatatcac agatgtgcca atgggttttc atgttaactt ggaaaaaatg    1620
```

-continued

```
ccgacggaag gagaggacct gaaactgtct tgcacagtta acaagttctt atacagagac    1680
gttacttgga ttttactgcg gacagttaat aacagaacaa tgcactacag tattagcaag    1740
caaaaaatgg ccatcactaa ggagcactcc atcactctta atcttaccat catgaatgtt    1800
tccctgcaag attcaggcac ctatgcctgc agagccagga atgtatacac aggggaagaa    1860
atcctccaga agaaagaaat tacaatcaga gatcaggaag caccatacct cctgcgaaac    1920
ctcagtgatc acacagtggc catcagcagt tccaccactt tagactgtca tgctaatggt    1980
gtccccgagc tcagatcac ttggtttaaa aacaaccaca aaatacaaca agagcctgga    2040
attattttag gaccaggaag cagcacgctg tttattgaaa gagtcacaga agaggatgaa    2100
ggtgtctatc actgcaaagc caccaaccag aagggctctg tggaaagttc agcataccte    2160 actgttcaag gaacctcgga caagtctaat ctggag                              2196
```

<210> SEQ ID NO 22
<211> LENGTH: 484
<212> TYPE: PRT
<213> ORGANISM: Artificial Sequence
<220> FEATURE:
<223> OTHER INFORMATION: Description of Artificial Sequence:Flk(D1-D3)
      +FasL(139-281) fusion protein, including signal peptide, FlkFasL

<400> SEQUENCE: 22

```
Met Glu Ser Lys Ala Leu Leu Ala Val Ala Leu Trp Phe Cys Val Glu
  1               5                  10                  15

Thr Arg Ala Ala Ser Val Gly Leu Pro Gly Asp Phe Leu His Pro Pro
             20                  25                  30

Lys Leu Ser Thr Gln Lys Asp Ile Leu Thr Ile Leu Ala Asn Thr Thr
         35                  40                  45

Leu Gln Ile Thr Cys Arg Gly Gln Arg Asp Leu Asp Trp Leu Trp Pro
     50                  55                  60

Asn Ala Gln Arg Asp Ser Glu Glu Arg Val Leu Val Thr Glu Cys Gly
 65                  70                  75                  80

Gly Gly Asp Ser Ile Phe Cys Lys Thr Leu Thr Ile Pro Arg Val Val
                 85                  90                  95

Gly Asn Asp Thr Gly Ala Tyr Lys Cys Ser Tyr Arg Asp Val Asp Ile
            100                 105                 110

Ala Ser Thr Val Tyr Val Tyr Val Arg Asp Tyr Arg Ser Pro Phe Ile
        115                 120                 125

Ala Ser Val Ser Asp Gln His Gly Ile Val Tyr Ile Thr Glu Asn Lys
    130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
                165                 170                 175

Asn Arg Ile Ser Trp Asp Ser Glu Ile Gly Phe Thr Leu Pro Ser Tyr
            180                 185                 190

Met Ile Ser Tyr Ala Gly Met Val Phe Cys Glu Ala Lys Ile Asn Asp
        195                 200                 205

Glu Thr Tyr Gln Ser Ile Met Tyr Ile Val Val Val Gly Tyr Arg
    210                 215                 220

Ile Tyr Asp Val Ile Leu Ser Pro Pro His Glu Ile Glu Leu Ser Ala
225                 230                 235                 240

Gly Glu Lys Leu Val Leu Asn Cys Thr Ala Arg Thr Glu Leu Asn Val
                245                 250                 255
```

```
Gly Leu Asp Phe Thr Trp His Ser Pro Ser Lys Ser His His Lys
            260                 265                 270

Lys Ile Val Asn Arg Asp Val Lys Pro Phe Pro Gly Thr Val Ala Lys
        275                 280                 285

Met Phe Leu Ser Thr Leu Thr Ile Glu Ser Val Thr Lys Ser Asp Gln
    290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
                325                 330                 335

Ala Arg Gly Thr Ser Glu Lys Lys Glu Leu Arg Lys Val Ala His Leu
            340                 345                 350

Thr Gly Lys Ser Asn Ser Arg Ser Met Pro Leu Glu Trp Glu Asp Thr
        355                 360                 365

Tyr Gly Ile Val Leu Leu Ser Gly Val Lys Tyr Lys Lys Gly Gly Leu
    370                 375                 380

Val Ile Asn Glu Thr Gly Leu Tyr Phe Val Tyr Ser Lys Val Tyr Phe
385                 390                 395                 400

Arg Gly Gln Ser Cys Asn Asn Leu Pro Leu Ser His Lys Val Tyr Met
                405                 410                 415

Arg Asn Ser Lys Tyr Pro Gln Asp Leu Val Met Met Glu Gly Lys Met
            420                 425                 430

Met Ser Tyr Cys Thr Thr Gly Gln Met Trp Ala Arg Ser Ser Tyr Leu
        435                 440                 445

Gly Ala Val Phe Asn Leu Thr Ser Ala Asp His Leu Tyr Val Asn Val
    450                 455                 460

Ser Glu Leu Ser Leu Val Asn Phe Glu Glu Ser Gln Thr Phe Phe Gly
465                 470                 475                 480

Leu Tyr Lys Leu

<210> SEQ ID NO 23
<211> LENGTH: 465
<212> TYPE: PRT
<213> ORGANISM: Artificial Sequence
<220> FEATURE:
<223> OTHER INFORMATION: Description of Artificial Sequence:Flk(D1-D3)
      +FasL(139-281) fusion protein, without signal peptide

<400> SEQUENCE: 23

Ala Ser Val Gly Leu Pro Gly Asp Phe Leu His Pro Lys Leu Ser
  1               5                  10                  15

Thr Gln Lys Asp Ile Leu Thr Ile Leu Ala Asn Thr Thr Leu Gln Ile
                20                  25                  30

Thr Cys Arg Gly Gln Arg Asp Leu Asp Trp Leu Trp Pro Asn Ala Gln
            35                  40                  45

Arg Asp Ser Glu Glu Arg Val Leu Val Thr Glu Cys Gly Gly Gly Asp
    50                  55                  60

Ser Ile Phe Cys Lys Thr Leu Thr Ile Pro Arg Val Val Gly Asn Asp
65                  70                  75                  80

Thr Gly Ala Tyr Lys Cys Ser Tyr Arg Asp Val Asp Ile Ala Ser Thr
                85                  90                  95

Val Tyr Val Tyr Val Arg Asp Tyr Arg Ser Pro Phe Ile Ala Ser Val
            100                 105                 110

Ser Asp Gln His Gly Ile Val Tyr Ile Thr Glu Asn Lys Asn Lys Thr
    115                 120                 125
```

```
Val Val Ile Pro Cys Arg Gly Ser Ile Ser Asn Leu Asn Val Ser Leu
    130                 135                 140
Cys Ala Arg Tyr Pro Glu Lys Arg Phe Val Pro Asp Gly Asn Arg Ile
145                 150                 155                 160
Ser Trp Asp Ser Glu Ile Gly Phe Thr Leu Pro Ser Tyr Met Ile Ser
                165                 170                 175
Tyr Ala Gly Met Val Phe Cys Glu Ala Lys Ile Asn Asp Glu Thr Tyr
            180                 185                 190
Gln Ser Ile Met Tyr Ile Val Val Val Gly Tyr Arg Ile Tyr Asp
        195                 200                 205
Val Ile Leu Ser Pro Pro His Glu Ile Glu Leu Ser Ala Gly Glu Lys
    210                 215                 220
Leu Val Leu Asn Cys Thr Ala Arg Thr Glu Leu Asn Val Gly Leu Asp
225                 230                 235                 240
Phe Thr Trp His Ser Pro Ser Lys Ser His His Lys Lys Ile Val
                245                 250                 255
Asn Arg Asp Val Lys Pro Phe Pro Gly Thr Val Ala Lys Met Phe Leu
            260                 265                 270
Ser Thr Leu Thr Ile Glu Ser Val Thr Lys Ser Asp Gln Gly Glu Tyr
        275                 280                 285
Thr Cys Val Ala Ser Ser Gly Arg Met Ile Lys Arg Asn Arg Thr Phe
    290                 295                 300
Val Arg Val His Thr Lys Pro Phe Ile Ala Phe Gly Ser Ala Arg Gly
305                 310                 315                 320
Thr Ser Glu Lys Lys Glu Leu Arg Lys Val Ala His Leu Thr Gly Lys
                325                 330                 335
Ser Asn Ser Arg Ser Met Pro Leu Glu Trp Glu Asp Thr Tyr Gly Ile
            340                 345                 350
Val Leu Leu Ser Gly Val Lys Tyr Lys Lys Gly Gly Leu Val Ile Asn
        355                 360                 365
Glu Thr Gly Leu Tyr Phe Val Tyr Ser Lys Val Tyr Phe Arg Gly Gln
    370                 375                 380
Ser Cys Asn Asn Leu Pro Leu Ser His Lys Val Tyr Met Arg Asn Ser
385                 390                 395                 400
Lys Tyr Pro Gln Asp Leu Val Met Met Glu Gly Lys Met Met Ser Tyr
                405                 410                 415
Cys Thr Thr Gly Gln Met Trp Ala Arg Ser Ser Tyr Leu Gly Ala Val
            420                 425                 430
Phe Asn Leu Thr Ser Ala Asp His Leu Tyr Val Asn Val Ser Glu Leu
        435                 440                 445
Ser Leu Val Asn Phe Glu Glu Ser Gln Thr Phe Phe Gly Leu Tyr Lys
    450                 455                 460
Leu
465

<210> SEQ ID NO 24
<211> LENGTH: 840
<212> TYPE: PRT
<213> ORGANISM: Homo sapiens
<220> FEATURE:
<223> OTHER INFORMATION: human neuropilin-1 (NRP-1), vascular
      endothelial cell growth factor 165 receptor, including signal
      peptide extracellular domain, including signal peptide

<400> SEQUENCE: 24

Met Glu Arg Gly Leu Pro Leu Leu Cys Ala Val Leu Ala Leu Val Leu
```

```
  1               5                  10                 15
Ala Pro Ala Gly Ala Phe Arg Asn Asp Lys Cys Gly Asp Thr Ile Lys
                 20                 25                 30

Ile Glu Ser Pro Gly Tyr Leu Thr Ser Pro Gly Tyr Pro His Ser Tyr
                 35                 40                 45

His Pro Ser Glu Lys Cys Glu Trp Leu Ile Gln Ala Pro Asp Pro Tyr
                 50                 55                 60

Gln Arg Ile Met Ile Asn Phe Asn Pro His Phe Asp Leu Glu Asp Arg
 65                 70                 75                 80

Asp Cys Lys Tyr Asp Tyr Val Glu Val Phe Asp Gly Glu Asn Glu Asn
                 85                 90                 95

Gly His Phe Arg Gly Lys Phe Cys Gly Lys Ile Ala Pro Pro Pro Val
                 100                105                110

Val Ser Ser Gly Pro Phe Leu Phe Ile Lys Phe Val Ser Asp Tyr Glu
                 115                120                125

Thr His Gly Ala Gly Phe Ser Ile Arg Tyr Glu Ile Phe Lys Arg Gly
                 130                135                140

Pro Glu Cys Ser Gln Asn Tyr Thr Thr Pro Ser Gly Val Ile Lys Ser
145                150                155                160

Pro Gly Phe Pro Glu Lys Tyr Pro Asn Ser Leu Glu Cys Thr Tyr Ile
                 165                170                175

Val Phe Ala Pro Lys Met Ser Glu Ile Ile Leu Glu Phe Glu Ser Phe
                 180                185                190

Asp Leu Glu Pro Asp Ser Asn Pro Pro Gly Gly Met Phe Cys Arg Tyr
                 195                200                205

Asp Arg Leu Glu Ile Trp Asp Gly Phe Pro Asp Val Gly Pro His Ile
                 210                215                220

Gly Arg Tyr Cys Gly Gln Lys Thr Pro Gly Arg Ile Arg Ser Ser Ser
225                230                235                240

Gly Ile Leu Ser Met Val Phe Tyr Thr Asp Ser Ala Ile Ala Lys Glu
                 245                250                255

Gly Phe Ser Ala Asn Tyr Ser Val Leu Gln Ser Ser Val Ser Glu Asp
                 260                265                270

Phe Lys Cys Met Glu Ala Leu Gly Met Glu Ser Gly Glu Ile His Ser
                 275                280                285

Asp Gln Ile Thr Ala Ser Ser Gln Tyr Ser Thr Asn Trp Ser Ala Glu
                 290                295                300

Arg Ser Arg Leu Asn Tyr Pro Glu Asn Gly Trp Thr Pro Gly Glu Asp
305                310                315                320

Ser Tyr Arg Glu Trp Ile Gln Val Asp Leu Gly Leu Leu Arg Phe Val
                 325                330                335

Thr Ala Val Gly Thr Gln Gly Ala Ile Ser Lys Glu Thr Lys Lys Lys
                 340                345                350

Tyr Tyr Val Lys Thr Tyr Lys Ile Asp Val Ser Ser Asn Gly Glu Asp
                 355                360                365

Trp Ile Thr Ile Lys Glu Gly Asn Lys Pro Val Leu Phe Gln Gly Asn
                 370                375                380

Thr Asn Pro Thr Asp Val Val Ala Val Phe Pro Lys Pro Leu Ile
385                390                395                400

Thr Arg Phe Val Arg Ile Lys Pro Ala Thr Trp Glu Thr Gly Ile Ser
                 405                410                415

Met Arg Phe Glu Val Tyr Gly Cys Lys Ile Thr Asp Tyr Pro Cys Ser
                 420                425                430
```

```
Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
                500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
        530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
        595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
        690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr His Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
        770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp
            835                 840
```

<210> SEQ ID NO 25
<211> LENGTH: 1362
<212> TYPE: PRT
<213> ORGANISM: Homo sapiens
<220> FEATURE:
<223> OTHER INFORMATION: human vascular endothelial growth factor
      (VEGF, VPF, vasculotropin) receptor-3 (VEGFR-3), Fms-related
      tyrosine kinase 4 isoform 1

<400> SEQUENCE: 25

Met Gln Arg Gly Ala Ala Leu Cys Leu Arg Leu Trp Leu Cys Leu Gly
 1               5                  10                  15

Leu Leu Asp Gly Leu Val Ser Asp Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
    290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Pro Glu Phe Gln Trp

```
                355                 360                 365
Tyr Lys Asp Gly Lys Ala Leu Ser Gly Arg His Ser Pro His Ala Leu
370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
                405                 410                 415

Val Val Asn Val Pro Pro Gln Ile His Glu Lys Glu Ala Ser Ser Pro
                420                 425                 430

Ser Ile Tyr Ser Arg His Ser Arg Gln Ala Leu Thr Cys Thr Ala Tyr
                435                 440                 445

Gly Val Pro Leu Pro Leu Ser Ile Gln Trp His Trp Arg Pro Trp Thr
                450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
                485                 490                 495

Ala Val Asn Pro Ile Glu Ser Leu Asp Thr Trp Thr Glu Phe Val Glu
                500                 505                 510

Gly Lys Asn Lys Thr Val Ser Lys Leu Val Ile Gln Asn Ala Asn Val
                515                 520                 525

Ser Ala Met Tyr Lys Cys Val Val Ser Asn Lys Val Gly Gln Asp Glu
530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
                565                 570                 575

Ser Cys Gln Ala Asp Ser Tyr Lys Tyr Glu His Leu Arg Trp Tyr Arg
                580                 585                 590

Leu Asn Leu Ser Thr Leu His Asp Ala His Gly Asn Pro Leu Leu Leu
                595                 600                 605

Asp Cys Lys Asn Val His Leu Phe Ala Thr Pro Leu Ala Ala Ser Leu
                610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
                660                 665                 670

Gln Ala Leu Glu Ala Pro Arg Leu Thr Gln Asn Leu Thr Asp Leu Leu
                675                 680                 685

Val Asn Val Ser Asp Ser Leu Glu Met Gln Cys Leu Val Ala Gly Ala
                690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                725                 730                 735

Arg Val Arg Glu Glu Asp Ala Gly Pro Tyr Leu Cys Ser Val Cys Arg
                740                 745                 750

Pro Lys Gly Cys Val Asn Ser Ser Ala Ser Val Ala Val Glu Gly Ser
                755                 760                 765

Glu Asp Lys Gly Ser Met Glu Ile Val Ile Leu Val Gly Thr Gly Val
770                 775                 780
```

```
Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Glu Gln Cys Gly Tyr Leu Ser
            820                 825                 830

Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Val Glu Ala Ser Ala
            850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu Gln Arg Ala Leu Met Ser Glu
            885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
            965                 970                 975

Ser Asp Arg Val Leu Phe Ala Arg Phe Ser Lys Thr Glu Gly Gly Ala
            980                 985                 990

Arg Arg Ala Ser Pro Asp Gln Glu Ala Glu Asp Leu Trp Leu Ser Pro
            995                 1000                1005

Leu Thr Met Glu Asp Leu Val Cys Tyr Ser Phe Gln Val Ala Arg Gly
    1010                1015                1020

Met Glu Phe Leu Ala Ser Arg Lys Cys Ile His Arg Asp Leu Ala Ala
1025                1030                1035                1040

Arg Asn Ile Leu Leu Ser Glu Ser Asp Val Val Lys Ile Cys Asp Phe
                1045                1050                1055

Gly Leu Ala Arg Asp Ile Tyr Lys Asp Pro Asp Tyr Val Arg Lys Gly
                1060                1065                1070

Ser Ala Arg Leu Pro Leu Lys Trp Met Ala Pro Glu Ser Ile Phe Asp
                1075                1080                1085

Lys Val Tyr Thr Thr Gln Ser Asp Val Trp Ser Phe Gly Val Leu Leu
                1090                1095                1100

Trp Glu Ile Phe Ser Leu Gly Ala Ser Pro Tyr Pro Gly Val Gln Ile
1105                1110                1115                1120

Asn Glu Glu Phe Cys Gln Arg Val Arg Asp Gly Thr Arg Met Arg Ala
                1125                1130                1135

Pro Glu Leu Ala Thr Pro Ala Ile Arg His Ile Met Leu Asn Cys Trp
                1140                1145                1150

Ser Gly Asp Pro Lys Ala Arg Pro Ala Phe Ser Glu Leu Val Glu Ile
                1155                1160                1165

Leu Gly Asp Leu Leu Gln Gly Arg Gly Leu Gln Glu Glu Glu Glu Val
                1170                1175                1180

Cys Met Ala Pro Arg Ser Ser Gln Ser Ser Glu Glu Gly Ser Phe Ser
1185                1190                1195                1200
```

-continued

```
Gln Val Ser Thr Met Ala Leu His Ile Ala Gln Asp Ala Glu Asp
                1205                1210                1215

Ser Pro Pro Ser Leu Gln Arg His Ser Leu Ala Ala Arg Tyr Tyr Asn
        1220                1225                1230

Trp Val Ser Phe Pro Gly Cys Leu Ala Arg Gly Ala Glu Thr Arg Gly
        1235                1240                1245

Ser Ser Arg Met Lys Thr Phe Glu Glu Phe Pro Met Thr Pro Thr Thr
    1250                1255                1260

Tyr Lys Gly Ser Val Asp Asn Gln Thr Asp Ser Gly Met Val Leu Ala
1265                1270                1275                1280

Ser Glu Glu Phe Glu Gln Ile Glu Ser Arg His Arg Gln Glu Ser Gly
                1285                1290                1295

Phe Ser Cys Lys Gly Pro Gly Gln Asn Val Ala Val Thr Arg Ala His
                1300                1305                1310

Pro Asp Ser Gln Gly Arg Arg Arg Arg Pro Glu Arg Gly Ala Arg Gly
                1315                1320                1325

Gly Gln Val Phe Tyr Asn Ser Glu Tyr Gly Glu Leu Ser Glu Pro Ser
            1330                1335                1340

Glu Glu Asp His Cys Ser Pro Ser Ala Arg Val Thr Phe Phe Thr Asp
1345                1350                1355                1360

Asn Ser
```

<210> SEQ ID NO 26
<211> LENGTH: 819
<212> TYPE: PRT
<213> ORGANISM: Homo sapiens
<220> FEATURE:
<223> OTHER INFORMATION: human vascular endothelial growth factor (VEGF, VPF, vasculotropin) receptor-2 (VEGFR-2), kinase domain receptor (KDR), fetal liver kinase 1 (Flk-1), type III receptor tyrosine kinase, kinase NYK extracellular and transmembrane domains

<400> SEQUENCE: 26

```
Met Gln Ser Lys Val Leu Leu Ala Val Ala Leu Trp Leu Cys Val Glu
  1               5                  10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
 65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
```

```
              180                 185                 190
Ser Tyr Ala Gly Met Val Phe Cys Glu Ala Lys Ile Asn Asp Glu Ser
            195                 200                 205

Tyr Gln Ser Ile Met Tyr Ile Val Val Val Gly Tyr Arg Ile Tyr
        210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605
```

-continued

```
Leu Trp Lys Leu Asn Ala Thr Met Phe Ser Asn Ser Thr Asn Asp Ile
        610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
                675                 680                 685

Thr Ala Ser Gly Asn Pro Pro Pro Gln Ile Met Trp Phe Lys Asp Asn
690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
                740                 745                 750

Ile Ile Glu Gly Ala Gln Glu Lys Thr Asn Leu Glu Ile Ile Ile Leu
                755                 760                 765

Val Gly Thr Ala Val Ile Ala Met Phe Phe Trp Leu Leu Leu Val Ile
770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg

<210> SEQ ID NO 27
<211> LENGTH: 817
<212> TYPE: PRT
<213> ORGANISM: Mus musculus
<220> FEATURE:
<223> OTHER INFORMATION: mouse vascular endothelial growth factor (VEGF,
      VPF, vasculotropin) receptor-2 (VEGFR-2), kinase domain receptor
      (KDR), fetal liver kinase 1 (Flk-1), type III receptor tyrosine
      kinase, kinase NYK extracellular and transmembrane domains

<400> SEQUENCE: 27

Met Glu Ser Lys Ala Leu Leu Ala Val Ala Leu Trp Phe Cys Val Glu
1               5                   10                  15

Thr Arg Ala Ala Ser Val Gly Leu Pro Gly Asp Phe Leu His Pro Pro
                20                  25                  30

Lys Leu Ser Thr Gln Lys Asp Ile Leu Thr Ile Leu Ala Asn Thr Thr
            35                  40                  45

Leu Gln Ile Thr Cys Arg Gly Gln Arg Asp Leu Asp Trp Leu Trp Pro
        50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val
                85                  90                  95

Gly Asn Asp Thr Gly Ala Tyr Lys Cys Ser Tyr Arg Asp Val Asp Ile
                100                 105                 110

Ala Ser Thr Val Tyr Val Tyr Val Arg Asp Tyr Arg Ser Pro Phe Ile
            115                 120                 125
```

```
Ala Ser Val Ser Asp Gln His Gly Ile Val Tyr Ile Thr Glu Asn Lys
130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
                165                 170                 175

Asn Arg Ile Ser Trp Asp Ser Glu Ile Gly Phe Thr Leu Pro Ser Tyr
                180                 185                 190

Met Ile Ser Tyr Ala Gly Met Val Phe Cys Glu Ala Lys Ile Asn Asp
                195                 200                 205

Glu Thr Tyr Gln Ser Ile Met Tyr Ile Val Val Val Gly Tyr Arg
210                 215                 220

Ile Tyr Asp Val Ile Leu Ser Pro Pro His Glu Ile Glu Leu Ser Ala
225                 230                 235                 240

Gly Glu Lys Leu Val Leu Asn Cys Thr Ala Arg Thr Glu Leu Asn Val
                245                 250                 255

Gly Leu Asp Phe Thr Trp His Ser Pro Pro Ser Lys Ser His His Lys
                260                 265                 270

Lys Ile Val Asn Arg Asp Val Lys Pro Phe Pro Gly Thr Val Ala Lys
                275                 280                 285

Met Phe Leu Ser Thr Leu Thr Ile Glu Ser Val Thr Lys Ser Asp Gln
290                 295                 300

Gly Glu Tyr Thr Cys Val Ala Ser Ser Gly Arg Met Ile Lys Arg Asn
305                 310                 315                 320

Arg Thr Phe Val Arg Val His Thr Lys Pro Phe Ile Ala Phe Gly Ser
                325                 330                 335

Gly Met Lys Ser Leu Val Glu Ala Thr Val Gly Ser Gln Val Arg Ile
                340                 345                 350

Pro Val Lys Tyr Leu Ser Tyr Pro Ala Pro Asp Ile Lys Trp Tyr Arg
                355                 360                 365

Asn Gly Arg Pro Ile Glu Ser Asn Tyr Thr Met Ile Val Gly Asp Glu
370                 375                 380

Leu Thr Ile Met Glu Val Thr Glu Arg Asp Ala Gly Asn Tyr Thr Val
385                 390                 395                 400

Ile Leu Thr Asn Pro Ile Ser Met Glu Lys Gln Ser His Met Val Ser
                405                 410                 415

Leu Val Val Asn Val Pro Pro Gln Ile Gly Glu Lys Ala Leu Ile Ser
                420                 425                 430

Pro Met Asp Ser Tyr Gln Tyr Gly Thr Met Gln Thr Leu Thr Cys Thr
                435                 440                 445

Val Tyr Ala Asn Pro Pro Leu His His Ile Gln Trp Tyr Trp Gln Leu
450                 455                 460

Glu Glu Ala Cys Ser Tyr Arg Pro Gly Gln Thr Ser Pro Tyr Ala Cys
465                 470                 475                 480

Lys Glu Trp Arg His Val Glu Asp Phe Gln Gly Gly Asn Lys Ile Glu
                485                 490                 495

Val Thr Lys Asn Gln Tyr Ala Leu Ile Glu Gly Lys Asn Lys Thr Val
                500                 505                 510

Ser Thr Leu Val Ile Gln Ala Ala Asn Val Ser Ala Leu Tyr Lys Cys
                515                 520                 525

Glu Ala Ile Asn Lys Ala Gly Arg Gly Glu Arg Val Ile Ser Phe His
530                 535                 540

Val Ile Arg Gly Pro Glu Ile Thr Val Gln Pro Ala Ala Gln Pro Thr
```

```
                545                 550                 555                 560
Glu Gln Glu Ser Val Ser Leu Leu Cys Thr Ala Asp Arg Asn Thr Phe
                565                 570                 575
Glu Asn Leu Thr Trp Tyr Lys Leu Gly Ser Gln Ala Thr Ser Val His
                580                 585                 590
Met Gly Glu Ser Leu Thr Pro Val Cys Lys Asn Leu Asp Ala Leu Trp
                595                 600                 605
Lys Leu Asn Gly Thr Met Phe Ser Asn Ser Thr Asn Asp Ile Leu Ile
                610                 615                 620
Val Ala Phe Gln Asn Ala Ser Leu Gln Asp Gln Gly Asp Tyr Val Cys
625                 630                 635                 640
Ser Ala Gln Asp Lys Lys Thr Lys Lys Arg His Cys Leu Val Lys Gln
                645                 650                 655
Leu Ile Ile Leu Glu Arg Met Ala Pro Met Ile Thr Gly Asn Leu Glu
                660                 665                 670
Asn Gln Thr Thr Thr Ile Gly Glu Thr Ile Glu Val Thr Cys Pro Ala
                675                 680                 685
Ser Gly Asn Pro Thr Pro His Ile Thr Trp Phe Lys Asp Asn Glu Thr
                690                 695                 700
Leu Val Glu Asp Ser Gly Ile Val Leu Arg Asp Gly Asn Arg Asn Leu
705                 710                 715                 720
Thr Ile Arg Arg Val Arg Lys Glu Asp Gly Gly Leu Tyr Thr Cys Gln
                725                 730                 735
Ala Cys Asn Val Leu Gly Cys Ala Arg Ala Glu Thr Leu Phe Ile Ile
                740                 745                 750
Glu Gly Ala Gln Glu Lys Thr Asn Leu Glu Val Ile Ile Leu Val Gly
                755                 760                 765
Thr Ala Val Ile Ala Met Phe Phe Trp Leu Leu Val Ile Leu Val
                770                 775                 780
Arg Thr Val Lys Arg Ala Asn Glu Gly Glu Leu Lys Thr Gly Tyr Leu
785                 790                 795                 800
Ser Ile Val Met Asp Pro Asp Glu Leu Pro Leu Asp Glu Arg Cys Glu
                805                 810                 815
Arg

<210> SEQ ID NO 28
<211> LENGTH: 815
<212> TYPE: PRT
<213> ORGANISM: Rattus norvegicus
<220> FEATURE:
<223> OTHER INFORMATION: rat vascular endothelial growth factor (VEGF,
      VPF, vasculotropin) receptor-2 (VEGFR-2), kinase domain receptor
      (KDR), fetal liver kinase 1 (Flk-1), type III receptor tyrosine
      kinase, kinase NYK extracellular and transmembrane domains

<400> SEQUENCE: 28

Met Glu Ser Arg Ala Leu Leu Ala Val Ala Leu Trp Phe Cys Val Glu
1               5                   10                  15
Thr Arg Ala Ala Ser Val Gly Leu Pro Gly Asp Ser Leu His Pro Pro
                20                  25                  30
Lys Leu Ser Thr Gln Lys Asp Ile Leu Thr Ile Leu Ala Asn Thr Thr
            35                  40                  45
Leu Gln Ile Thr Cys Arg Gly Gln Arg Asp Leu Asp Trp Leu Trp Pro
        50                  55                  60
Asn Thr Pro Arg Asp Ser Glu Glu Arg Val Leu Val Thr Glu Cys Gly
65                  70                  75                  80
```

```
Asp Ser Ile Phe Cys Lys Thr Leu Thr Val Pro Arg Val Val Gly Asn
                85                  90                  95

Asp Thr Gly Ala Tyr Lys Cys Phe Tyr Arg Asp Thr Asp Val Ser Ser
            100                 105                 110

Ile Val Tyr Val Tyr Val Gln Asp His Arg Ser Pro Phe Ile Ala Ser
        115                 120                 125

Val Ser Asp Glu His Gly Ile Val Tyr Ile Thr Glu Asn Lys Asn Lys
130                 135                 140

Thr Val Val Ile Pro Cys Arg Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Glu Lys Gly Phe Thr Ile Pro Ser Tyr Met Ile
            180                 185                 190

Ser Tyr Ala Gly Met Val Phe Cys Glu Ala Lys Ile Asn Asp Glu Thr
        195                 200                 205

Tyr Gln Ser Ile Met Tyr Ile Val Leu Val Val Gly Tyr Arg Ile Tyr
    210                 215                 220

Asp Val Val Leu Ser Pro Pro His Glu Ile Glu Leu Ser Ala Gly Glu
225                 230                 235                 240

Lys Leu Val Leu Asn Cys Thr Ala Arg Thr Glu Leu Asn Val Gly Leu
                245                 250                 255

Asp Phe Ser Trp Gln Phe Pro Ser Ser Lys His Gln His Lys Lys Ile
            260                 265                 270

Val Asn Arg Asp Val Lys Ser Leu Pro Gly Thr Val Ala Lys Met Phe
        275                 280                 285

Leu Ser Thr Leu Thr Ile Asp Ser Val Thr Lys Ser Asp Gln Gly Glu
    290                 295                 300

Tyr Thr Cys Thr Ala Tyr Ser Gly Leu Met Thr Lys Lys Asn Lys Thr
305                 310                 315                 320

Phe Val Arg Val His Thr Lys Pro Phe Ile Ala Phe Gly Ser Gly Met
                325                 330                 335

Lys Ser Leu Val Glu Ala Thr Val Gly Ser Gln Val Arg Ile Pro Val
            340                 345                 350

Lys Tyr Leu Ser Tyr Pro Ala Pro Asp Ile Lys Trp Tyr Arg Asn Gly
        355                 360                 365

Arg Pro Ile Glu Ser Asn Tyr Thr Met Ile Val Gly Asp Glu Leu Thr
    370                 375                 380

Ile Met Glu Val Ser Glu Arg Asp Ala Gly Asn Tyr Thr Val Ile Leu
385                 390                 395                 400

Thr Asn Pro Ile Ser Met Glu Lys Gln Ser His Met Val Ser Leu Val
                405                 410                 415

Val Asn Val Pro Pro Gln Ile Gly Glu Lys Ala Leu Ile Ser Pro Met
            420                 425                 430

Asp Ser Tyr Gln Tyr Gly Thr Met Gln Thr Leu Thr Cys Thr Val Tyr
        435                 440                 445

Ala Asn Pro Pro Leu His His Ile Gln Trp Tyr Trp Gln Leu Glu Glu
    450                 455                 460

Ala Cys Ser Tyr Arg Pro Ser Gln Thr Asn Pro Tyr Thr Cys Lys Glu
465                 470                 475                 480

Trp Arg His Val Lys Asp Phe Gln Gly Gly Asn Lys Ile Glu Val Thr
                485                 490                 495
```

```
Lys Asn Gln Tyr Ala Leu Ile Glu Gly Lys Asn Lys Thr Val Ser Thr
                500                 505                 510

Leu Val Ile Gln Ala Ala Tyr Val Ser Ala Leu Tyr Lys Cys Glu Ala
            515                 520                 525

Ile Asn Lys Ala Gly Arg Gly Glu Arg Val Ile Ser Phe His Val Ile
        530                 535                 540

Arg Gly Pro Glu Ile Thr Val Gln Pro Ala Thr Gln Pro Thr Glu Arg
545                 550                 555                 560

Glu Ser Met Ser Leu Leu Cys Thr Ala Asp Arg Asn Thr Phe Glu Asn
                565                 570                 575

Leu Thr Trp Tyr Lys Leu Gly Ser Gln Ala Thr Ser Val His Met Gly
            580                 585                 590

Glu Ser Leu Thr Pro Val Cys Lys Asn Leu Asp Ala Leu Trp Lys Leu
        595                 600                 605

Asn Gly Thr Val Phe Ser Asn Ser Thr Asn Asp Ile Leu Ile Val Ala
610                 615                 620

Phe Gln Asn Ala Ser Leu Gln Asp Gln Asn Asp Tyr Val Cys Ser Ala
625                 630                 635                 640

Gln Asp Lys Lys Thr Lys Lys Arg His Cys Leu Val Lys Gln Leu Val
                645                 650                 655

Ile Leu Glu Arg Met Ala Pro Met Ile Thr Gly Asn Leu Glu Asn Gln
            660                 665                 670

Thr Thr Thr Ile Gly Glu Thr Ile Glu Val Val Cys Pro Thr Ser Gly
        675                 680                 685

Asn Pro Thr Pro Leu Ile Thr Trp Phe Lys Asp Asn Glu Thr Leu Val
690                 695                 700

Glu Asp Ser Gly Ile Val Leu Lys Asp Gly Asn Arg Asn Leu Thr Ile
705                 710                 715                 720

Arg Arg Val Arg Lys Glu Asp Gly Gly Leu Tyr Thr Cys Gln Ala Cys
                725                 730                 735

Asn Val Leu Gly Cys Ala Arg Ala Glu Thr Leu Phe Ile Ile Glu Gly
            740                 745                 750

Val Gln Glu Lys Thr Asn Leu Glu Val Ile Ile Leu Val Gly Thr Ala
        755                 760                 765

Val Ile Ala Met Phe Phe Trp Leu Leu Leu Val Ile Leu Val Arg Thr
770                 775                 780

Val Lys Arg Ala Asn Glu Gly Glu Leu Lys Thr Gly Tyr Leu Ser Ile
785                 790                 795                 800

Val Met Asp Pro Asp Glu Leu Pro Leu Asp Glu Arg Cys Glu Arg
                805                 810                 815

<210> SEQ ID NO 29
<211> LENGTH: 812
<212> TYPE: PRT
<213> ORGANISM: Homo sapiens
<220> FEATURE:
<223> OTHER INFORMATION: human vascular endothelial growth factor (VEGF,
      VPF, vasculotropin) receptor-1 (VEGFR-1), Fms-like tyrosine
      kinase-1 (Flt-1), tyrosine-protein kinase FRT
      extracellular and transmembrane regions

<400> SEQUENCE: 29

Met Val Ser Tyr Trp Asp Thr Gly Val Leu Leu Cys Ala Leu Leu Ser
  1               5                  10                  15

Cys Leu Leu Leu Thr Gly Ser Ser Ser Gly Ser Lys Leu Lys Asp Pro
             20                  25                  30
```

-continued

```
Glu Leu Ser Leu Lys Gly Thr Gln His Ile Met Gln Ala Gly Gln Thr
             35                  40                  45
Leu His Leu Gln Cys Arg Gly Glu Ala Ala His Lys Trp Ser Leu Pro
 50                  55                  60
Glu Met Val Ser Lys Glu Ser Glu Arg Leu Ser Ile Thr Lys Ser Ala
 65                  70                  75                  80
Cys Gly Arg Asn Gly Lys Gln Phe Cys Ser Thr Leu Thr Leu Asn Thr
                 85                  90                  95
Ala Gln Ala Asn His Thr Gly Phe Tyr Ser Cys Lys Tyr Leu Ala Val
            100                 105                 110
Pro Thr Ser Lys Lys Lys Glu Thr Glu Ser Ala Ile Tyr Ile Phe Ile
            115                 120                 125
Ser Asp Thr Gly Arg Pro Phe Val Glu Met Tyr Ser Glu Ile Pro Glu
130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
            180                 185                 190
Ile Ile Ser Asn Ala Thr Tyr Lys Glu Ile Gly Leu Leu Thr Cys Glu
            195                 200                 205
Ala Thr Val Asn Gly His Leu Tyr Lys Thr Asn Tyr Leu Thr His Arg
        210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
            260                 265                 270
Asn Lys Arg Ala Ser Val Arg Arg Arg Ile Asp Gln Ser Asn Ser His
            275                 280                 285
Ala Asn Ile Phe Tyr Ser Val Leu Thr Ile Asp Lys Met Gln Asn Lys
        290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
            355                 360                 365
Trp Leu Lys Asp Gly Leu Pro Ala Thr Glu Lys Ser Ala Arg Tyr Leu
        370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
            435                 440                 445
Arg Gln Ile Leu Thr Cys Thr Ala Tyr Gly Ile Pro Gln Pro Thr Ile
```

```
                450                 455                 460
Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
                500                 505                 510

Glu Gly Lys Asn Lys Met Ala Ser Thr Leu Val Val Ala Asp Ser Arg
                515                 520                 525

Ile Ser Gly Ile Tyr Ile Cys Ile Ala Ser Asn Lys Val Gly Thr Val
                530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
                580                 585                 590

Arg Thr Val Asn Asn Arg Thr Met His Tyr Ser Ile Ser Lys Gln Lys
                595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
                660                 665                 670

Ala Ile Ser Ser Ser Thr Thr Leu Asp Cys His Ala Asn Gly Val Pro
                675                 680                 685

Glu Pro Gln Ile Thr Trp Phe Lys Asn Asn His Lys Ile Gln Gln Glu
                690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
                740                 745                 750

Asp Lys Ser Asn Leu Glu Leu Ile Thr Leu Thr Cys Thr Cys Val Ala
                755                 760                 765

Ala Thr Leu Phe Trp Leu Leu Leu Thr Leu Leu Ile Arg Lys Met Lys
770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg
                805                 810

<210> SEQ ID NO 30
<211> LENGTH: 900
<212> TYPE: PRT
<213> ORGANISM: Homo sapiens
<220> FEATURE:
<223> OTHER INFORMATION: human neuropilin-1 (NRP-1), vascular
      endothelial cell growth factor 165 receptor, including signal
      peptide extracellular and transmembrane domains

<400> SEQUENCE: 30
```

```
Met Glu Arg Gly Leu Pro Leu Leu Cys Ala Val Leu Ala Leu Val Leu
 1               5                  10                  15

Ala Pro Ala Gly Ala Phe Arg Asn Asp Lys Cys Gly Asp Thr Ile Lys
                20                  25                  30

Ile Glu Ser Pro Gly Tyr Leu Thr Ser Pro Gly Tyr Pro His Ser Tyr
            35                  40                  45

His Pro Ser Glu Lys Cys Glu Trp Leu Ile Gln Ala Pro Asp Pro Tyr
        50                  55                  60

Gln Arg Ile Met Ile Asn Phe Asn Pro His Phe Asp Leu Glu Asp Arg
 65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
                100                 105                 110

Val Ser Ser Gly Pro Phe Leu Phe Ile Lys Phe Val Ser Asp Tyr Glu
            115                 120                 125

Thr His Gly Ala Gly Phe Ser Ile Arg Tyr Glu Ile Phe Lys Arg Gly
        130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
                180                 185                 190

Asp Leu Glu Pro Asp Ser Asn Pro Pro Gly Gly Met Phe Cys Arg Tyr
            195                 200                 205

Asp Arg Leu Glu Ile Trp Asp Gly Phe Pro Asp Val Gly Pro His Ile
        210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
        275                 280                 285

Asp Gln Ile Thr Ala Ser Ser Gln Tyr Ser Thr Asn Trp Ser Ala Glu
        290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415
```

Met Arg Phe Glu Val Tyr Gly Cys Lys Ile Thr Asp Tyr Pro Cys Ser
        420                 425                 430

Gly Met Leu Gly Met Val Ser Gly Leu Ile Ser Asp Ser Gln Ile Thr
        435                 440                 445

Ser Ser Asn Gln Gly Asp Arg Asn Trp Met Pro Glu Asn Ile Arg Leu
450                 455                 460

Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Glu Lys Ile Val Arg
                485                 490                 495

Gly Ile Ile Ile Gln Gly Gly Lys His Arg Glu Asn Lys Val Phe Met
            500                 505                 510

Arg Lys Phe Lys Ile Gly Tyr Ser Asn Asn Gly Ser Asp Trp Lys Met
        515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
        580                 585                 590

Thr Thr Pro Asn Gly Asn Leu Val Asp Glu Cys Asp Asp Gln Ala
        595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
        660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr His Gln Leu Val
        740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
        770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
        820                 825                 830

Tyr Glu Gly Glu Gly Glu Gly Asp Lys Asn Ile Ser Arg Lys Pro Gly

```
                         835                 840                 845

Asn Val Leu Lys Thr Leu Asp Pro Ile Leu Ile Thr Ile Ile Ala Met
        850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn
        900

<210> SEQ ID NO 31
<211> LENGTH: 47
<212> TYPE: DNA
<213> ORGANISM: Artificial Sequence
<220> FEATURE:
<223> OTHER INFORMATION: Description of Artificial Sequence:PCR
      amplification sense primer FasL1

<400> SEQUENCE: 31
gggctcgagg gactagtgaa aaaaggagc tgaggaaagt ggcccat                    47

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence:PCR
      amplification antisense primer FasL2

<400> SEQUENCE: 32
gggtctagat cttagagctt atataagccg aaaaacgtct g                         41

<210> SEQ ID NO 33
<211> LENGTH: 84
<212> TYPE: DNA
<213> ORGANISM: Artificial Sequence
<220> FEATURE:
<223> OTHER INFORMATION: Description of Artificial Sequence:portion of
      pFLAG-CMV-3 vector

<400> SEQUENCE: 33
gactacaaag acgatgacga caagcttgcg gccgcgaatt catcgataga tctgatatcg     60
gtaccagtcg actctagagg atcc                                            84

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence:translation
      of portion of pFLAG-CMV-3 vector

<400> SEQUENCE: 34

Asp Tyr Lys Asp Asp Asp Lys Leu Ala Ala Ala Asn Ser
  1               5                  10

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence:portion of
      pFLAG-CMV-3 vector NotI fragment

<400> SEQUENCE: 35
```

```
gactacaaag acgatgacga caagcttgc                                    29
```

<210> SEQ ID NO 36
<211> LENGTH: 55
<212> TYPE: DNA
<213> ORGANISM: Artificial Sequence
<220> FEATURE:
<223> OTHER INFORMATION: Description of Artificial Sequence:portion of
      pFLAG-CMV-3 vector NotI fragment

<400> SEQUENCE: 36

```
ggccgcgaat tcatcgatag atctgatatc ggtaccagtc gactctagag gatcc       55
```

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence:portion of
      pFLAG-CMV-3 vector NotI fragment

<400> SEQUENCE: 37

```
gactacaaag acgatgacga caagcttgcg gcc                               33
```

<210> SEQ ID NO 38
<211> LENGTH: 51
<212> TYPE: DNA
<213> ORGANISM: Artificial Sequence
<220> FEATURE:
<223> OTHER INFORMATION: Description of Artificial Sequence:portion of
      pFLAG-CMV-3 vector NotI fragment

<400> SEQUENCE: 38

```
ggatcctcta gagtcgactg gtaccgatat cagatctatc gatgaattcg c           51
```

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence:translation
      of portion of pFLAG-CMV-3 vector NotI fragment

<400> SEQUENCE: 39

```
Asp Tyr Lys Asp Asp Asp Asp Lys Leu Ala Ala
 1               5                  10
```

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence:portion of
      pBJ/FlkhFasL(D1-D3/139-281) plasmid

<400> SEQUENCE: 40

```
gagacccgag ccgcctctgt g                                            21
```

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence:portion of
      pBJ/FlkhFasL(D1-D3/139-281) plasmid

<400> SEQUENCE: 41
gctttcggta gtgctcgagg gactagtgaa aaaa                                   34

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence:translation
     of portion of pBJ/FlkhFasL(D1-D3/139-281) plasmid

<400> SEQUENCE: 42

Glu Thr Arg Ala Ala Ser Val
 1               5

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence:translation
     of portion of pBJ/FlkhFasL(D1-D3/139-281) plasmid

<400> SEQUENCE: 43

Ala Phe Gly Ser Ala Arg Gly Thr Ser Glu Lys
 1               5                  10

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence:portion of
     pBJ/FlkhFasL(D1-D3/139-281) plasmid AvaI fragment

<400> SEQUENCE: 44
ccgagccgcc tctgtg                                                       16

<210> SEQ ID NO 45
<211> LENGTH: 14
<212> TYPE: DNA
<213> ORGANISM: Artificial Sequence
<220> FEATURE:
<223> OTHER INFORMATION: Description of Artificial Sequence:portion of
     pBJ/FlkhFasL(D1-D3/139-281) plasmid AvaI fragment

<400> SEQUENCE: 45
gctttcggta gtgc                                                         14

<210> SEQ ID NO 46
<211> LENGTH: 12
<212> TYPE: DNA
<213> ORGANISM: Artificial Sequence
<220> FEATURE:
<223> OTHER INFORMATION: Description of Artificial Sequence:portion of
     pBJ/FlkhFasL(D1-D3/139-281) plasmid AvaI fragment

<400> SEQUENCE: 46
gccgcctctg tg                                                           12

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence:portion of
     pBJ/FlkhFasL(D1-D3/139-281) plasmid AvaI fragment

```
<400> SEQUENCE: 47
tcgagcacta ccgaaagc                                                 18

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence:translation
      of portion of pBJ/FlkhFasL(D1-D3/139-281) plasmid AvaI fragment

<400> SEQUENCE: 48

Ala Ala Ser Val
  1

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence:translation
      of portion of pBJ/FlkhFasL(D1-D3/139-281) plasmid AvaI fragment

<400> SEQUENCE: 49

Ala Phe Gly Ser Ala Arg
  1               5

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence:translation
      of portion of pBJ/FlkhFasL(D1-D3/139-281) plasmid
      AvaI fragment

<400> SEQUENCE: 50

Ala Phe Gly Ser
  1

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence:portion of
      pFLAG/FlkFasL(D1-D3) plasmid

<400> SEQUENCE: 51
gactacaaag acgatgacga caagcttgcg gccgccgcct ctgtg                   45

<210> SEQ ID NO 52
<211> LENGTH: 69
<212> TYPE: DNA
<213> ORGANISM: Artificial Sequence
<220> FEATURE:
<223> OTHER INFORMATION: Description of Artificial Sequence:portion of
      pFLAG/FlkFasL(D1-D3) plasmid

<400> SEQUENCE: 52
gctttcggta gtgcggccgc gaattcatcg atagatctga tatcggtacc agtcgactct   60
agaggatcc                                                           69

<210> SEQ ID NO 53
<211> LENGTH: 15
<212> TYPE: PRT
```

-continued

<213> ORGANISM: Artificial Sequence
<220> FEATURE:
<223> OTHER INFORMATION: Description of Artificial Sequence:translation
      of portion of pFLAG/FlkFasL(D1-D3) plasmid

<400> SEQUENCE: 53

Asp Tyr Lys Asp Asp Asp Lys Leu Ala Ala Ala Ser Val
1               5                   10                  15

<210> SEQ ID NO 54
<211> LENGTH: 834
<212> TYPE: DNA
<213> ORGANISM: Artificial Sequence
<220> FEATURE:
<223> OTHER INFORMATION: Description of Artificial Sequence:FLAG-tagged
      R1[D2]FasL protein

<400> SEQUENCE: 54
atgtctgcac ttctgatcct agctcttgtt ggagctgcag ttgctgacta caaagacgat      60
gacgacaagc ttgcggccgc cagtgataca ggtagacctt cgtagagat gtacagtgaa      120 atccccgaaa ttatacacat gactgaagga agggagctcg tcattccctg ccgggttacg      180
tcacctaaca tcactgttac tttaaaaaag tttccacttg acactttgat ccctgatgga      240
aaacgcataa tctgggacag tagaaagggc ttcatcatat caaatgcaac gtacaaagaa      300
atagggcttc tgacctgtga agcaacagtc aatgggcatt tgtataagac aaactatctc      360
acacatcgac aaaccaatac aatcatagct cgagggacta gtgaaaaaa ggagctgagg       420 aaagtggccc atttaacagg caagtccaac tcaaggtcca tgcctctgga atgggaagac      480
acctatggaa ttgtcctgct ttctggagtg aagtataaga agggtggcct tgtgatcaat      540
gaaactgggc tgtactttgt atattccaaa gtatacttcc ggggtcaatc ttgcaacaac      600 ctgccctga gccacaaggt ctacatgagg aactctaagt atccccagga tctggtgatg      660
atggagggga gatgatgag ctactgcact actgggcaga tgtgggcccg cagcagctac      720
ctgggggcag tgttcaatct taccagtgct gatcatttat atgtcaacgt atctgagctc      780
tctctggtca ttttgagga atctcagacg ttttcggct tatataagct ctaa            834

<210> SEQ ID NO 55
<211> LENGTH: 102
<212> TYPE: PRT
<213> ORGANISM: Homo sapiens
<220> FEATURE:
<223> OTHER INFORMATION: human vascular endothelial growth factor (VEGF,
      VPF, vasculotropin) receptor-1 (VEGFR-1) domain 2 (D2),
      R1[D2], VEGFR1 amino acids 129-230

<400> SEQUENCE: 55

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

```
Gln Thr Asn Thr Ile Ile
            100

<210> SEQ ID NO 56
<211> LENGTH: 34
<212> TYPE: DNA
<213> ORGANISM: Artificial Sequence
<220> FEATURE:
<223> OTHER INFORMATION: Description of Artificial Sequence:R1[D2]FasL
      PCR amplification 5' primer

<400> SEQUENCE: 56
cccgcggccg ccagtgatac aggtagacct ttcg                               34

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence:R1[D2]FasL
      PCR amplification 3' primer

<400> SEQUENCE: 57
ggcctcgagc tatgattgta ttggtttgtc g                                  31
```